US012806284B2

(12) United States Patent
Ueda et al.

(10) Patent No.: US 12,806,284 B2
(45) **Date of Patent: *Nov. 24, 2026**

(54) ANTIBODY-BOUND NANOPARTICLES

(71) Applicant: University of Washington, Seattle, WA (US)

(72) Inventors: George Ueda, Seattle, WA (US); James Lazarovits, Seattle, WA (US); Jorge Fallas, Seattle, WA (US); David Baker, Seattle, WA (US); Hannele Ruohola-Baker, Seattle, WA (US); Robert Divine, Seattle, WA (US); Yan (Blair) Ting Zhao, Seattle, WA (US); Julie Mathieu, Seattle, WA (US); Neil P. King, Seattle, WA (US); Marti Rae Tooley, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 854 days.

This patent is subject to a terminal disclaimer.

(21) Appl. No.: 18/000,004

(22) PCT Filed: Jun. 7, 2021

(86) PCT No.: PCT/US2021/036117

§ 371 (c)(1),
(2) Date: Nov. 28, 2022

(87) PCT Pub. No.: WO2021/252327

PCT Pub. Date: Dec. 16, 2021

(65) Prior Publication Data

US 2023/0233707 A1 Jul. 27, 2023

Related U.S. Application Data

(60) Provisional application No. 63/088,586, filed on Oct. 7, 2020, provisional application No. 63/088,576, filed on Oct. 7, 2020, provisional application No. 63/085,351, filed on Sep. 30, 2020, provisional application No. 63/036,062, filed on Jun. 8, 2020.

(51) Int. Cl.

| | |
|---|---|
| ***A61K 47/00*** | (2006.01) |
| ***A61K 47/68*** | (2017.01) |
| ***A61K 47/69*** | (2017.01) |
| ***A61P 11/00*** | (2006.01) |
| ***A61P 35/00*** | (2006.01) |
| ***C07K 14/515*** | (2006.01) |
| ***C07K 16/28*** | (2006.01) |

(52) U.S. Cl.

CPC ...... *A61K 47/6931* (2017.08); *A61K 47/6849* (2017.08); *A61P 11/00* (2018.01); *A61P 35/00* (2018.01); *C07K 14/515* (2013.01); *C07K 16/2878* (2013.01); *C07K 2317/75* (2013.01); *C07K 2317/92* (2013.01); *C07K 2319/30* (2013.01); *C07K 2319/705* (2013.01)

(58) Field of Classification Search

None

See application file for complete search history.

(56) References Cited

U.S. PATENT DOCUMENTS

| | | | |
|---|---|---|---|
| 7,858,070 B2 | 12/2010 | Chang et al. | |
| 7,879,985 B2 | 2/2011 | Ursøet al. | |
| 9,683,051 B2 | 6/2017 | Masazumi et al. | |
| 9,845,237 B2 | 12/2017 | Hsian-Rong et al. | |
| 9,931,410 B2 | 4/2018 | Valencia et al. | |
| 10,818,377 B2 | 10/2020 | Baker et al. | |
| 10,988,514 B2 | 4/2021 | Baker et al. | |
| 2004/0018587 A1 | 1/2004 | Makowski et al. | |
| 2006/0058228 A1* | 3/2006 | Kelly | G01N 33/57535 514/19.3 |
| 2009/0226525 A1 | 9/2009 | de los Rios et al. | |
| 2013/0337066 A1 | 12/2013 | Zhang et al. | |
| 2016/0058828 A1 | 3/2016 | Dumont et al. | |
| 2016/0137716 A1 | 5/2016 | Andaloussi et al. | |
| 2018/0137234 A1 | 5/2018 | Baker et al. | |
| 2019/0012428 A1 | 1/2019 | Parmeggiani et al. | |
| 2019/0240282 A1 | 8/2019 | Baldwin et al. | |
| 2021/0101945 A1 | 4/2021 | Baker et al. | |
| 2021/0183465 A1 | 6/2021 | Baker et al. | |
| 2023/0142283 A1 | 5/2023 | Baker et al. | |
| 2023/0233707 A1 | 7/2023 | Ueda et al. | |

FOREIGN PATENT DOCUMENTS

| | | |
|---|---|---|
| WO | 2017106728 A2 | 7/2017 |
| WO | 2020190852 A2 | 9/2020 |

(Continued)

OTHER PUBLICATIONS

H.H. Guo, J. Choe, & L.A. Loeb, Protein tolerance to random amino acid change, Proc. Natl. Acad. Sci. U.S.A. 101 (25) 9205-9210, (2004). (Year: 2004).*

McVey and Beatty. Facts and Hopes of CD40 Agonists in Cancer Immunotherapy. Clin Cancer Res. Jun. 3, 2025;31(11):2079-2087. (Year: 2025).*

Min, J. et al. (2014). "Lumazine synthase protein cage nanoparticles as modular delivery platforms for targeted drug delivery." RSC Advances 4(89): 48596-48600.

Moon, H. et al. "Developing genetically engineered encapsulin protein cage nanoparticles as a targeted delivery nanoplatform." Biomacromolecules vol. 15,10 (2014): 3794-801. doi:10.1021/bm501066m.

(Continued)

*Primary Examiner* — Melissa L Fisher
*Assistant Examiner* — Sara E Konopelski Snavely
(74) *Attorney, Agent, or Firm* — MCDONNELL BOEHNEN HULBERT & BERGHOFF LLP

(57) ABSTRACT

Antibody particles are disclosed comprising polypeptides comprising an (Fc) binding domain, a helical polypeptide monomer, and an oligomer domain, and either Tie2 antibodies or dimers, or tumor necrosis factor receptor superfamily antibodies, and uses thereof.

14 Claims, 11 Drawing Sheets

Specification includes a Sequence Listing.

(56) References Cited

FOREIGN PATENT DOCUMENTS

| | | | |
|---|---|---|---|
| WO | 2021178508 | A1 | 9/2021 |
| WO | 2021252327 | A2 | 12/2021 |

OTHER PUBLICATIONS

Moon, H. et al. "Fabrication of uniform layer-by-layer assemblies with complementary protein cage nanobuilding blocks via simple His-tag/metal recognition." Journal of materials chemistry. B vol. 1,35 (2013): 4504-4510. doi:10.1039/c3tb20554a.
Peer, D. et al. "Nanocarriers as an emerging platform for cancer therapy." Nature nanotechnology vol. 2, 12 (2007): 751-60. doi: 10.1038/nnano.2007.387.
Rhodes, A. "Developing a cell line standard for HER2/neu." Cancer biomarkers: section A of Disease markers vol. 1,4-5 (2005): 229-32. doi: 10.3233/cbm-2005-14-505.
Ritchie, M. et al. "Implications of receptor-mediated endocytosis and intracellular trafficking dynamics in the development of antibody drug conjugates." mAbs vol. 5, 1 (2013): 13-21. doi:10.4161/mabs.22854.
Seebeck, F. P. et al. "A simple tagging system for protein encapsulation." Journal of the American Chemical Society vol. 128,14 (2006): 4516-7. doi: 10.1021/ja058363s.
Shenton, W. et al. "Synthesis of Nanophase Iron Oxide in Lumazine Synthase Capsids." Angewandte Chemie (International ed. in English) vol. 40,2 (2001 ): 442-445. doi:10.1002/1521-3773(20010119)40:2<442::AID-ANIE442>3.0.CO;2-2.
Shi, D. et al. "Engineered multifunctional nanocarriers for cancer diagnosis and therapeutics." Small (Weinheim an der Bergstrasse, Germany) vol. 7, 18 (2011 ): 2549-67. doi:10.1002/smll.201100436.
Shi, M. et al. "Immuno-polymeric nanoparticles by Diels-Alder chemistry." Angewandte Chemie (International ed. In English) vol. 46,32 (2007): 6126-31. doi:10.1002/anie.200701032.
Strable, E. and Finn, M. G. "Chemical modification of viruses and virus-like particles." Current topics in microbiology and immunology vol. 327 (2009 ): 1-21. doi: 10 .1007 /978-3-540-69379-6 _ 1.
Suci, P.A. et al. "A streptavidin-protein cage Janus particle for polarized targeting and modular functionalization." Journal of the American Chemical Society vol. 131,26 (2009): 9164-5. doi:10.1021/ja9035187.
Sutton, D. et al. "Functionalized micellar systems for cancer targeted drug delivery." Pharmaceutical research vol. 24,6 (2007): 1029-46. doi:10.1007/s11095-006-9223-y.
Tatur, J. et al. "Crystal structure of the ferritin from the hyperthermophilic archaeal anaerobe Pyrococcus furiosus." Journal of biological inorganic chemistry : JBIC : a publication of the Society of Biological Inorganic Chemistry vol. 12,5 (2007): 615-30. doi:10.1007/s00775-007-0212-3.
Tong, G. J. et al. "Viral capsid DNA aptamer conjugates as multivalent cell-targeting vehicles." Journal of the American Chemical Society vol. 131,31 (2009): 11174-8. doi:10.1021/ja903857f.
Torchilin, V. P. "Recent advances with liposomes as pharmaceutical carriers." Nature reviews. Drug discovery vol. 4,2 (2005): 145-60. doi:10.1038/nrd1632.
Vasir, J. K. et al. Nanosystems in Drug Targeting: Opportunities and Challenges, Current Nanoscience 2005; 1 (1). https://dx.doi.org/10.217 4/1573413052953110.
Von Mehren, M. et al. "Monoclonal antibody therapy for cancer." Annual review of medicine vol. 54 (2003): 343-69. doi:10.1146/annurev.med.54.101601.152442.
Willner, D. et al. "(6-Maleimidocaproyl)hydrazone of doxorubicin—a new derivative for the preparation of immunoconjugates of doxorubicin." Bioconjugate chemistry vol. 4,6 (1993): 521-7. doi:10.1021/bc00024a015.
Worsdorfer, B. et al. "Directed evolution of a protein container." Science (New York, N.Y.) vol. 331,6017 (2011 ):589-92. doi:10.1126/science.1199081.
Worsdorfer, B. et al. "Efficient in vitro encapsulation of protein cargo by an engineered protein container." Journal of the American Chemical Society vol. 134,2 (2012): 909-11. doi:10.1021/ja211011k.
Zamboni, W. C. "Liposomal, nanoparticle, and conjugated formulations of anticancer agents." Clinical cancer research: an official journal of the American Association for Cancer Research vol. 11,23 (2005): 8230-4. doi:10.1158/1078-0432.CCR-05-1895.
Zhang, K. et al. "Antibody-linked spherical nucleic acids for cellular targeting." Journal of the American Chemical Society vol. 134,40 (2012): 16488-91. doi: 10.1021 /ja306854d.
Zhang, X et al. "X-ray structure analysis and crystallographic refinement of lumazine synthase from the hyperthermophile Aquifex aeolicus at 1.6 A resolution: determinants of thermostability revealed from structural comparisons." Journal of molecular biology vol. 306,5 (2001 ): 1099-114. doi:10.1006/jmbi.2000.4435.
Zhang, X. et al. "A structure-based model of the reaction catalyzed by lumazine synthase from Aquifex aeolicus." Journal of molecular biology vol. 328, 1 (2003): 167-82. doi:10.1016/s0022-2836(03)00186-4.
Zhao et al. "F-domain valency determines outcome of signaling through the Angiopoietin pathway" EMBO Reports 22: e53471, (Oct. 2021).
International Search Report and Written Opinion of PCT/US2021/036117, mailed on Jan. 19, 2022.
Lim et al. "Self-assembled protein nanocarrier for intracellular delivery of antibody". J Control Release, 249:1-10, (Jan. 2017).
Marcandalli et al. "Induction of Potent Neutralizing Antibody Responses by a Designed Protein Nanoparticle Vaccine for Respiratory Syncytial Virus". Cell 176(6): 1420-1431, (Mar. 2019).
Allen, T. M. "Ligand-targeted therapeutics in anticancer therapy." Nature reviews. Cancer vol. 2, 10 (2002): 750-63. doi: 10 .1038/nrc903.
Arap, W. et al. "Cancer treatment by targeted drug delivery to tumor vasculature in a mouse model." Science (New York, N.Y.) vol. 279,5349 (1998): 377-80. doi:10.1126/science.279.5349.377.
Ashley, C. E. et al. "Cell-specific delivery of diverse cargos by bacteriophage MS2 virus-like particles." ACS nano vol. 5,7 (2011): 5729-45. doi:10.1021/nn201397z.
Bartlett, D. W. et al. "Impact of tumor-specific targeting on the biodistribution and efficacy of siRNA nanoparticles measured by multimodality in vivo imaging." Proceedings of the National Academy of Sciences of the United States of America vol. 104,39 (2007): 15549-54. doi:10.1073/pnas.0707461104.
Beck, T. et al. "Construction of Matryoshka-type structures from supercharged protein nanocages." Angewandte Chemie (International ed. in English) vol. 54,3 (2015): 937-40. doi:10.1002/anie.201408677.
Biju, V. et al. "Delivering quantum dots to cells: bioconjugated quantum dots for targeted and nonspecific extracellular and intracellular imaging." Chemical Society reviews vol. 39,8 (2010): 3031-56. doi:10.1039/b926512k.
Bon Roy, K. et al. "Comparison of random and oriented immobilisation of antibody fragments on mixed self-9 assembled monolayers." Journal of immunological methods vol. 312, 1-2 (2006): 167-81. doi:10.1016/j.jim.2006.03.007.
Braisted, A. C. and Wells, J. A. "Minimizing a binding domain from protein A." Proceedings of the National Academy of Sciences of the United States of America vol. 93, 12 (1996): 5688-92. doi:10.1073/pnas.93.12.5688.
Brigger, I. et al. "Nanoparticles in cancer therapy and diagnosis." Advanced drug delivery reviews vol. 54,5 (2002): 631-51. doi:10.1016/s0169-409x(02)00044-3.
Carney, W. P. et al. "Monitoring the circulating levels of the HER2/neu oncoprotein in breast cancer." Clinical breast cancer vol. 5,2 (2004): 105-16. doi:10.3816/cbc.2004.n.014.
Carter, P. "Improving the efficacy of antibody-based cancer therapies." Nature reviews. Cancer vol. 1,2 (2001 ): 118-29. doi:10.1038/35101072.
Chiu, M. L. and Gilliland, G. L. "Engineering antibody therapeutics." Current opinion in structural biology vol. 38 (2016): 163-73. doi:10.1016/j.sbi.2016.07.012.

(56) References Cited

OTHER PUBLICATIONS

Choi, K. Y. et al. "Self-assembled hyaluronic acid nanoparticles for active tumor targeting." Biomaterials vol. 31, 1 (2010): 106-14. doi: 10.1016/j.biomaterials.2009.09.030.
Couvreur, P. and Vauthier, C. "Nanotechnology: intelligent design to treat complex disease." Pharmaceutical research vol. 23, 7 (2006): 1417-50. doi:10.1007/s11095-006-0284-8.
Danczyk, R. et al. "Comparison of antibody functionality using different immobilization methods." Biotechnology and bioengineering vol. 84,2 (2003): 215-23. doi: 10.1002/bit.10760.
Deisenhofer, J. "Crystallographic refinement and atomic models of a human Fe fragment and its complex with fragment B of protein A from *Staphylococcus aureus* at 2.9- and 2.8-A resolution." Biochemistry vol. 20,9 (1981):2361-70.
Delano, W. L. et al. "Convergent solutions to binding at a protein-protein interface." Science (New York, N.Y.) vol. 287,5456 (2000): 1279-83. doi:10.1126/science.287.5456.1279.
Divine et al., "Designed proteins assemble antibodies into modular nanocages" Science 372(6537): eabd994 (2021).
Douglas, T. and Young, M. "Viruses: making friends with old foes." Science (New York, N.Y.) vol. 312,5775 (2006): 873-5. doi:10.1126/science.1123223.
Erathodiyil, N. and Ying, J. Y. "Functionalization of inorganic nanoparticles for bioimaging applications." Accounts of chemical research vol. 44, 10 (2011 ): 925-35. doi: 101021/ar2000327.
Farokhzad, O. C. and Langer, R. "Impact of nanotechnology on drug delivery." ACS nano vol. 3,1 (2009): 16-20. doi: 10.1021 /nn900002m.
Foster, T. J., Geoghegan, J. A., Ganesh, V. K. & Hook, M. Adhesion, invasion and evasion: the many functions of the surface proteins of *Staphylococcus aureus*. Nat. Rev. Microbiol. 12, 49-62 (2014).
Gao, J. et al. "Multifunctional magnetic nanoparticles: design, synthesis, and biomedical applications." Accounts of chemical research vol. 42,8 (2009): 1097-107. doi:10.1021/ar9000026.
Gillies, E. Rand Frech Et, J. M. "Dendrimers and dendritic polymers in drug delivery." Drug discovery today vol. 10, 1 (2005): 35-43. doi:10.1016/S1359-6446(04 )03276-3.
Hain Feld, J. F. "Uranium-loaded apoferritin with antibodies attached: molecular design for uranium neutron-capture therapy." Proceedings of the National Academy of Sciences of the United States of America vol. 89,22 (1992): 11064-8. doi: 10.1073/pnas.89.22.11064.
Hellstrom, I. et al. "Overexpression of HER-2 in ovarian carcinomas." Cancer research vol. 61,6 (2001 ): 2420-3.
Hirsch, L. R. et al. "Metal nanoshells." Annals of biomedical engineering vol. 34, 1 (2006): 15-22. doi: 10.1007/s10439-005-9001-8.
Hong, S. et al. "The binding avidity of a nanoparticle-based multivalent targeted drug delivery platform." Chemistry & biology vol. 14, 1 (2007): 107-15. doi:10.1016/j.chembiol.2006.11.015.
Hook, F., et al. (1998). "Energy Dissipation Kinetics for Protein and Antibody-Antigen Adsorption under Shear Oscillation on a Quartz Crystal Microbalance." Langmuir 14(4): 729-734.
Hsia, Y., et al. (2020). "Hierarchical design of multi-scale protein complexes by combinatorial assembly of oligomeric helical bundle and repeat protein building blocks." bioRxiv: 2020.2007.2027.221333.
Hwang, M. P. et al. "Think modular: a simple apoferritin-based platform for the multifaceted detection of pancreatic cancer." ACS nano vol. 7,9 (2013): 8167-74. doi:10.1021/nn403465a.
Jeong, Y. et al. "Efficient selection of IgG Fe domain-binding peptides fused to fluorescent protein using *E. coli* expression system and dot-blotting assay." Peptides vol. 31,2 (2010): 202-6. doi:10.1016/j.peptides.2009.12.009.
Jølck, R. I. et al. "Engineering liposomes and nanoparticles for biological targeting." Advances in biochemical engineering/biotechnology vol. 125 (2011): 251-80. doi:10.1007/10_2010_92.
Jung, Y. et al. "Controlled antibody immobilization onto immunoanalytical platforms by synthetic peptide." Analytical biochemistry vol. 374, 1 (2008): 99-105. doi: 10.1016/j.ab.2007.10.022.
Kang, S. et al. "Development of bacteriophage p22 as a platform for molecular display: genetic and chemical modifications of the procapsid exterior surface." Chembiochem : a European journal of chemical biology vol. 9,4 (2008): 514-8. doi:10.1002/cbic.200700555.
Kang, S. et al. "Implementation of p22 viral capsids as nanoplatforms." Biomacromolecules vol. 11, 10 (2010): 2804-9. doi:10.1021/bm100877q.
Kang, S. et al. "Janus-like protein cages. Spatially controlled dual-functional surface modifications of protein cages." Nano letters vol. 9,6 (2009): 2360-6. doi:10.1021/n19009028.
Kang, Y. J. et al. "Polyvalent display of monosaccharides on ferritin protein cage nanoparticles for the recognition and binding of cell-surface lectins." Macromolecular bioscience vol. 14,5 (2014 ): 619-25. doi: 10.1002/mabi.201300528.
Kang, Y. J., et al. (2011 ). "Biomimetic FePt nanoparticle synthesis within Pyrococcus furiosus ferritins and their layer-by-layer formation." Soft Matter 7(23): 11078-11081.
Koo, H. et al. "In vivo targeted delivery of nanoparticles for theranosis." Accounts of chemical research vol. 44, 10 (2011): 1018-28. doi:10.1021/ar2000138.
Kwon, C. et al. "Development of protein-cage-based delivery nanoplatforms by polyvalently displaying 13-cyclodextrins on the surface of ferritins through copper(! )-catalyzed azide/alkyne cycloaddition." Macromolecular bioscience vol. 12,11 (2012): 1452-8. doi:10.1002/mabi.201200178.
Leavy, O. Therapeutic antibodies: past, present and future. Nature Rev. Immunol. 10, 297 (2010).
Lee, E. S. et al. "Doxorubicin loaded pH-sensitive polymeric micelles for reversal of resistant MCF-7 tumor." Journal of controlled release : official journal of the Controlled Release Society vol. 103,2 (2005): 405-18. doi: 10.1016/j.jconrel.2004.12.018.
Lee, E. S. et al. "Super pH-sensitive multifunctional polymeric micelle." Nano letters vol. 5,2 (2005): 325-9. doi:10.1021/nl0479987.
Lee, J. et al. "An enhanced ascorbate peroxidase 2/antibody-binding domain fusion protein (APEX2-ABD) as a recombinant target-specific signal amplifier." Chemical communications (Cambridge, England) vol. 51,54 (2015): 10945-8. doi: 10.1039/c5cc02409a.
Lewis, J. D. et al. "Viral nanoparticles as tools for intravital vascular imaging." Nature medicine vol. 12,3 (2006): 354-60. doi:10.1038/nm1368.
Maeda, H. et al. "Tumor vascular permeability and the EPR effect in macromolecular therapeutics: a review." Journal of controlled release : official journal of the Controlled Release Society vol. 65, 1-2 (2000): 271-84. doi:10.1016/so168-3659(99 )00248-5.
Manjappa, A. S. et al. "Antibody derivatization and conjugation strategies: application in preparation of stealth immunoliposome to target chemotherapeutics to tumor." Journal of controlled release : official journal of the Controlled Release Societyvol. 150,1 (2011): 2-22. doi:10.1016/j.jconrel.2010.11.002.
Matsumura, Y. and Maeda, H. "A new concept for macromolecular therapeutics in cancer chemotherapy: mechanism of tumoritropic accumulation of proteins and the antitumor agent smancs." Cancer research vol. 46, 12 Pt 1 (1986): 6387-92.
Min, J. et al. "Development of P22 viral capsid nanocomposites as anti-cancer drug, bortezomib (BTZ), nanoplatforms." Macromolecular bioscience vol. 14,4 (2014 ): 557-64. doi: 10.1002/mabi.201300401.
American Lung Association Scientific and Medical Editorial Review Panel. "Learn About ARDS". American Lung Association, updated Nov. 17, 2022, https://www.lung.org/lung-health-diseases/lung-disease-lookup/ards/learn-about-ards (Accessed May 10, 2023).
Bale et al. "Accurate design of megadalton-scale two-component icosahedral protein complexes". Science 353(6297): 389-394, (Jul. 2016).
Baynes et al. "Role of Arginine in the Stabilization of Proteins against Aggregation". Biochemistry 44(12): 4919-1925, (Mar. 2005).
BCC Research. "Nanotechnology in Medical Applications: The Global Market". BCC Research. Published Apr. 2022.
Brunette et al. "Exploring the repeat protein universe through computational protein design". Nature 528(7583): 580-584, (Dec. 2015).

(56) References Cited

OTHER PUBLICATIONS

Hardin et al. "Acute Respiratory Distress Syndrome (ARDS) in COVID-19 Patients". Massachusetts General Hospital. Advances in Motion. Published Apr. 2, 2020. https://advances.massgeneral.org/research-and-innovation/article.aspx?id=1148 (Accessed May 10, 2023).
Corti et al. "Cross-neutralization of four paramyxoviruses by a human monoclonal antibody". Nature 501(7476): 439-443, (Aug. 2013).
Cuesta et al. "Multivalent antibodies: when design surpasses evolution". Trends Biotechnol. 28, 355-362 (2010).
De Miguel et al. "Onto better TRAILs for cancer treatment". Cell Death Differ. 23(5): 733-47, (Mar. 2016).
Dimaio et al. "Improved low-resolution crystallographic refinement with Phenix and Rosetta". Nat Methods. 10(11): 1102-4, (Sep. 2013).
Dyer et al. "High-throughput SAXS for the characterization of biomolecules in solution: a practical approach". Methods Mol Biol. 1091: 245-258, (2014).
Fallas et al. "Computational design of self-assembling cyclic protein homo-oligomers". Nat Chem 9(4): 353-360, (Dec. 2016).
Graille et al. "Crystal structure of a *Staphylococcus aureus* protein A domain complexed with the Fab fragment of a human IgM antibody: Structural basis for recognition of B-cell receptors and superantigen activity". PNAS 97(10): 6399-404, (May 2000).
Graves et al. Apo2L/TRAIL and the death receptor 5 agonist antibody AMG 655 cooperate to promote receptor clustering and antitumor activity. Cancer Cell. 26, 177-189 (2014).
Greene et al. "Forming next-generation antibody-nanoparticle conjugates through the oriented installation of non-engineered antibody fragments". Chemical Science 9(1): 79-87, (Aug. 2017).
Hiramoto et al. "The IgM pentamer is an asymmetric pentagon with an open groove that binds the AIM protein". Sci. Adv. 4(10): eaau1199 (Oct. 2018).
Hsia et al. "Design of multi-scale protein complexes by hierarchical building block fusion". Nature 12(1):2294, (Apr. 2021).
Huang et al. "High thermodynamic stability of parametrically designed helical bundles". Science 346(6208): 481-485, (Oct. 2014).
Idusogie et al. "Mapping of the C1q Binding Site on Rituxan, a Chimeric Antibody with aHuman IgG1 Fc". J Immunol. 164(8): 4178-4184, (Apr. 2000).
Jendeberg et al. "Engineering of Fc(1) and Fc(3) from human immunoglobulin G to analyse subclass specificity for staphylococcal protein A". J Immunol Methods. 201(1): 25-34, (Fe 1997).
Jiang et al. "Combined delivery of angiopoietin-1 gene and simvastatin mediated by anti-intercellular adhesion molecule-1 antibody-conjugated ternary nanoparticles for acute lung injury therapy". Nanomedicine: Nanotechnology, Biology and Medicine 15(1): 25-36, (Jan. 2019).
Johnston et al. "DR5-targeted, chemotherapeutic drug-loaded nanoparticles induce apoptosis and tumor regression in pancreatic cancer in vivo models". Journal of Controlled Release 324: 610-619, (Aug. 2020).
Kim et al. "The ABCs of artificial antigen presentation". Nature Biotechnology 22(4): 403-410, (Apr. 2004).
Kang et al. "Developing an antibody-binding protein cage as a molecular recognition drug modular nanoplatform". Biomaterials. 33(21): 5423-5430 (Apr. 2012).
Kim et al. "Development of an antibody-binding modular nanoplatform for antibody-guided targeted cell imaging and delivery". RSC Advances. 6(23): 19208-19213 (Feb. 2016).
King et al. "Computational Design of Self-Assembling Protein Nanomaterials with Atomic Level Accuracy". Science 336(6085): 1171-1174 (Jun. 2012).
Klement et al. "Antibody engineering of a cytotoxic monoclonal antibody 84 againsthuman embryonic stem cells: Investigating the effects of multivalency on cytotoxicity". Journal of Biotechnology 243: 29-37 (Dec. 2016).
Kornbluth et al., "Design of CD40 Agonists and their use in growing B cells for cancer immunotherapy". Int Rev Immunol. 31(4): 10.3109/08830185.2012.703272., (Aug. 2012).
Laursen et al. "Universal Protection against Influenza Infection by a Multi-Domain Antibody to Influenza Hemagglutinin". Science 362(6414): 598-602, (Nov. 2018).
Leman et al. "Macromolecular modeling and design in Rosetta: recent methods and frameworks". Nat Methods. 17(7): 665-680, (Jul. 2020).
Leppanen et al. "Structural basis of Tie2 activation and Tie2/Tiel heterodimerization". Proc. Natl. Acad. Sci. U. S. A 114, 4376-4381 (2017).
Lu et al. "Development of therapeutic antibodies for the treatment of diseases". J. Biomed. Sci. 27(1): 1, (Jan. 2020).
Mayo Clinic Staff. "Sepsis". Mayo Clinic. Published Feb. 10, 2023. https://www.mayoclinic.org/diseases-conditions/sepsis/symptoms-causes/syc-20351214#:%7E:text=Sepsis%20is%20a%20potentially%20life,can%20damage%20multiple%20organ%20systems. (accesses May 10, 2023).
Miller et al. ""Multimeric antibodies with increased valency surpassing functional affinity and potency thresholds using novel formats"". MABS 12(1): e1752529-1-e1752529-11, (Apr. 2020).
Mohan et al. "Topological control of cytokine receptor signaling induces differential effects in hematopoiesis". Science. 364 (2019), doi: 10. I 126/science.aav7532.
Naval et al. "Importance of TRAIL Molecular Anatomy in Receptor Oligomerization and Signaling. Implications for Cancer Therapy". Cancers (Basel) 11(4): 444, (Mar. 2019).
Nunez-Prado et al. "The coming of age of engineered multivalent antibodies". Drug Discovery Today. 20 (2015), pp. 588-594.
Parikh. "Dysregulation of the angiopoietin-Tie-2 axis in sepsis and ARDS". Virulence 4(6): 517-524, (May 2013).
Riley et al. "Frizzled7 Antibody-Functionalized Nanoshells EnableMultivalent Binding for Wnt Signaling Inhibition inTriple Negative Breast Cancer Cells". Small 13(26): 10.1002/smll.201700544 (May 2017).
Seifert et al. "Tetravalent Antibody-scTRAIL Fusion Proteins withImproved Properties". Mol Cancer Ther. 13(1): 101-11, (Oct. 2013).
Schneidman-Duhovny et al. "Accurate SAXS Profile Computation and its Assessment by Contrast Variation Experiments". Biophys J. 105(4): 962-974, (Aug. 2013).
Siegemund et al. "IgG-single-chain TRAIL fusionproteins for tumour therapy". Science Reports 8(7808): 1-11, (May 2018).
Steenblock et al. "Antigen presentation on artificial acellular substrates: modular systems for flexible, adaptable immunotherapy". Expert Opin Biol Ther. 9(4): 451-464, (Apr. 2009).
Studier et al. "Protein production by auto-induction in high-density shaking cultures". Protein Expr Purif. 41(1): 207-234, (May 2005).
Taupin et al. "Identification of agonistic and antagonistic antibodies against gp 190, the leukemia inhibitory factor receptor, reveals distinct roles for its two cytokine-binding domains". J. Biol. Chem. 276, 47975-47981 (2001).
Tuthill et al., "TRAIL-R2-specific antibodies and recombinant TRAIL can synergise to kill cancer cells". Oncogene 34(16): 2138-2144, (Jun. 2014).
Ueda et al. "Tailored design of protein nanoparticle scaffolds for multivalent presentation of viral glycoprotein antigens". Elife 9: e57659, (Aug. 2020).
Vonderheide et al. "Agonistic CD40 antibodies and cancer therapy". Clin Cancer Res. 19(5): 1035-1043, (Sep. 2013).
Vulovic et al. "Generation of ordered protein assemblies using rigid three-body fusion". PNAS 118(23): e2015037118, (Jun. 2021).
Yeates et al. "The design of symmetric protein nanomaterials comesof age in theory and practice". Curr Opin Struct Biol. 39: 134-143, (Jul. 2016).
Park, et al., (Apr. 2009) "A highly sensitive and selective diagnostic assay based on virus nanoparticles," Nature Nanotechnology, 4: 259-264.
Bhattacharya et al. Impact of genetic variation on three dimensional structure and function of proteins. PLoS ONE 12 (3): e0171355, 2017.

(56) References Cited

OTHER PUBLICATIONS

Bork, P. Powers and pitfalls in sequence analysis: the 70% hurdle. Genome Res 10: 398-400, 2000.
Bork, P. Go hunting in sequence databases but watch out for the traps. Trends in Genetics 12(10): 425-427, 1996.
Brenner. S.E. Errors in genome annotation. Trends in Genetics 15:132-133, 1999.
Doerks et al. Protein annotation: detective work for function prediction. Trends in Genetics 14:248-250, 1998.
Fenton et al. Rheostat positions: a new classification of protein positions relevant to pharmacogenomics. Medicinal Chem Res 29: 1133-1146, 2020.
Fleishman et al. (2011). RosettaScripts: a scripting language interface to the Rosetta macromolecular modeling suite. PLoS One 6: e20161, 10 pages.
Guo et al. Protein tolerance to random amino acid change. Proc Natl Acad Sci USA 101 (25): 9205-9210, 2004.
Huang et al. (2016). "The coming of age of de novo protein design." Nature 537: 320-327.
Jansson et al. (1998). "All individual domains of staphylococcal protein A show Fab binding." FEMS Immunol. Med. Microbiol. 20: 69-78.
King et al. (2014). "Accurate design of co-assembling multicomponent protein nanomaterials." Nature 510: 103-108.
Koga et al. (2012). "Principles for designing ideal protein structures." Nature 491: 222-227.
Ngo et al. "Computational complexity, protein structure prediction, and the Levinthal paradox" in The Protein Folding Problem and Tertiary Structure Prediction, pp. 492-495, 1994.
Silva et al. (2016). Motif-driven Design of Protein-Protein Interactions. Methods Mol. Biol. 1414: 285-304.
Skolnick et al. From genes to protein structure and function: novel applications of computational approaches in the genomic era. Trends Biotechnol 18(1):34-39 2000.
Smith et al. The challenges of genome sequence annotation or "the devil is in the details". Nature Biotechnol 15: 1222-1223, 1997.
Tokuriki et al. Stability effects of mutations and protein evolvability. Curr Opin Structural Biol 19: 596-604, 2009.
Ultsch et al. (2017). "3-2-1: Structural insights from stepwise shrinkage of a three-helix Fc-binding domain to a single helix." Protein Eng. Des. Sel. 30: 619-625.
Wells, J.A. Additivity of mutational effects in proteins. Biochemistry 29(37): 8509-8517, 1990.

* cited by examiner

| Target | $K_D$ (M) | $K_D$ Error | $k_{on}$ (1/Ms) | $k_{on}$ Error | $k_{dis}$ (1/s) | $k_{dis}$ Error |
|---|---|---|---|---|---|---|
| Fc | 1.13E-07 | 7.69E-09 | 7.30E+05 | 4.74E+04 | 8.25E-02 | 1.68E-03 |
| IgG1 | 7.17E-08 | 1.24E-09 | 5.44E+05 | 9.03E+03 | 3.90E-02 | 1.92E-04 |

SEQUENCE LISTING

```
<160> NUMBER OF SEQ ID NOS: 56

<210> SEQ ID NO 1
<211> LENGTH: 364
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (355)..(364)
<223> OTHER INFORMATION: optionally absent

<400> SEQUENCE: 1

Met Ser Asp Glu Glu Glu Arg Asn Glu Leu Ile Lys Arg Ile Arg Glu
1               5                   10                  15

Ala Ala Gln Arg Ala Arg Glu Ala Ala Glu Arg Thr Gly Asp Pro Arg
            20                  25                  30

Val Arg Glu Leu Ala Arg Glu Leu Ala Arg Ile Ala Gln Ile Ala Phe
        35                  40                  45

Tyr Leu Val Leu His Asp Pro Ser Ser Ser Glu Val Asn Glu Ala Leu
    50                  55                  60

Lys Ala Val Val Lys Ala Ile Glu Leu Ala Val Arg Ala Leu Glu Glu
65                  70                  75                  80

Ala Glu Lys Thr Gly Asp Pro Glu Val Arg Glu Leu Ala Arg Glu Val
                85                  90                  95

Val Arg Leu Ala Val Glu Val Ala Thr Ala Thr Ala Ala Gly Glu Asn
            100                 105                 110

Asp Thr Leu Arg Lys Val Ala Glu Arg Ala Leu Arg Leu Ala Lys Glu
        115                 120                 125

Ala Ala Lys Arg Gly Asp Ala Lys Ala Ala Lys Gln Ala Ala Lys Ile
    130                 135                 140

Ala Lys Leu Ala Ala Ala Asn Ala Gly Asp Glu Asp Val Leu Lys Lys
145                 150                 155                 160

Val Glu Leu Val Arg Leu Ala Ile Glu Leu Val Glu Ile Val Val Glu
                165                 170                 175

Asn Ala Lys Arg Lys Gly Asp Asp Asp Lys Glu Ala Ala Glu Ala Ala
            180                 185                 190
```

```
Leu Ala Ala Phe Arg Ile Val Leu Ala Ala Ala Gln Leu Ala Gly Ile
        195                 200                 205

Ala Ser Leu Glu Val Leu Glu Leu Ala Leu Arg Leu Ile Lys Glu Val
    210                 215                 220

Val Glu Asn Ala Gln Arg Glu Gly Tyr Asp Ile Ala Val Ala Ala Ile
225                 230                 235                 240

Ala Ala Ala Val Ala Phe Ala Val Val Ala Val Ala Ala Ala Ala Ala
                245                 250                 255

Asp Ile Thr Ser Ser Glu Val Leu Glu Leu Ala Ile Arg Leu Ile Lys
            260                 265                 270

Glu Val Val Glu Asn Ala Gln Arg Glu Gly Tyr Val Ile Leu Leu Ala
        275                 280                 285

Ala Leu Ala Ala Ala Ala Ala Phe Val Val Val Ala Ala Ala Ala Lys
    290                 295                 300

Arg Ala Gly Ile Thr Ser Ser Glu Thr Leu Lys Arg Ala Ile Glu Glu
305                 310                 315                 320

Ile Arg Lys Arg Val Glu Glu Ala Gln Arg Glu Gly Asn Asp Ile Ser
                325                 330                 335

Glu Ala Ala Arg Gln Ala Ala Glu Glu Phe Arg Lys Lys Ala Glu Glu
            340                 345                 350

Leu Lys Gly Ser Leu Glu His His His His His His
        355                 360


<210> SEQ ID NO 2
<211> LENGTH: 364
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (355)..(364)
<223> OTHER INFORMATION: optionally absent

<400> SEQUENCE: 2

Met Ser Asp Glu Glu Glu Arg Asn Glu Leu Ile Lys Arg Ile Arg Glu
1               5                   10                  15

Ala Ala Gln Arg Ala Arg Glu Ala Ala Glu Arg Thr Gly Asp Pro Arg
            20                  25                  30

Val Arg Glu Leu Ala Arg Glu Leu Ala Arg Ile Ala Gln Ile Ala Phe
        35                  40                  45

Tyr Leu Val Leu His Asp Pro Ser Ser Ser Glu Val Asn Glu Ala Leu
    50                  55                  60

Lys Ala Val Val Lys Ala Ile Glu Leu Ala Val Arg Ala Leu Glu Ala
65                  70                  75                  80

Ala Glu Lys Thr Gly Asp Pro Arg Val Arg Glu Leu Ala Arg Glu Val
                85                  90                  95

Val Lys Ala Ala Val Asp Val Ala Glu Ala Ala Gln Ala Gly Leu Asn
            100                 105                 110

Asp Lys Leu Arg Glu Val Ala Glu Lys Ala Leu Arg Leu Ala Lys Glu
        115                 120                 125

Ala Leu Lys Glu Gly Asp Ser Thr Ala Ala Glu Leu Ala Ala Glu Ile
    130                 135                 140

Ala Arg Leu Ala Ala Lys Leu Ala Gly Asp Glu Asp Val Leu Lys Lys
```

145 150 155 160

Val Lys Leu Val Leu Glu Ala Ile Lys Leu Val Lys Ile Val Val Glu
165 170 175

Asn Ala Lys Arg Lys Gly Asp Asp Ser Lys Glu Ala Ala Glu Ala Ala
180 185 190

Val Ala Ala Phe Leu Ile Val Leu Ala Ala Ala Lys Leu Ala Gly Ile
195 200 205

Ala Ser Glu Glu Val Leu Glu Leu Ala Ala Arg Leu Ile Lys Glu Val
210 215 220

Val Glu Asn Ala Gln Arg Glu Gly Tyr Asp Ile Ala Val Ala Ala Ile
225 230 235 240

Ala Ala Ala Val Ala Phe Ala Val Val Ala Val Ala Ala Ala Ala Ala
245 250 255

Asp Ile Thr Ser Ser Glu Val Leu Glu Leu Ala Ile Arg Leu Ile Lys
260 265 270

Glu Val Val Glu Asn Ala Gln Arg Glu Gly Tyr Val Ile Leu Leu Ala
275 280 285

Ala Leu Ala Ala Ala Ala Ala Phe Val Val Val Ala Ala Ala Ala Lys
290 295 300

Arg Ala Gly Ile Thr Ser Ser Glu Thr Leu Lys Arg Ala Ile Glu Glu
305 310 315 320

Ile Arg Lys Arg Val Glu Glu Ala Gln Arg Glu Gly Asn Asp Ile Ser
325 330 335

Glu Ala Ala Arg Gln Ala Ala Glu Glu Phe Arg Lys Lys Ala Glu Glu
340 345 350

Leu Lys Gly Ser Leu Glu His His His His His His
355 360

<210> SEQ ID NO 3
<211> LENGTH: 381
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (372)..(381)
<223> OTHER INFORMATION: optionally absent

<400> SEQUENCE: 3

Met Ser Asp Glu Glu Glu Arg Asn Glu Leu Ile Lys Arg Ile Arg Glu
1 5 10 15

Ala Ala Gln Arg Ala Arg Glu Ala Ala Glu Arg Thr Gly Asp Pro Arg
20 25 30

Val Arg Glu Leu Ala Arg Glu Leu Ala Lys Leu Ala Gln Ile Ala Phe
35 40 45

Tyr Leu Val Leu His Asp Pro Ser Ala Lys Glu Val Asn Leu Ala Leu
50 55 60

Glu Leu Ile Val Lys Ala Ile Glu Leu Ala Val Arg Ala Leu Glu Glu
65 70 75 80

Ala Glu Lys Thr Gly Asp Pro His Ala Arg Glu Leu Ala Arg Glu Ile
85 90 95

Val Arg Leu Ala Val Glu Leu Ala Arg Ala Val Ala Glu Ala Ala Glu
100 105 110

```
Glu Ala Lys Lys Gln Gly Asn Ser Glu Leu Ala Glu Gln Val Ala Arg
        115                 120                 125

Ala Ala Gln Val Ala Leu Glu Val Ile Lys Ala Ala Ile Thr Ala Ala
    130                 135                 140

Lys Gln Gly Asp Arg Lys Ala Phe Arg Ala Ala Leu Glu Leu Val Leu
145                 150                 155                 160

Glu Val Ile Lys Ala Ile Glu Glu Ala Val Lys Gln Gly Asn Pro Lys
                165                 170                 175

Lys Val Ala Glu Val Ala Leu Lys Ala Glu Leu Ile Arg Ile Val Val
            180                 185                 190

Gln Asn Ala Ala Asn Lys Gly Asp Asp Ala Asp Glu Ala Val Glu Ala
        195                 200                 205

Ala Arg Ala Ala Phe Glu Ile Val Leu Ala Ala Ala Gln Leu Ala Gly
    210                 215                 220

Ile Asp Ser Glu Glu Val Leu Glu Leu Ala Ala Arg Leu Ile Lys Glu
225                 230                 235                 240

Val Val Glu Asn Ala Gln Arg Glu Gly Tyr Asp Ile Ala Val Ala Ala
                245                 250                 255

Ile Ala Ala Ala Val Ala Phe Ala Val Val Ala Val Ala Ala Ala Ala
            260                 265                 270

Ala Asp Ile Thr Ser Ser Glu Val Leu Glu Leu Ala Ile Arg Leu Ile
        275                 280                 285

Lys Glu Val Val Glu Asn Ala Val Arg Glu Gly Tyr Val Ile Leu Leu
    290                 295                 300

Ala Ala Leu Ala Ala Ala Ala Ala Phe Val Val Val Ala Ala Ala Ala
305                 310                 315                 320

Lys Arg Ala Gly Ile Thr Ser Ser Glu Thr Leu Lys Arg Ala Ile Glu
                325                 330                 335

Glu Ile Arg Lys Arg Val Glu Glu Ala Gln Arg Glu Gly Asn Asp Ile
            340                 345                 350

Ser Glu Ala Ala Arg Gln Ala Ala Glu Glu Phe Arg Lys Lys Ala Glu
        355                 360                 365

Glu Leu Lys Gly Ser Leu Glu His His His His His His
    370                 375                 380
```

<210> SEQ ID NO 4
<211> LENGTH: 363
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (354)..(363)
<223> OTHER INFORMATION: optionally absent

<400> SEQUENCE: 4

```
Met Phe Asn Lys Ser Gln Gln Ser Ala Phe Tyr Leu Ile Leu Asn Met
1               5                   10                  15

Pro Asn Leu Asn Glu Ala Gln Arg Asn Gly Phe Ile Gln Ser Leu Lys
            20                  25                  30

Asp Asp Pro Ala Lys Ser Glu Val Val Ala Gly Glu Ala Ala Ile Glu
        35                  40                  45
```

```
Ala Ala Arg Asn Ala Ser Lys Lys Gly Ser Pro Glu Thr Ala Arg Glu
    50                  55                  60

Ala Val Arg Leu Ala Leu Glu Leu Val Gln Glu Ala Ala Arg Val Ala
65                  70                  75                  80

Arg Lys Thr Gly Ser Thr Glu Leu Leu Ile Ala Ala Ala Lys Leu Ala
                85                  90                  95

Ile Glu Val Ala Arg Val Ala Leu Lys Val Gly Ser Pro Glu Ala Ala
            100                 105                 110

Arg Glu Ala Val Arg Ala Ala Leu Glu Leu Val Gln Glu Leu Ile Arg
        115                 120                 125

Ala Ala Arg Lys Thr Gly Ser Lys Glu Val Leu Glu Glu Ala Ala Lys
    130                 135                 140

Leu Ala Leu Glu Val Ala Leu Val Ala Ala Ala Val Gly Ser Ser Glu
145                 150                 155                 160

Ala Ala Ala Lys Ala Val Ala Thr Ala Val Glu Ala Leu Lys Glu Ala
                165                 170                 175

Gly Ala Ser Glu Asp Glu Ile Ala Glu Ile Val Ala Arg Val Ile Ser
            180                 185                 190

Glu Val Ile Arg Ile Leu Lys Glu Asn Gly Ser Glu Tyr Lys Val Ile
        195                 200                 205

Cys Val Ser Val Ala Lys Ile Val Ala Glu Ile Val Glu Ala Leu Lys
    210                 215                 220

Arg Ser Gly Thr Ser Glu Asp Glu Ile Ala Glu Ile Val Ala Arg Val
225                 230                 235                 240

Ile Ser Glu Val Ile Arg Thr Leu Lys Glu Ser Gly Ser Asp Tyr Leu
                245                 250                 255

Ile Ile Cys Val Cys Val Ala Ile Ile Val Ala Glu Ile Val Glu Ala
            260                 265                 270

Leu Lys Arg Ser Gly Thr Ser Glu Asp Glu Ile Ala Glu Ile Val Ala
        275                 280                 285

Arg Val Ile Ser Glu Val Ile Arg Thr Leu Lys Glu Ser Gly Ser Ser
    290                 295                 300

Tyr Glu Val Ile Lys Glu Cys Val Gln Ile Ile Val Leu Ala Ile Ile
305                 310                 315                 320

Leu Ala Leu Met Lys Ser Gly Thr Glu Val Glu Glu Ile Leu Leu Ile
                325                 330                 335

Leu Leu Arg Val Lys Thr Glu Val Arg Arg Thr Leu Lys Glu Ser Gly
            340                 345                 350

Ser Gly Ser Leu Glu His His His His His His
        355                 360


<210> SEQ ID NO 5
<211> LENGTH: 361
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (352)..(361)
<223> OTHER INFORMATION: optionally absent

<400> SEQUENCE: 5

Met Phe Asn Lys Ser Gln Gln Ser Ala Phe Tyr Leu Ile Leu Asn Met
```

```
1               5                   10                  15

Pro Asn Leu Asn Glu Ala Gln Arg Asn Gly Phe Ile Gln Ser Leu Lys
            20                  25                  30

Asp Asp Pro Ser Lys Ser Glu Val Val Ala Gly Glu Ala Ala Ile Glu
        35                  40                  45

Ala Ala Arg Asn Ala Leu Lys Lys Gly Ser Pro Glu Thr Ala Arg Glu
    50                  55                  60

Ala Val Arg Leu Ala Leu Glu Leu Val Gln Glu Ala Glu Arg Gln Ala
65                  70                  75                  80

Arg Lys Thr Gly Ser Thr Glu Arg Leu Ile Ala Ala Ala Lys Leu Ala
                85                  90                  95

Ile Glu Val Ala Arg Val Ala Leu Lys Val Gly Ser Pro Glu Thr Ala
            100                 105                 110

Arg Glu Ala Val Arg Thr Ala Leu Glu Leu Val Gln Glu Leu Ile Arg
        115                 120                 125

Gln Ala Arg Lys Thr Gly Ser Lys Glu Val Leu Glu Glu Ala Ala Lys
    130                 135                 140

Leu Ala Leu Glu Val Ala Lys Val Ala Ala Glu Val Gly Ser Pro Glu
145                 150                 155                 160

Thr Ala Ala Arg Ala Val Ala Thr Ala Val Glu Ala Leu Lys Glu Ala
                165                 170                 175

Gly Ala Ser Glu Asp Glu Ile Ala Glu Ile Val Ala Arg Val Ile Ser
            180                 185                 190

Glu Val Ile Arg Ile Leu Lys Glu Ser Gly Ser Glu Tyr Lys Val Ile
        195                 200                 205

Cys Arg Ala Val Ala Arg Ile Val Ala Glu Ile Val Glu Ala Leu Lys
    210                 215                 220

Arg Ser Gly Thr Ser Glu Asp Glu Ile Ala Glu Ile Val Ala Arg Val
225                 230                 235                 240

Ile Ser Glu Val Ile Arg Thr Leu Lys Glu Ser Gly Ser Asp Tyr Leu
                245                 250                 255

Ile Ile Cys Val Cys Val Ala Ile Ile Val Ala Glu Ile Val Glu Ala
            260                 265                 270

Leu Lys Arg Ser Gly Thr Ser Glu Asp Glu Ile Ala Glu Ile Val Ala
        275                 280                 285

Arg Val Ile Ser Glu Val Ile Arg Thr Leu Lys Glu Ser Gly Ser Ser
    290                 295                 300

Tyr Glu Val Ile Lys Glu Cys Val Gln Ile Ile Val Leu Ala Ile Ile
305                 310                 315                 320

Leu Ala Leu Met Lys Ser Gly Thr Glu Val Glu Glu Ile Leu Leu Ile
                325                 330                 335

Leu Leu Arg Val Lys Thr Glu Val Arg Arg Thr Leu Lys Glu Ser Gly
            340                 345                 350

Ser Leu Glu His His His His His His
        355                 360


<210> SEQ ID NO 6
<211> LENGTH: 314
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
```

<220> FEATURE:
<221> NAME/KEY: MISC_FEATURE
<222> LOCATION: (305)..(314)
<223> OTHER INFORMATION: optionally absent

<400> SEQUENCE: 6

```
Met Phe Asn Lys Asp Gln Gln Ser Ala Phe Tyr Glu Val Leu Asn Met
1               5                   10                  15

Pro Asn Leu Asn Glu Ala Gln Arg Asn Gly Phe Ile Gln Ser Leu Lys
            20                  25                  30

Asp Asp Pro Ser Gln Ser Leu Lys Ile Leu Ile Lys Ala Ala Ala Gly
        35                  40                  45

Gly Asp Ser Glu Leu Glu Glu Val Ala Lys Arg Ile Val Lys Glu Leu
    50                  55                  60

Ala Glu Gln Gly Arg Ser Glu Lys Glu Ala Ala Lys Glu Ala Ala Glu
65                  70                  75                  80

Leu Ile Glu Arg Ile Thr Arg Ala Ala Gly Gly Asn Ser Asp Leu Ile
                85                  90                  95

Glu Leu Ala Val Arg Ile Val Lys Ile Leu Glu Glu Gln Gly Arg Ser
            100                 105                 110

Pro Ser Glu Ala Ala Lys Glu Ala Val Glu Ala Ile Glu Ala Ile Val
        115                 120                 125

Arg Ala Ala Gly Gly Asp Ser Glu Ala Ile Lys Val Ala Ala Glu Ile
    130                 135                 140

Ala Lys Thr Ile Ile Thr Gln Lys Glu Ser Gly Ser Glu Tyr Lys Glu
145                 150                 155                 160

Ile Cys Arg Thr Val Ala Arg Ile Val Ala Glu Ile Val Glu Lys Leu
                165                 170                 175

Lys Arg Asn Gly Ala Ser Glu Asp Glu Ile Ala Glu Ile Val Ala Ala
            180                 185                 190

Ile Ile Ala Ala Val Ile Leu Thr Leu Lys Leu Ser Gly Ser Asp Tyr
        195                 200                 205

Leu Ile Ile Cys Val Cys Val Ala Ile Ile Val Ala Glu Ile Val Glu
    210                 215                 220

Ala Leu Lys Arg Ser Gly Thr Ser Glu Asp Glu Ile Ala Glu Ile Val
225                 230                 235                 240

Ala Arg Val Ile Ser Ala Val Ile Arg Val Leu Lys Glu Ser Gly Ser
                245                 250                 255

Ser Tyr Glu Val Ile Lys Glu Cys Val Gln Ile Ile Val Leu Ala Ile
            260                 265                 270

Ile Leu Ala Leu Met Lys Ser Gly Thr Glu Val Glu Glu Ile Leu Leu
        275                 280                 285

Ile Leu Leu Arg Val Lys Thr Glu Val Arg Arg Thr Leu Lys Glu Ser
    290                 295                 300

Gly Ser Leu Glu His His His His His His
305                 310
```

<210> SEQ ID NO 7
<211> LENGTH: 422
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:

<221> NAME/KEY: MISC_FEATURE
<222> LOCATION: (413)..(422)
<223> OTHER INFORMATION: optionally absent

<400> SEQUENCE: 7

```
Met Phe Asn Lys Asp Gln Gln Ser Ala Phe Tyr Glu Ile Leu Asn Met
1               5                   10                  15

Pro Asn Leu Asn Glu Ala Leu Arg Asn Gly Phe Ile Gln Leu Leu Lys
            20                  25                  30

Asp Asp Pro Ser Lys Ser Thr Val Ile Leu Thr Ala Ala Lys Val Ala
        35                  40                  45

Ala Glu Leu Ser Glu Lys Ile Arg Thr Leu Lys Glu Ser Gly Ser Ser
    50                  55                  60

Tyr Glu Gln Ile Ala Glu Thr Val Ala Lys Ala Val Ala Lys Leu Val
65                  70                  75                  80

Glu Lys Leu Lys Arg Asn Gly Val Ser Glu Asp Glu Ile Ala Leu Ala
                85                  90                  95

Val Ala Leu Ile Ile Ser Ala Val Ile Gln Thr Leu Lys Glu Ser Gly
            100                 105                 110

Ser Ser Tyr Glu Val Ile Ala Glu Ile Val Ala Arg Ile Val Ala Glu
        115                 120                 125

Ile Val Glu Ala Leu Lys Arg Ser Gly Thr Ser Glu Asp Glu Ile Ala
    130                 135                 140

Glu Ile Val Ala Arg Val Ile Ser Glu Val Ile Arg Thr Leu Lys Glu
145                 150                 155                 160

Ser Gly Ser Ser Tyr Glu Val Ile Ala Glu Ile Val Ala Arg Ile Val
                165                 170                 175

Ala Glu Ile Val Glu Ala Leu Lys Arg Ser Gly Thr Ser Glu Asp Glu
            180                 185                 190

Ile Ala Lys Ile Val Ala Arg Val Ile Ala Glu Val Leu Arg Thr Leu
        195                 200                 205

Lys Glu Ser Gly Ser Ser Glu Glu Val Ile Lys Glu Ile Val Ala Arg
    210                 215                 220

Ile Ile Thr Glu Ile Lys Glu Ala Leu Lys Arg Ser Gly Thr Ser Glu
225                 230                 235                 240

Asp Glu Ile Glu Leu Ile Thr Leu Met Ile Glu Ala Ala Leu Glu Ile
                245                 250                 255

Ala Lys Leu Lys Ser Ser Gly Ser Glu Tyr Glu Glu Ile Cys Glu Asp
            260                 265                 270

Val Ala Arg Arg Ile Ala Glu Leu Val Glu Lys Leu Lys Arg Asp Gly
        275                 280                 285

Thr Ser Ala Val Glu Ile Ala Lys Ile Val Ala Ala Ile Ile Ser Ala
    290                 295                 300

Val Ile Ala Met Leu Lys Ala Ser Gly Ser Ser Tyr Glu Val Ile Cys
305                 310                 315                 320

Glu Cys Val Ala Arg Ile Val Ala Glu Ile Val Glu Ala Leu Lys Arg
                325                 330                 335

Ser Gly Thr Ser Ala Ala Ile Ile Ala Leu Ile Val Ala Leu Val Ile
            340                 345                 350

Ser Glu Val Ile Arg Thr Leu Lys Glu Ser Gly Ser Ser Phe Glu Val
        355                 360                 365

Ile Leu Glu Cys Val Ile Arg Ile Val Leu Glu Ile Ile Glu Ala Leu
    370                 375                 380

Lys Arg Ser Gly Thr Ser Glu Gln Asp Val Met Leu Ile Val Met Ala
```

```
385                 390                 395                 400

Val Leu Leu Val Val Leu Ala Thr Leu Gln Leu Ser Gly Ser Leu Glu
                405                 410                 415

His His His His His His
            420


<210> SEQ ID NO 8
<211> LENGTH: 355
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (346)..(355)
<223> OTHER INFORMATION: optionally absent

<400> SEQUENCE: 8

Met Ser Asp Glu Glu Glu Arg Asn Glu Leu Ile Lys Arg Ile Arg Glu
1               5                   10                  15

Ala Ala Gln Arg Ala Arg Glu Ala Ala Glu Arg Thr Gly Asp Pro Arg
            20                  25                  30

Val Arg Glu Leu Ala Arg Glu Leu Ala Arg Leu Ala Gln Arg Ala Phe
        35                  40                  45

Tyr Leu Val Leu His Asp Pro Ser Ser Ser Asp Val Asn Glu Ala Leu
    50                  55                  60

Lys Leu Ile Val Glu Ala Ile Glu Ala Ala Val Arg Ala Leu Glu Ala
65                  70                  75                  80

Ala Glu Arg Ala Gly Asp Pro Glu Leu Arg Glu Asp Ala Arg Glu Ala
                85                  90                  95

Val Arg Leu Ala Val Glu Ala Ala Glu Glu Val Gln Arg Asn Pro Ser
            100                 105                 110

Ser Ser Thr Ala Asn Leu Leu Leu Lys Ala Ile Val Ala Leu Ala Glu
        115                 120                 125

Ala Leu Ala Ala Ala Ala Asn Gly Asp Lys Glu Lys Phe Lys Lys Ala
    130                 135                 140

Ala Glu Ser Ala Leu Glu Ile Ala Lys Arg Val Val Glu Val Ala Ser
145                 150                 155                 160

Lys Glu Gly Asp Pro Glu Ala Val Leu Glu Ala Ala Lys Val Ala Leu
                165                 170                 175

Arg Val Ala Glu Leu Ala Ala Lys Asn Gly Asp Lys Glu Val Phe Lys
            180                 185                 190

Lys Ala Ala Glu Ser Ala Leu Glu Val Ala Lys Arg Leu Val Glu Val
        195                 200                 205

Ala Ser Lys Glu Gly Asp Pro Glu Leu Val Leu Glu Ala Ala Lys Val
    210                 215                 220

Ala Leu Arg Val Ala Glu Leu Ala Ala Lys Asn Gly Asp Lys Glu Val
225                 230                 235                 240

Phe Gln Lys Ala Ala Ala Ser Ala Val Glu Val Ala Leu Arg Leu Thr
                245                 250                 255

Glu Val Ala Ser Lys Glu Gly Asp Ser Glu Leu Glu Thr Glu Ala Ala
            260                 265                 270

Lys Val Ile Thr Arg Val Arg Glu Leu Ala Ser Lys Gln Gly Asp Ala
        275                 280                 285
```

Ala Val Ala Ile Leu Ala Glu Thr Ala Glu Val Lys Leu Glu Ile Glu
    290                 295                 300

Glu Ser Lys Lys Arg Pro Gln Ser Glu Ser Ala Lys Asn Leu Ile Leu
305                 310                 315                 320

Ile Met Gln Leu Leu Ile Asn Gln Ile Arg Leu Leu Val Leu Gln Ile
                325                 330                 335

Arg Met Leu Asp Glu Gln Arg Gln Glu Gly Ser Leu Glu His His His
            340                 345                 350

His His His
        355

<210> SEQ ID NO 9
<211> LENGTH: 364
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (355)..(364)
<223> OTHER INFORMATION: optionally absent

<400> SEQUENCE: 9

Met Ser Asp Glu Glu Glu Arg Asn Glu Leu Ile Lys Arg Ile Arg Glu
1               5                   10                  15

Ala Ala Gln Arg Ala Arg Glu Ala Ala Glu Arg Thr Gly Asp Pro Arg
            20                  25                  30

Val Arg Glu Leu Ala Arg Glu Leu Ala Arg Leu Ala Gln Arg Ala Phe
        35                  40                  45

Tyr Leu Val Leu His Asp Pro Ser Ser Ser Asp Val Asn Glu Ala Leu
    50                  55                  60

Lys Leu Ile Val Glu Ala Ile Glu Ala Ala Val Arg Ala Leu Glu Ala
65                  70                  75                  80

Ala Glu Arg Thr Gly Asp Pro Lys Val Arg Glu Glu Ala Arg Glu Leu
                85                  90                  95

Val Arg Arg Ala Val Glu Ala Ala Glu Glu Val Gln Arg Asn Pro Ser
            100                 105                 110

Ser Ser Glu Val Asn Glu Lys Leu Lys Ala Ile Val Val Glu Ile Glu
        115                 120                 125

Val Lys Val Ala Ser Leu Glu Ala Lys Glu Val Thr Asp Pro Asp Lys
    130                 135                 140

Ala Leu Lys Ile Ala Lys Lys Val Ile Glu Leu Ala Leu Glu Ala Val
145                 150                 155                 160

Lys Glu Asn Pro Ser Thr Glu Ala Leu Arg Ala Val Leu Glu Ala Val
                165                 170                 175

Arg Leu Ala Ser Glu Val Ala Lys Arg Val Thr Asp Pro Asp Lys Ala
            180                 185                 190

Leu Lys Ile Ala Lys Leu Val Ile Glu Leu Ala Leu Glu Ala Val Lys
        195                 200                 205

Glu Asp Pro Ser Thr Asp Ala Leu Arg Ala Val Leu Glu Ala Val Arg
    210                 215                 220

Leu Ala Ser Glu Val Ala Lys Arg Val Thr Asp Pro Asp Lys Ala Leu
225                 230                 235                 240

```
Lys Ile Ala Lys Leu Val Leu Glu Leu Ala Ala Glu Ala Val Lys Glu
                245                 250                 255

Asp Pro Ser Thr Asp Ala Leu Arg Ala Ala Lys Glu Ala Glu Arg Leu
            260                 265                 270

Ala Thr Glu Val Ala Lys Arg Val Thr Asp Pro Lys Lys Ala Arg Glu
        275                 280                 285

Ile Glu Met Leu Val Leu Lys Leu Gln Met Glu Ala Ile Leu Ala Glu
    290                 295                 300

Thr Glu Glu Val Lys Lys Glu Ile Glu Glu Ser Lys Lys Arg Pro Gln
305                 310                 315                 320

Ser Glu Ser Ala Lys Asn Leu Ile Leu Ile Met Gln Leu Leu Ile Asn
                325                 330                 335

Gln Ile Arg Leu Leu Ala Leu Gln Ile Arg Met Leu Ala Leu Gln Leu
            340                 345                 350

Gln Glu Gly Ser Leu Glu His His His His His His
        355                 360


<210> SEQ ID NO 10
<211> LENGTH: 225
<212> TYPE: PRT
<213> ORGANISM: Artificial Sequence
<220> FEATURE:
<223> OTHER INFORMATION: Synthetic

<400> SEQUENCE: 10

Lys Ala Glu Leu Ala Ser Glu Lys Pro Phe Arg Asp Cys Ala Asp Val
1               5                   10                  15

Tyr Gln Ala Gly Phe Asn Lys Ser Gly Ile Tyr Thr Ile Tyr Ile Asn
            20                  25                  30

Asn Met Pro Glu Pro Lys Lys Val Phe Cys Asn Met Asp Val Asn Gly
        35                  40                  45

Gly Gly Trp Thr Val Ile Gln His Arg Glu Asp Gly Ser Leu Asp Phe
    50                  55                  60

Gln Arg Gly Trp Lys Glu Tyr Lys Met Gly Phe Gly Asn Pro Ser Gly
65                  70                  75                  80

Glu Tyr Trp Leu Gly Asn Glu Phe Ile Phe Ala Ile Thr Ser Gln Arg
                85                  90                  95

Gln Tyr Met Leu Arg Ile Glu Leu Met Asp Trp Glu Gly Asn Arg Ala
            100                 105                 110

Tyr Ser Gln Tyr Asp Arg Phe His Ile Gly Asn Glu Lys Gln Asn Tyr
        115                 120                 125

Arg Leu Tyr Leu Lys Gly His Thr Gly Thr Ala Gly Lys Gln Ser Ser
    130                 135                 140

Leu Ile Leu His Gly Ala Asp Phe Ser Thr Lys Asp Ala Asp Asn Asp
145                 150                 155                 160

Asn Cys Met Cys Lys Cys Ala Leu Met Leu Thr Gly Gly Trp Trp Phe
                165                 170                 175

Asp Ala Cys Gly Pro Ser Asn Leu Asn Gly Met Phe Tyr Thr Ala Gly
            180                 185                 190

Gln Asn His Gly Lys Leu Asn Gly Ile Lys Trp His Tyr Phe Lys Gly
        195                 200                 205

Pro Ser Tyr Ser Leu Arg Ser Thr Thr Met Met Ile Arg Pro Leu Asp
    210                 215                 220

Phe
225
```

<210> SEQ ID NO 11
<211> LENGTH: 449
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Asn Ser Gly Ser Ser Thr Ile Thr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Gly Tyr Tyr Gly Pro Tyr Tyr Phe Asp Tyr Trp Gly Gln Gly
            100                 105                 110

Thr Ala Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 12
<211> LENGTH: 214
<212> TYPE: PRT
<213> ORGANISM: Artificial Sequence
<220> FEATURE:
<223> OTHER INFORMATION: Synthetic

<400> SEQUENCE: 12

Asp Ile Val Met Thr Gln Ser His Lys Phe Met Ser Thr Ser Val Gly
1               5                   10                  15

Asp Arg Val Ser Phe Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Glu Tyr Ser Ser Tyr Pro Leu
                85                  90                  95

Thr Phe Gly Val Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 448
<212> TYPE: PRT
<213> ORGANISM: Artificial Sequence
<220> FEATURE:
<223> OTHER INFORMATION: Synthetic

<400> SEQUENCE: 13

-continued

```
Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Phe
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Thr Thr Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Arg Arg Tyr Asp Tyr Asp Thr Trp Phe Ala Tyr Trp Gly Gln Gly
            100                 105                 110

Thr Leu Val Thr Val Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Ser Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

420 425 430

Leu His Asn His Tyr Thr Gln Lys Ser Leu Ser Leu Ser Pro Gly Lys
435 440 445

<210> SEQ ID NO 14
<211> LENGTH: 219
<212> TYPE: PRT
<213> ORGANISM: Artificial Sequence
<220> FEATURE:
<223> OTHER INFORMATION: Synthetic

<400> SEQUENCE: 14

Asp Ile Val Met Thr Gln Ala Ala Leu Ser Val Pro Val Thr Pro Gly
1 5 10 15

Glu Ser Val Ser Ile Ser Cys Arg Ser Ser Ser Ser Leu Leu His Arg
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln Arg
85 90 95

Leu Glu Tyr Pro Phe Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 15
<211> LENGTH: 449
<212> TYPE: PRT
<213> ORGANISM: Artificial Sequence
<220> FEATURE:
<223> OTHER INFORMATION: Synthetic

<400> SEQUENCE: 15

Gln Val Gln Leu Gln Gln Pro Gly Val Val Leu Val Met Pro Gly Ala
1 5 10 15

Ser Val Lys Leu Ser Cys Lys Ala Ser Gly Tyr Thr Phe Ala Ser Tyr
20 25 30

Trp Met His Trp Val Lys Gln Arg Pro Gly Gln Gly Leu Glu Trp Ile
35 40 45

Gly Glu Ile Asp Pro Ser Asp Ser Tyr Arg Asn Tyr Asn Gln Lys Phe
50 55 60

```
Lys Gly Lys Ala Thr Leu Thr Val Asp Lys Ser Ser Ser Thr Val Asn
65                  70                  75                  80

Met Gln Leu Ser Ser Leu Thr Ser Glu Asp Ser Ala Val Tyr Tyr Cys
                85                  90                  95

Ala Lys Thr Ser Gly Ile Gly Arg Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 16
<211> LENGTH: 214
<212> TYPE: PRT
<213> ORGANISM: Artificial Sequence
<220> FEATURE:
<223> OTHER INFORMATION: Synthetic

<400> SEQUENCE: 16

Asp Ile Gln Met Ile Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
            20                  25                  30

Val Thr Trp Tyr Gln Gln Lys Gln Gly Lys Ser Pro Gln Leu Leu Val
        35                  40                  45

Phe Asn Ala Lys Asn Leu Val Glu Gly Val Pro Ser Ser Phe Ser Gly
    50                  55                  60

Ser Gly Ser Gly Thr Gln Phe Ser Leu Lys Ile Asp Ser Leu Gln Pro
65                  70                  75                  80

Glu Asp Phe Gly Thr Tyr Tyr Cys Gln His His Tyr Ser Ile Pro Tyr
                85                  90                  95

Thr Phe Gly Gly Gly Thr Lys Leu Glu Met Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 492
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(29)
<223> OTHER INFORMATION: optionally absent
<220> FEATURE:
<221> NAME/KEY: MISC_FEATURE
<222> LOCATION: (255)..(260)
<223> OTHER INFORMATION: optionally absent

<400> SEQUENCE: 17

Met Glu Thr Asp Thr Leu Leu Leu Trp Val Leu Leu Leu Trp Val Pro
1               5                   10                  15

Gly Ser Thr Gly His His His His His His Gly Gly Ser Lys Ala Glu
            20                  25                  30

Leu Ala Ser Glu Lys Pro Phe Arg Asp Cys Ala Asp Val Tyr Gln Ala
        35                  40                  45

Gly Phe Asn Lys Ser Gly Ile Tyr Thr Ile Tyr Ile Asn Asn Met Pro
    50                  55                  60

Glu Pro Lys Lys Val Phe Cys Asn Met Asp Val Asn Gly Gly Gly Trp
65                  70                  75                  80

-continued

```
Thr Val Ile Gln His Arg Glu Asp Gly Ser Leu Asp Phe Gln Arg Gly
                85                  90                  95

Trp Lys Glu Tyr Lys Met Gly Phe Gly Asn Pro Ser Gly Glu Tyr Trp
            100                 105                 110

Leu Gly Asn Glu Phe Ile Phe Ala Ile Thr Ser Gln Arg Gln Tyr Met
        115                 120                 125

Leu Arg Ile Glu Leu Met Asp Trp Glu Gly Asn Arg Ala Tyr Ser Gln
    130                 135                 140

Tyr Asp Arg Phe His Ile Gly Asn Glu Lys Gln Asn Tyr Arg Leu Tyr
145                 150                 155                 160

Leu Lys Gly His Thr Gly Thr Ala Gly Lys Gln Ser Ser Leu Ile Leu
                165                 170                 175

His Gly Ala Asp Phe Ser Thr Lys Asp Ala Asp Asn Asp Asn Cys Met
            180                 185                 190

Cys Lys Cys Ala Leu Met Leu Thr Gly Gly Trp Trp Phe Asp Ala Cys
        195                 200                 205

Gly Pro Ser Asn Leu Asn Gly Met Phe Tyr Thr Ala Gly Gln Asn His
    210                 215                 220

Gly Lys Leu Asn Gly Ile Lys Trp His Tyr Phe Lys Gly Pro Ser Tyr
225                 230                 235                 240

Ser Leu Arg Ser Thr Thr Met Met Ile Arg Pro Leu Asp Phe Gly Gly
                245                 250                 255

Ser Gly Gly Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 18
<211> LENGTH: 492
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(20)
<223> OTHER INFORMATION: optionally absent
<220> FEATURE:
<221> NAME/KEY: MISC_FEATURE
<222> LOCATION: (246)..(251)
<223> OTHER INFORMATION: optionally absent
<220> FEATURE:
<221> NAME/KEY: MISC_FEATURE
<222> LOCATION: (484)..(492)
<223> OTHER INFORMATION: optionally absent

<400> SEQUENCE: 18

```
Met Glu Thr Asp Thr Leu Leu Leu Trp Val Leu Leu Leu Trp Val Pro
1               5                   10                  15

Gly Ser Thr Gly Lys Ala Glu Leu Ala Ser Glu Lys Pro Phe Arg Asp
            20                  25                  30

Cys Ala Asp Val Tyr Gln Ala Gly Phe Asn Lys Ser Gly Ile Tyr Thr
        35                  40                  45

Ile Tyr Ile Asn Asn Met Pro Glu Pro Lys Lys Val Phe Cys Asn Met
    50                  55                  60

Asp Val Asn Gly Gly Gly Trp Thr Val Ile Gln His Arg Glu Asp Gly
65                  70                  75                  80

Ser Leu Asp Phe Gln Arg Gly Trp Lys Glu Tyr Lys Met Gly Phe Gly
                85                  90                  95

Asn Pro Ser Gly Glu Tyr Trp Leu Gly Asn Glu Phe Ile Phe Ala Ile
            100                 105                 110

Thr Ser Gln Arg Gln Tyr Met Leu Arg Ile Glu Leu Met Asp Trp Glu
        115                 120                 125

Gly Asn Arg Ala Tyr Ser Gln Tyr Asp Arg Phe His Ile Gly Asn Glu
    130                 135                 140

Lys Gln Asn Tyr Arg Leu Tyr Leu Lys Gly His Thr Gly Thr Ala Gly
145                 150                 155                 160

Lys Gln Ser Ser Leu Ile Leu His Gly Ala Asp Phe Ser Thr Lys Asp
                165                 170                 175

Ala Asp Asn Asp Asn Cys Met Cys Lys Cys Ala Leu Met Leu Thr Gly
            180                 185                 190

Gly Trp Trp Phe Asp Ala Cys Gly Pro Ser Asn Leu Asn Gly Met Phe
        195                 200                 205

Tyr Thr Ala Gly Gln Asn His Gly Lys Leu Asn Gly Ile Lys Trp His
    210                 215                 220

Tyr Phe Lys Gly Pro Ser Tyr Ser Leu Arg Ser Thr Thr Met Met Ile
225                 230                 235                 240

Arg Pro Leu Asp Phe Gly Gly Ser Gly Gly Ser Glu Pro Lys Ser Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300
```

Glu Asp Pro Glu Val Lys Phe Asn Trp Tyr Val Asp Gly Val Glu Val
305 310 315 320

His Asn Ala Lys Thr Lys Pro Arg Glu Glu Gln Tyr Asn Ser Thr Tyr
325 330 335

Arg Val Val Ser Val Leu Thr Val Leu His Gln Asp Trp Leu Asn Gly
340 345 350

Lys Glu Tyr Lys Cys Lys Val Ser Asn Lys Ala Leu Pro Ala Pro Ile
355 360 365

Glu Lys Thr Ile Ser Lys Ala Lys Gly Gln Pro Arg Glu Pro Gln Val
370 375 380

Tyr Thr Leu Pro Pro Ser Arg Asp Glu Leu Thr Lys Asn Gln Val Ser
385 390 395 400

Leu Thr Cys Leu Val Lys Gly Phe Tyr Pro Ser Asp Ile Ala Val Glu
405 410 415

Trp Glu Ser Asn Gly Gln Pro Glu Asn Asn Tyr Lys Thr Thr Pro Pro
420 425 430

Val Leu Asp Ser Asp Gly Ser Phe Phe Leu Tyr Ser Lys Leu Thr Val
435 440 445

Asp Lys Ser Arg Trp Gln Gln Gly Asn Val Phe Ser Cys Ser Val Met
450 455 460

His Glu Ala Leu His Asn His Tyr Thr Gln Lys Ser Leu Ser Leu Ser
465 470 475 480

Pro Gly Lys Gly Gly Ser His His His His His His
485 490

<210> SEQ ID NO 19
<211> LENGTH: 452
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asp Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Asn Arg Leu Arg Ser Asp Asp Thr Ala Val Tyr Tyr Cys
85 90 95

Ala Arg Asp Gln Pro Leu Gly Tyr Cys Thr Asn Gly Val Cys Ser Tyr
100 105 110

Phe Asp Tyr Trp Gly Gln Gly Thr Leu Val Thr Val Ser Ser Ala Ser
115 120 125

Thr Lys Gly Pro Ser Val Phe Pro Leu Ala Pro Cys Ser Arg Ser Thr
130 135 140

Ser Glu Ser Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Asn Phe Gly Thr Gln Thr Tyr Thr
195 200 205

Cys Asn Val Asp His Lys Pro Ser Asn Thr Lys Val Asp Lys Thr Val
210 215 220

Glu Arg Lys Cys Cys Val Glu Cys Pro Pro Cys Pro Ala Pro Pro Val
225 230 235 240

Ala Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Gln Phe Asn Trp Tyr Val Asp Gly Val Glu
275 280 285

Val His Asn Ala Lys Thr Lys Pro Arg Glu Glu Gln Phe Asn Ser Thr
290 295 300

Arg Phe Val Val Ser Val Leu Thr Val Val His Gln Asp Trp Leu Asn
305 310 315 320

Gly Lys Glu Tyr Lys Cys Lys Val Ser Asn Lys Gly Leu Pro Ala Pro
325 330 335

Ile Glu Lys Thr Ile Ser Lys Thr Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Met Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Tyr Ser Trp
20 25 30

Leu Ala Trp Tyr Gln Gln Lys Pro Gly Lys Ala Pro Asn Leu Leu Ile
35 40 45

Tyr Thr Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 21
<211> LENGTH: 448
<212> TYPE: PRT
<213> ORGANISM: Artificial Sequence
<220> FEATURE:
<223> OTHER INFORMATION: Synthetic

<400> SEQUENCE: 21

Gln Leu Gln Leu Gln Glu Ser Gly Pro Gly Leu Leu Lys Pro Ser Glu
1               5                   10                  15

Thr Leu Ser Leu Thr Cys Thr Val Ser Gly Gly Ser Ile Ser Ser Pro
            20                  25                  30

Gly Tyr Tyr Gly Gly Trp Ile Arg Gln Pro Pro Gly Lys Gly Leu Glu
        35                  40                  45

Trp Ile Gly Ser Ile Tyr Lys Ser Gly Ser Thr Tyr His Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Pro Val Val Arg Tyr Phe Gly Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220
```

Pro Pro Cys Pro Pro Cys Pro Ala Pro Glu Phe Glu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

Lys Thr Lys Pro Arg Glu Glu Gln Phe Asn Ser Thr Tyr Arg Val Val
290 295 300

Ser Val Leu Thr Val Leu His Gln Asp Gln Leu Asn Gly Lys Glu Tyr
305 310 315 320

Lys Cys Lys Val Ser Asn Lys Gly Leu Pro Ser Ser Ile Glu Lys Thr
325 330 335

Ile Ser Lys Ala Lys Gly Gln Pro Arg Glu Pro Gln Val Tyr Thr Leu
340 345 350

Pro Pro Ser Gln Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Arg Leu Thr Val Asp Lys Ser
405 410 415

Arg Trp Gln Glu Gly Asn Val Phe Ser Cys Ser Val Met His Glu Ala
420 425 430

Leu His Asn His Tyr Thr Gln Lys Ser Leu Ser Leu Ser Leu Gly Lys
435 440 445

<210> SEQ ID NO 22
<211> LENGTH: 213
<212> TYPE: PRT
<213> ORGANISM: Artificial Sequence
<220> FEATURE:
<223> OTHER INFORMATION: Synthetic

<400> SEQUENCE: 22

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Asn Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Thr
85 90 95

Phe Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 23
<211> LENGTH: 448
<212> TYPE: PRT
<213> ORGANISM: Artificial Sequence
<220> FEATURE:
<223> OTHER INFORMATION: Synthetic

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285
```

```
Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 24
<211> LENGTH: 216
<212> TYPE: PRT
<213> ORGANISM: Artificial Sequence
<220> FEATURE:
<223> OTHER INFORMATION: Synthetic

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205
```

Lys Ser Phe Asn Arg Gly Glu Cys
    210                 215

<210> SEQ ID NO 25
<211> LENGTH: 442
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
355 360 365

Pro Ser Asp Ile Ala Val Glu Trp Glu Ser Asn Gly Gln Pro Glu Asn
370 375 380

Asn Tyr Lys Thr Thr Pro Pro Met Leu Asp Ser Asp Gly Ser Phe Phe
385 390 395 400

Leu Tyr Ser Lys Leu Thr Val Asp Lys Ser Arg Trp Gln Gln Gly Asn
405 410 415

Val Phe Ser Cys Ser Val Met His Glu Ala Leu His Asn His Tyr Thr
420 425 430

Gln Lys Ser Leu Ser Leu Ser Pro Gly Lys
435 440

<210> SEQ ID NO 26
<211> LENGTH: 214
<212> TYPE: PRT
<213> ORGANISM: Artificial Sequence
<220> FEATURE:
<223> OTHER INFORMATION: Synthetic

<400> SEQUENCE: 26

Ser Tyr Glu Leu Thr Gln Pro Pro Ser Val Ser Val Ser Pro Gly Gln
1 5 10 15

Thr Ala Ser Ile Thr Cys Ser Gly Asp Asn Ile Gly Asp Gln Tyr Ala
20 25 30

His Trp Tyr Gln Gln Lys Pro Gly Gln Ser Pro Val Leu Val Ile Tyr
35 40 45

Gln Asp Lys Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Ala Thr Tyr Thr Gly Phe Gly Ser Leu
85 90 95

Ala Val Phe Gly Gly Gly Thr Lys Leu Thr Val Leu Gly Gln Pro Lys
100 105 110

Ala Ala Pro Ser Val Thr Leu Phe Pro Pro Ser Ser Glu Glu Leu Gln
115 120 125

Ala Asn Lys Ala Thr Leu Val Cys Leu Ile Ser Asp Phe Tyr Pro Gly
130 135 140

Ala Val Thr Val Ala Trp Lys Ala Asp Ser Ser Pro Val Lys Ala Gly
145 150 155 160

Val Glu Thr Thr Thr Pro Ser Lys Gln Ser Asn Asn Lys Tyr Ala Ala
165 170 175

Ser Ser Tyr Leu Ser Leu Thr Pro Glu Gln Trp Lys Ser His Arg Ser
180 185 190

Tyr Ser Cys Gln Val Thr His Glu Gly Ser Thr Val Glu Lys Thr Val
195 200 205

Ala Pro Thr Glu Cys Ser
210

<210> SEQ ID NO 27
<211> LENGTH: 451
<212> TYPE: PRT
<213> ORGANISM: Artificial Sequence
<220> FEATURE:
<223> OTHER INFORMATION: Synthetic

<400> SEQUENCE: 27

```
Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 28
<211> LENGTH: 213
<212> TYPE: PRT
<213> ORGANISM: Artificial Sequence
<220> FEATURE:
<223> OTHER INFORMATION: Synthetic

<400> SEQUENCE: 28

Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 29
<211> LENGTH: 740
<212> TYPE: PRT
<213> ORGANISM: Artificial Sequence
<220> FEATURE:
<223> OTHER INFORMATION: Synthetic

<400> SEQUENCE: 29

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45
```

```
His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val Gly Gly Ser Gly Ser Gly Asn Gly Ser Arg Val Ala Ala His Ile
                165                 170                 175

Thr Gly Thr Arg Gly Arg Ser Asn Thr Leu Ser Ser Pro Asn Ser Lys
            180                 185                 190

Asn Glu Lys Ala Leu Gly Arg Lys Ile Asn Ser Trp Glu Ser Ser Arg
        195                 200                 205

Ser Gly His Ser Phe Leu Ser Asn Leu His Leu Arg Asn Gly Glu Leu
    210                 215                 220

Val Ile His Glu Lys Gly Phe Tyr Tyr Ile Tyr Ser Gln Thr Tyr Phe
225                 230                 235                 240

Arg Phe Gln Glu Glu Ile Lys Glu Asn Thr Lys Asn Asp Lys Gln Met
                245                 250                 255

Val Gln Tyr Ile Tyr Lys Tyr Thr Ser Tyr Pro Asp Pro Ile Leu Leu
            260                 265                 270

Met Lys Ser Ala Arg Asn Ser Cys Trp Ser Lys Asp Ala Glu Tyr Gly
        275                 280                 285

Leu Tyr Ser Ile Tyr Gln Gly Gly Ile Phe Glu Leu Lys Glu Asn Asp
    290                 295                 300

Arg Ile Phe Val Ser Val Thr Asn Glu His Leu Ile Asp Met Asp His
305                 310                 315                 320

Glu Ala Ser Phe Phe Gly Ala Phe Leu Val Gly Gly Ser Gly Ser Gly
                325                 330                 335

Asn Gly Ser Arg Val Ala Ala His Ile Thr Gly Thr Arg Gly Arg Ser
            340                 345                 350

Asn Thr Leu Ser Ser Pro Asn Ser Lys Asn Glu Lys Ala Leu Gly Arg
        355                 360                 365

Lys Ile Asn Ser Trp Glu Ser Ser Arg Ser Gly His Ser Phe Leu Ser
    370                 375                 380

Asn Leu His Leu Arg Asn Gly Glu Leu Val Ile His Glu Lys Gly Phe
385                 390                 395                 400

Tyr Tyr Ile Tyr Ser Gln Thr Tyr Phe Arg Phe Gln Glu Glu Ile Lys
                405                 410                 415

Glu Asn Thr Lys Asn Asp Lys Gln Met Val Gln Tyr Ile Tyr Lys Tyr
            420                 425                 430

Thr Ser Tyr Pro Asp Pro Ile Leu Leu Met Lys Ser Ala Arg Asn Ser
        435                 440                 445

Cys Trp Ser Lys Asp Ala Glu Tyr Gly Leu Tyr Ser Ile Tyr Gln Gly
    450                 455                 460
```

```
Gly Ile Phe Glu Leu Lys Glu Asn Asp Arg Ile Phe Val Ser Val Thr
465                 470                 475                 480

Asn Glu His Leu Ile Asp Met Asp His Glu Ala Ser Phe Phe Gly Ala
                485                 490                 495

Phe Leu Val Gly Gly Pro Gly Ser Ser Ser Ser Ser Ser Ser Gly Ser
            500                 505                 510

Cys Asp Lys Thr His Thr Cys Pro Pro Cys Pro Ala Pro Glu Leu Leu
        515                 520                 525

Gly Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Ser Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
    610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740
```

<210> SEQ ID NO 30
<211> LENGTH: 486
<212> TYPE: PRT
<213> ORGANISM: Artificial Sequence
<220> FEATURE:
<223> OTHER INFORMATION: Synthetic

<400> SEQUENCE: 30

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Thr Val Ala Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Lys Ser Arg Ile Thr Ile Asn Val Asp Thr Ser Lys Asn
65                  70                  75                  80
```

```
Gln Ile Ser Leu Gln Leu Asn Ser Val Thr Pro Glu Asp Thr Ala Val
                85                  90                  95

Tyr Tyr Cys Ala Arg Glu Pro Asp Ala Gly Arg Gly Ala Phe Asp Ile
            100                 105                 110

Trp Gly Gln Gly Thr Thr Val Thr Ser Pro Leu Arg Trp Gly Arg Phe
        115                 120                 125

Gly Trp Arg Gly Leu Gly Arg Gly Trp Leu Arg Ser Pro Val Thr Gln
    130                 135                 140

Ser Pro Gly Thr Leu Ser Leu Ser Pro Gly Glu Arg Ala Thr Leu Ser
145                 150                 155                 160

Cys Arg Ala Ser Gln Ser Val Ser Ser Ser His Leu Ala Trp Tyr Gln
                165                 170                 175

Gln Lys Pro Gly Gln Ala Pro Arg Leu Leu Ile Tyr Gly Ala Ser Ser
            180                 185                 190

Arg Ala Thr Gly Ile Pro Asp Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Ser Asn Trp Pro Pro Arg Ala Val Phe Gly
225                 230                 235                 240

Gln Gly Thr Arg Leu Glu Ile Lys Gly Gly Ser Gly Gly Ser Glu Pro
                245                 250                 255

Lys Ser Ser Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485
```

<210> SEQ ID NO 31
<211> LENGTH: 452
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Thr Val Ala Trp Asp Trp Ile Arg Gln Ser Pro Ser Arg Gly Leu Glu
        35                  40                  45

Trp Leu Gly Arg Thr Tyr Tyr Arg Ser Lys Trp Tyr Asn Glu Tyr Ala
    50                  55                  60

Val Ser Val Lys Ser Arg Ile Thr Ile Asn Val Asp Thr Ser Lys Asn
65                  70                  75                  80

Gln Ile Ser Leu Gln Leu Asn Ser Val Thr Pro Glu Asp Thr Ala Val
                85                  90                  95

Tyr Tyr Cys Ala Arg Glu Pro Asp Ala Gly Arg Gly Ala Phe Asp Ile
            100                 105                 110

Trp Gly Gln Gly Thr Thr Val Thr Ser Pro Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
```

```
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 32
<211> LENGTH: 218
<212> TYPE: PRT
<213> ORGANISM: Artificial Sequence
<220> FEATURE:
<223> OTHER INFORMATION: Synthetic

<400> SEQUENCE: 32

Leu Arg Ser Pro Val Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser His Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Ser Leu
65                  70                  75                  80

Glu Pro Glu Asp Phe Ala Val Tyr Tyr Cys Gln Gln Arg Ser Asn Trp
                85                  90                  95

Pro Pro Arg Ala Val Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 33
<211> LENGTH: 486
<212> TYPE: PRT
<213> ORGANISM: Artificial Sequence
<220> FEATURE:
<223> OTHER INFORMATION: Synthetic

<400> SEQUENCE: 33
```

```
Gln Val Gln Leu Gln Gln Ser Gly Pro Gly Arg Val Gln Pro Ser Gln
1               5                   10                  15

Thr Leu Ser Leu Thr Cys Ala Ile Ser Gly Asp Ser Val Ser Asn Asn
            20                  25                  30

Asn Ala Ala Trp Tyr Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ser Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Gly Asp Gly Asn Ser Tyr Phe Asp Tyr Trp
            100                 105                 110

Gly Gln Gly Thr Leu Val Thr Val Ser Ser Gly Ile Leu Arg Trp Gly
        115                 120                 125

Arg Phe Gly Trp Arg Gly Leu Gly Arg Gly Trp Leu Glu Ile Val Leu
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Gly Tyr Val Ser Trp
                165                 170                 175

Tyr Arg Gln Lys Pro Gly Gln Ala Pro Arg Leu Leu Ile Tyr Gly Ala
            180                 185                 190

Ser Thr Arg Ala Thr Gly Ile Pro Asp Arg Phe Ser Gly Ser Gly Ser
        195                 200                 205

Gly Thr Asp Phe Thr Leu Thr Ile Ser Arg Leu Glu Pro Glu Asp Phe
    210                 215                 220

Ala Val Tyr Tyr Cys His Gln Tyr Gly Ser Ser Pro Asn Thr Tyr Gly
225                 230                 235                 240

Gln Gly Thr Lys Val Gly Ile Lys Gly Gly Ser Gly Gly Ser Glu Pro
                245                 250                 255

Lys Ser Ser Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
```

```
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485
```

```
<210> SEQ ID NO 34
<211> LENGTH: 452
<212> TYPE: PRT
<213> ORGANISM: Artificial Sequence
<220> FEATURE:
<223> OTHER INFORMATION: Synthetic

<400> SEQUENCE: 34

Gln Val Gln Leu Gln Gln Ser Gly Pro Gly Arg Val Gln Pro Ser Gln
1               5                   10                  15

Thr Leu Ser Leu Thr Cys Ala Ile Ser Gly Asp Ser Val Ser Asn Asn
            20                  25                  30

Asn Ala Ala Trp Tyr Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ser Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Gly Asp Gly Asn Ser Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
```

```
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 35
<211> LENGTH: 216
<212> TYPE: PRT
<213> ORGANISM: Artificial Sequence
<220> FEATURE:
<223> OTHER INFORMATION: Synthetic

<400> SEQUENCE: 35

Leu Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Gly Tyr Val Ser Trp Tyr Arg Gln Lys Pro Gly Gln Ala Pro Arg Leu
        35                  40                  45

Leu Ile Tyr Gly Ala Ser Thr Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys His Gln Tyr Gly Ser Ser
                85                  90                  95

Pro Asn Thr Tyr Gly Gln Gly Thr Lys Val Gly Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
```

```
        195                 200                 205

Lys Ser Phe Asn Arg Gly Glu Cys
    210                 215


<210> SEQ ID NO 36
<211> LENGTH: 451
<212> TYPE: PRT
<213> ORGANISM: Artificial Sequence
<220> FEATURE:
<223> OTHER INFORMATION: Synthetic

<400> SEQUENCE: 36

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 37
<211> LENGTH: 212
<212> TYPE: PRT
<213> ORGANISM: Artificial Sequence
<220> FEATURE:
<223> OTHER INFORMATION: Synthetic

<400> SEQUENCE: 37

Ser Glu Leu Thr Gln Asp Pro Ala Val Ser Val Ala Leu Gly Gln Thr
1 5 10 15

Val Arg Ile Thr Cys Gln Gly Asp Ser Leu Arg Ser Tyr Tyr Ala Ser
20 25 30

Trp Tyr Gln Gln Lys Pro Gly Gln Ala Pro Val Leu Val Ile Tyr Gly
35 40 45

Lys Asn Asn Arg Pro Ser Gly Ile Pro Asp Arg Phe Ser Gly Ser Ser
50 55 60

Ser Gly Asn Thr Ala Ser Leu Thr Ile Thr Gly Ala Gln Ala Glu Asp
65 70 75 80

Glu Ala Asp Tyr Tyr Cys Asn Ser Arg Asp Ser Ser Gly Asn His Val
85 90 95

Val Phe Gly Gly Gly Thr Lys Leu Thr Val Leu Gly Gln Pro Lys Ala
100 105 110

Ala Pro Ser Val Thr Leu Phe Pro Pro Ser Ser Glu Glu Leu Gln Ala
115 120 125

Asn Lys Ala Thr Leu Val Cys Leu Ile Ser Asp Phe Tyr Pro Gly Ala
130 135 140

Val Thr Val Ala Trp Lys Ala Asp Ser Ser Pro Val Lys Ala Gly Val
145 150 155 160

Glu Thr Thr Thr Pro Ser Lys Gln Ser Asn Asn Lys Tyr Ala Ala Ser
165 170 175

Ser Tyr Leu Ser Leu Thr Pro Glu Gln Trp Lys Ser His Lys Ser Tyr
180 185 190

Ser Cys Gln Val Thr His Glu Gly Ser Thr Val Glu Lys Thr Val Ala
195 200 205

Pro Thr Glu Cys
210

<210> SEQ ID NO 38
<211> LENGTH: 452
<212> TYPE: PRT

<213> ORGANISM: Artificial Sequence
<220> FEATURE:
<223> OTHER INFORMATION: Synthetic

<400> SEQUENCE: 38

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Asp Lys Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
385                 390                 395                 400

Pro Val Leu Asp Ser Asp Gly Ser Phe Phe Leu Tyr Ser Lys Leu Thr
                405                 410                 415

Val Asp Leu Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 39
<211> LENGTH: 214
<212> TYPE: PRT
<213> ORGANISM: Artificial Sequence
<220> FEATURE:
<223> OTHER INFORMATION: Synthetic

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 40
<211> LENGTH: 449
<212> TYPE: PRT
<213> ORGANISM: Artificial Sequence
<220> FEATURE:
<223> OTHER INFORMATION: Synthetic

<400> SEQUENCE: 40

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Gly Tyr Tyr Ala Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

435 440 445

Lys

<210> SEQ ID NO 41
<211> LENGTH: 218
<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Thr Ser
20 25 30

Ser Tyr Ser Tyr Met His Trp Tyr Gln Gln Lys Pro Gly Lys Ala Pro
35 40 45

Lys Leu Leu Ile Lys Tyr Ala Ser Asn Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Ser Trp
85 90 95

Glu Ile Pro Tyr Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 42
<211> LENGTH: 444
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Phe Thr Gly Tyr
20 25 30

Tyr Ile His Trp Val Arg Gln Ala Pro Gly Lys Gly Leu Glu Trp Val
35 40 45

Ala Arg Val Ile Pro Asn Ala Gly Gly Thr Ser Tyr Asn Gln Lys Phe
50 55 60

Lys Gly Arg Phe Thr Leu Ser Val Asp Asn Ser Lys Asn Thr Ala Tyr

```
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 43
<211> LENGTH: 219
<212> TYPE: PRT
<213> ORGANISM: Artificial Sequence
<220> FEATURE:
<223> OTHER INFORMATION: Synthetic

<400> SEQUENCE: 43

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Leu Val His Ser
20 25 30

Asn Gly Asn Thr Phe Leu His Trp Tyr Gln Gln Lys Pro Gly Lys Ala
35 40 45

Pro Lys Leu Leu Ile Tyr Thr Val Ser Asn Arg Phe Ser Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Phe Cys Ser Gln Thr
85 90 95

Thr His Val Pro Trp Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 44
<211> LENGTH: 239
<212> TYPE: PRT
<213> ORGANISM: Artificial Sequence
<220> FEATURE:
<223> OTHER INFORMATION: Synthetic

<400> SEQUENCE: 44

Met Ala Leu Pro Ala Gln Leu Leu Gly Leu Leu Met Leu Trp Val Ser
1 5 10 15

Gly Ser Ser Gly Asp Ile Val Met Thr Gln Ser Pro Leu Ser Leu Thr
20 25 30

Val Thr Pro Gly Glu Pro Ala Ser Ile Ser Cys Arg Ser Ser Gln Ser
35 40 45

Leu Leu Tyr Ser Asn Gly Tyr Asn Tyr Leu Asp Trp Tyr Leu Gln Lys
50 55 60

Pro Gly Gln Ser Pro Gln Val Leu Ile Ser Leu Gly Ser Asn Arg Ala
65 70 75 80

Ser Gly Val Pro Asp Arg Phe Ser Gly Ser Gly Ser Gly Thr Asp Phe
85 90 95

Thr Leu Lys Ile Ser Arg Val Glu Ala Glu Asp Val Gly Val Tyr Tyr
100 105 110

Cys Met Gln Ala Arg Gln Thr Pro Phe Thr Phe Gly Pro Gly Thr Lys
115 120 125

Val Asp Ile Arg Arg Thr Val Ala Ala Pro Ser Val Phe Ile Phe Pro

```
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 45
<211> LENGTH: 469
<212> TYPE: PRT
<213> ORGANISM: Artificial Sequence
<220> FEATURE:
<223> OTHER INFORMATION: Synthetic

<400> SEQUENCE: 45

Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ala Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
```

260 265 270

Leu Met Ile Ser Arg Thr Pro Glu Val Thr Cys Val Val Val Asp Val
275 280 285

Ser His Glu Asp Pro Glu Val Lys Phe Asn Trp Tyr Val Asp Gly Val
290 295 300

Glu Val His Asn Ala Lys Thr Lys Pro Arg Glu Glu Gln Tyr Asn Ser
305 310 315 320

Thr Tyr Arg Val Val Ser Val Leu Thr Val Leu His Gln Asp Trp Leu
325 330 335

Asn Gly Lys Glu Tyr Lys Cys Lys Val Ser Asn Lys Ala Leu Pro Ala
340 345 350

Pro Ile Glu Lys Thr Ile Ser Lys Ala Lys Gly Gln Pro Arg Glu Pro
355 360 365

Gln Val Tyr Thr Leu Pro Pro Ser Arg Glu Glu Met Thr Lys Asn Gln
370 375 380

Val Ser Leu Thr Cys Leu Val Lys Gly Phe Tyr Pro Ser Asp Ile Ala
385 390 395 400

Val Glu Trp Glu Ser Asn Gly Gln Pro Glu Asn Asn Tyr Lys Thr Thr
405 410 415

Pro Pro Val Leu Asp Ser Asp Gly Ser Phe Phe Leu Tyr Ser Lys Leu
420 425 430

Thr Val Asp Lys Ser Arg Trp Gln Gln Gly Asn Val Phe Ser Cys Ser
435 440 445

Val Met His Glu Ala Leu His Asn His Tyr Thr Gln Lys Ser Leu Ser
450 455 460

Leu Ser Pro Gly Lys
465

<210> SEQ ID NO 46
<211> LENGTH: 469
<212> TYPE: PRT
<213> ORGANISM: Artificial Sequence
<220> FEATURE:
<223> OTHER INFORMATION: Synthetic

<400> SEQUENCE: 46

Met Glu Phe Gly Leu Ser Trp Val Phe Leu Val Ala Ile Leu Arg Gly
1 5 10 15

Val Gln Cys Gln Val Gln Leu Val Glu Ser Gly Gly Gly Val Val Gln
20 25 30

Pro Gly Arg Ser Leu Arg Leu Ser Cys Ala Ala Ser Gly Phe Thr Phe
35 40 45

Ser Ser Tyr Gly Met His Trp Val Arg Gln Ala Pro Gly Lys Gly Leu
50 55 60

Glu Trp Val Ala Val Ile Ser Tyr Glu Glu Ser Asn Arg Tyr His Ala
65 70 75 80

Asp Ser Val Lys Gly Arg Phe Thr Ile Ser Arg Asp Asn Ser Lys Ile
85 90 95

Thr Leu Tyr Leu Gln Met Asn Ser Leu Arg Thr Glu Asp Thr Ala Val
100 105 110

Tyr Tyr Cys Ala Arg Asp Gly Gly Ile Ala Ala Pro Gly Pro Asp Tyr
115 120 125

Trp Gly Gln Gly Thr Leu Val Thr Val Ser Ser Ala Ser Thr Lys Gly
130 135 140

Pro Ser Val Phe Pro Leu Ala Pro Ser Ser Lys Ser Thr Ser Gly Gly

```
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 47
<211> LENGTH: 457
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (226)..(227)
<223> OTHER INFORMATION: optional amino acid linker of any suitable length and content

<400> SEQUENCE: 47

```
Lys Ala Glu Leu Ala Ser Glu Lys Pro Phe Arg Asp Cys Ala Asp Val
1               5                   10                  15
```

```
Tyr Gln Ala Gly Phe Asn Lys Ser Gly Ile Tyr Thr Ile Tyr Ile Asn
            20                  25                  30

Asn Met Pro Glu Pro Lys Lys Val Phe Cys Asn Met Asp Val Asn Gly
        35                  40                  45

Gly Gly Trp Thr Val Ile Gln His Arg Glu Asp Gly Ser Leu Asp Phe
    50                  55                  60

Gln Arg Gly Trp Lys Glu Tyr Lys Met Gly Phe Gly Asn Pro Ser Gly
65                  70                  75                  80

Glu Tyr Trp Leu Gly Asn Glu Phe Ile Phe Ala Ile Thr Ser Gln Arg
                85                  90                  95

Gln Tyr Met Leu Arg Ile Glu Leu Met Asp Trp Glu Gly Asn Arg Ala
            100                 105                 110

Tyr Ser Gln Tyr Asp Arg Phe His Ile Gly Asn Glu Lys Gln Asn Tyr
        115                 120                 125

Arg Leu Tyr Leu Lys Gly His Thr Gly Thr Ala Gly Lys Gln Ser Ser
    130                 135                 140

Leu Ile Leu His Gly Ala Asp Phe Ser Thr Lys Asp Ala Asp Asn Asp
145                 150                 155                 160

Asn Cys Met Cys Lys Cys Ala Leu Met Leu Thr Gly Gly Trp Trp Phe
                165                 170                 175

Asp Ala Cys Gly Pro Ser Asn Leu Asn Gly Met Phe Tyr Thr Ala Gly
            180                 185                 190

Gln Asn His Gly Lys Leu Asn Gly Ile Lys Trp His Tyr Phe Lys Gly
        195                 200                 205

Pro Ser Tyr Ser Leu Arg Ser Thr Thr Met Met Ile Arg Pro Leu Asp
    210                 215                 220

Phe Glu Pro Lys Ser Ser Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430
```

```
Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 48
<211> LENGTH: 453
<212> TYPE: PRT
<213> ORGANISM: Artificial Sequence
<220> FEATURE:
<223> OTHER INFORMATION: Synthetic

<400> SEQUENCE: 48

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Ile Arg Gln Ala Pro Gly Lys Gly Leu Glu Trp Val
        35                  40                  45

Ala Val Ile Trp Tyr Glu Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Gly Leu Asp Tyr Tyr Ser Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 49
<211> LENGTH: 214
<212> TYPE: PRT
<213> ORGANISM: Artificial Sequence
<220> FEATURE:
<223> OTHER INFORMATION: Synthetic

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 50
<211> LENGTH: 449
```

<212> TYPE: PRT
<213> ORGANISM: Artificial Sequence
<220> FEATURE:
<223> OTHER INFORMATION: Synthetic

<400> SEQUENCE: 50

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 51
<211> LENGTH: 214
<212> TYPE: PRT
<213> ORGANISM: Artificial Sequence
<220> FEATURE:
<223> OTHER INFORMATION: Synthetic

<400> SEQUENCE: 51

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Asn Asn Val His Ser
65 70 75 80

Glu Asp Leu Ala Glu Tyr Phe Cys Gln Gln Tyr Asn Thr Asp Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 52
<211> LENGTH: 448
<212> TYPE: PRT
<213> ORGANISM: Artificial Sequence
<220> FEATURE:
<223> OTHER INFORMATION: Synthetic

<400> SEQUENCE: 52

Gln Val Gln Leu Val Glu Ser Gly Gly Gly Val Val Gln Pro Gly Arg
1 5 10 15

-continued

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gly Gly Tyr Tyr Asp Ser Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Ser Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
```

435 440 445

<210> SEQ ID NO 53
<211> LENGTH: 218
<212> TYPE: PRT
<213> ORGANISM: Artificial Sequence
<220> FEATURE:
<223> OTHER INFORMATION: Synthetic

<400> SEQUENCE: 53

Glu Ile Val Leu Thr Gln Ser Pro Gly Thr Leu Ser Leu Ser Pro Gly
1 5 10 15

Glu Arg Ala Thr Leu Ser Cys Arg Ala Ser Glu Ser Val Asp Asn Tyr
20 25 30

Gly Val Ser Phe Met Asn Trp Tyr Gln Gln Lys Pro Gly Gln Ala Pro
35 40 45

Arg Leu Leu Ile Tyr Ala Ala Ser Asn Gln Gly Ser Gly Ile Pro Asp
50 55 60

Arg Phe Ser Gly Ser Gly Ser Gly Thr Asp Phe Thr Leu Thr Ile Ser
65 70 75 80

Arg Leu Glu Pro Glu Asp Phe Ala Val Tyr Tyr Cys Gln Gln Thr Lys
85 90 95

Glu Val Thr Trp Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 54
<211> LENGTH: 449
<212> TYPE: PRT
<213> ORGANISM: Artificial Sequence
<220> FEATURE:
<223> OTHER INFORMATION: Synthetic

<400> SEQUENCE: 54

Gln Val Thr Leu Lys Glu Ser Gly Pro Gly Ile Leu Lys Pro Ser Gln
1 5 10 15

Thr Leu Ser Leu Thr Cys Ser Phe Ser Gly Phe Ser Leu Ser Thr Ser
20 25 30

Gly Met Gly Val Gly Trp Ile Arg Gln Pro Ser Gly Lys Gly Leu Glu
35 40 45

Trp Leu Ala His Ile Trp Trp Asp Asp Asp Lys Tyr Tyr Asn Pro Ser
50 55 60

Leu Lys Ser Gln Leu Thr Ile Ser Lys Asp Thr Ser Arg Asn Gln Val
65 70 75 80

```
Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 55
<211> LENGTH: 214
<212> TYPE: PRT
<213> ORGANISM: Artificial Sequence
<220> FEATURE:
<223> OTHER INFORMATION: Synthetic

<400> SEQUENCE: 55

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val His Ser
65                  70                  75                  80

Glu Asp Leu Ala Glu Tyr Phe Cys Gln Gln Tyr Asn Thr Asp Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 633
<212> TYPE: PRT
<213> ORGANISM: Artificial Sequence
<220> FEATURE:
<223> OTHER INFORMATION: Synthetic

<400> SEQUENCE: 56

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys

```
130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240

Val Leu Lys Asn Asn Thr Tyr Trp Gly Ile Ile Leu Leu Ala Asn Pro
                245                 250                 255

Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365

Phe Asn Ser Glu His Gln Val Leu Lys Asn Asn Thr Tyr Trp Gly Ile
    370                 375                 380

Ile Leu Leu Ala Asn Pro Gln Phe Ile Ser Gly Ser Ser Ser Ser Ser
385                 390                 395                 400

Ser Ser Ser Gly Ser Cys Asp Lys Thr His Thr Cys Pro Pro Cys Pro
                405                 410                 415

Ala Pro Glu Leu Leu Gly Gly Pro Ser Val Phe Leu Phe Pro Pro Lys
            420                 425                 430

Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
    450                 455                 460

Val Asp Gly Val Glu Val His Asn Ala Lys Thr Lys Pro Arg Glu Glu
465                 470                 475                 480

Gln Tyr Ser Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510

Ala Leu Pro Ala Pro Ile Glu Lys Thr Ile Ser Lys Ala Lys Gly Gln
        515                 520                 525

Pro Arg Glu Pro Gln Val Tyr Thr Leu Pro Pro Ser Arg Glu Glu Met
    530                 535                 540

Thr Lys Asn Gln Val Ser Leu Thr Cys Leu Val Lys Gly Phe Tyr Pro
545                 550                 555                 560
```

-continued

```
Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
    610                 615                 620

Lys Ser Leu Ser Leu Ser Pro Gly Lys
625                 630
```

ANTIBODY-BOUND NANOPARTICLES

CROSS REFERENCE

This application is a U.S. national phase of International Application No. PCT/US2021/036117, filed on Jun. 7, 2021, which claims priority to U.S. Provisional Application Ser. No. 63/088,586, filed Oct. 7, 2020; U.S. Provisional Application Ser. No. 63/088,576, filed Oct. 7, 2020; U.S. Provisional Application Ser. No. 63/085,351, filed Sep. 30, 2020; and U.S. Provisional Application No. 63/036,062, filed Jun. 8, 2020, all of which are incorporated by reference herein in their entirety.

SEQUENCE LISTING STATEMENT

A computer readable form of the Sequence Listing is filed with this application by electronic submission and is incorporated into this application by reference in its entirety. The Sequence Listing is contained in the file created on Jun. 3, 2021 having the file name "20-1330-WO-SeqList_ST25.txt" and is 182,034 bytes in size.

BACKGROUND

Antibodies are very widely used in therapeutics and diagnostics applications. While there have been some efforts to oligomerize antibodies to enhance avidity and receptor clustering, there are no current methods to precisely form ordered and structurally homogeneous antibody-bound nanoparticle structures.

SUMMARY

In a first aspect, the disclosure provides particles, comprising:

(a) a plurality of polypeptide polymers, wherein (i) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:1;

(ii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:2;

(iii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:3;

(iv) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:4;

(v) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5;

(vi) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:6;

(vii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7;

(viii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:8; or (ix) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:9;

wherein residues in parentheses are optional (i.e.: not considered in the percent identity requirement); and (b) a plurality of (i) Tie2 receptor antibodies comprising Fc domains, and/or (ii) dimers of fibrinogen-like domain derived from angiopoietin (F domain)fused to an Fc domain;

wherein (i) each Tie2 antibody or dimer comprises a first Fc domain and a second Fc domain;

(ii) each Tie2 antibody or dimer in the plurality is (A) non-covalently bound via the first Fc domain to one polypeptide monomer chain of a first polymer, and (B) non-covalently bound via the second Fc domain to one polypeptide monomer of a second polymer; and (iii) each polypeptide monomer chain of each polymer is non-covalently bound to one Fc domain;

wherein the particle comprises dihedral, tetrahedral, octahedral, or icosahedral symmetry.

In one embodiment, the Tie2 antibodies or dimers comprise Tie 2 antibodies, wherein the Tie-2 antibodies comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of:

SEQ ID NOS:11-12,

SEQ ID NOS: 13-14, and

SEQ ID NOS:15-16.

In another embodiment, the dimers comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of the amino acid sequence of SEQ ID NO:17 or 18, wherein residues in parentheses are optional.

In another embodiment, the particles or compositions thereof are used for treating comprising treating or limiting development of diseases or syndromes resulting from vascular dysfunction, including but not limited to bacterial or viral infections, sepsis, acute respiratory distress syndrome (ARDS), acute lung injury, acute kidney injury, wet-age related macular degeneration, open angle glaucoma, diabetic retinopathy, and diabetic nephropathy.

In another embodiment, the disclosure comprises polypeptides comprising an amino acid sequence comprising or consisting of the amino acid sequence of any one of SEQ ID NOS: 17-18 and 47, nucleic acids encoding such polypeptides, expression vectors comprising such nucleic acids operatively linked to control sequence, and host cells comprising such polypeptides, nucleic acids, and/or expression vectors.

In other embodiments, the disclosure provides kits comprising (a) a polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in embodiment disclosed herein; and (b) Tie2 antibodies comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of SEQ ID NOS:11-12; SEQ ID NOS:13-14; and SEQ ID NOS:15-16, and/or a fibrinogen-like domain derived from angiopoietin (F domain) fused to an Fc domain optionally comprising the amino acid sequence selected from the group consisting of SEQ ID NOS: 17-18 and 47.

In further embodiments, the disclosure provides kits comprising:

(a) host cells capable of expressing a polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in embodiment disclosed herein; and (b) host cells capable of expressing Tie2 antibodies amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of SEQ ID NOS:11-12; SEQ ID NOS:13-14; and SEQ ID NOS:15-16, and/or a fibrinogen-like domain derived from angiopoietin (F domain) fused to an Fc domain optionally comprising the amino acid sequence selected from the group consisting of SEQ ID NOS: 17-18 and 47.

In another aspect, the disclosure provides particles, comprising:

(a) a plurality of polypeptide polymers, wherein (i) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:1;

(ii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:2;

(iii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:3;

(iv) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:4;

(v) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5;

(vi) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:6;

(vii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7;

(viii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:8; or (ix) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:9; wherein residues in parentheses are optional (i.e.: not considered in the percent identity requirement); and (b) a plurality of α-TNFRSF (tumor necrosis factor receptor superfamily) antibodies comprising Fc domains;

wherein (i) each α-TNFRSF antibody in the plurality of antibodies comprises a first Fc domain and a second Fc domain;

(ii) each α-TNFRSF antibody in the plurality of antibodies is (A) non-covalently bound via the first Fc domain to one polypeptide monomer chain of a first polymer, and (B) non-covalently bound via the second Fc domain to one polypeptide monomer of a second polymer; and (iii) each polypeptide monomer chain of each polymer is non-covalently bound to one Fc domain;

wherein the particle comprises dihedral, tetrahedral, octahedral, or icosahedral symmetry.

In one embodiment, the α-TNFRSF antibody targets one or more of DR5/TRAIL-R2/TNFRSF10B/CD262, CD40, 4-1BB, and TWEAKR (Tumor Necrosis Factor-like Weak Inducer of Apoptosis Receptor)/TNFRSF12A/CD266. In another embodiment, the α-TNFRSF antibodies comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs (when both heavy and light chain are needed) selected from the group consisting of SEQ ID NO: 19 and 20;
SEQ ID NO: 21 and 22;
SEQ ID NO: 23 and 24;
SEQ ID NO: 25 and 26;
SEQ ID NO: 27 and 28;
SEQ ID NO: 29;
SEQ ID NO: 30;
SEQ ID NO: 31 and 32;

SEQ ID NO: 33;
SEQ ID NO: 34 and 35;
SEQ ID NO: 36 and 37;
SEQ ID NO: 38 and 39;
SEQ ID NO: 40 and 41;
SEQ ID NO:42 and 43;
SEQ ID NO: 44 and 45;
SEQ ID NO: 44 and 46;
SEQ ID NO: 48 and 49;
SEQ ID NO: 50 and 51;
SEQ ID NO: 52 and 53
SEQ ID NO: 54 and 55;
SEQ ID NO: 56;
Lob 7/6 heavy and light chains as disclosed in published US patent application US US20090074711; and
Heavy and light chain pairs disclosed in 2018094300.

The disclosure also provides methods for using such particles to treat tumors.

In another embodiment, the disclosure provides kits comprising:

(a) one or more polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in embodiment herein; and (b) α-TNFRSF antibodies comprising an antibody selected from the group consisting of Lob 7/6, Lucatumumab, Dacetuzumab, Selicrelumab, Bleselumab, Urelumab, Utomilumab, Drozitumab, scTRAIL-Fc, KMTR2, 16E2, and Conatumumab (also referred to as AMG 655); optionally as further limited herein.

In another embodiment, the disclosure provides kits comprising:

(a) host cells capable of expressing one or more polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in any embodiment herein; and (b) host cells capable of expressing α-TNFRSF antibodies comprising an antibody selected from the group consisting of Lob 7/6, Lucatumumab, Dacetuzumab, Selicrelumab, Bleselumab, Urelumab, Utomilumab, Drozitumab, scTRAIL-Fc, KMTR2, 16E2, and Conatumumab (also referred to as AMG 655); optionally as further limited herein.

DETAILED DESCRIPTION

Figure 1:
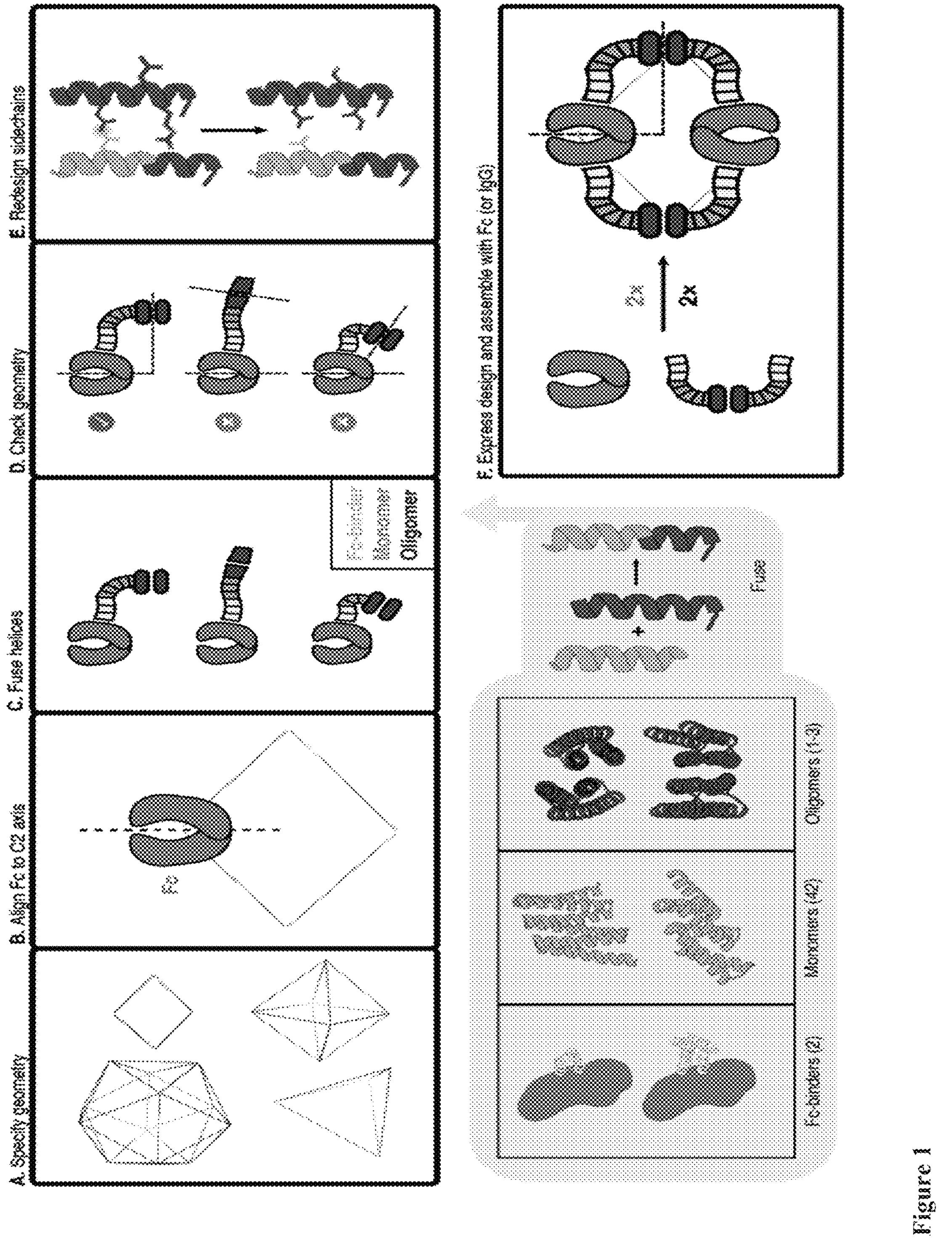
FIG. 1(A-F). Antibody nanocage (AbC) design. A, Polyhedral geometry is specified. B, An antibody Fc model from hIgG1 is aligned to one of the C2 axes (in this case, a D2 dihedron is shown). C, Antibody Fc-binders are fused to helical repeat proteins that are then fused to the monomeric subunit of helical cyclic oligomers. All combinations of building blocks and building block junctions are sampled (below inset). D-E, Tripartite fusions that successfully place the cyclic oligomer axis in the orientation required for the desired polyhedral geometry (D) move forward for side-chain redesign (E). F, Designed AbC-forming oligomers are bacterially expressed, purified, and assembled with antibody Fc or IgG.

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In all embodiments of polypeptides disclosed herein, any N-terminal methionine residues are optional (i.e.: the N-terminal methionine residue may be present or may be absent).

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

In a first aspect, the disclosure provides particles, comprising:

(a) a plurality of polypeptide polymers, wherein
  - (i) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:1;
  - (ii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:2;
  - (iii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:3;
  - (iv) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:4;
  - (v) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5;
  - (vi) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:6;
  - (vii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7;
  - (viii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:8; or
  - (ix) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:9;

wherein residues in parentheses are optional (i.e.: not considered in the percent identity requirement); and (b) a plurality of (i) Tie2 receptor antibodies comprising Fc domains, and/or (ii) dimers of fibrinogen-like domain derived from angiopoietin (F domain) fused to an Fc domain;

wherein
  - (i) each Tie2 antibody or dimer comprises a first Fc domain and a second Fc domain;
  - (ii) each Tie2 antibody or dimer in the plurality is (A) non-covalently bound via the first Fc domain to one polypeptide monomer chain of a first polymer, and (B) non-covalently bound via the second Fc domain to one polypeptide monomer of a second polymer; and (iii) each polypeptide monomer chain of each polymer is non-covalently bound to one Fc domain;

wherein the particle comprises dihedral, tetrahedral, octahedral, or icosahedral symmetry.

As shown in the examples that follow, the particles and compositions of the disclosure Tie2 receptor antibodies comprising Fc domains, and/or dimers of fibrinogen-like domain derived from angiopoietin (F domain) fused to an Fc domain significantly increased AKT and ERK1/2 phosphorylation above baseline and enhanced cell migration and vascular stability, and thus are useful for treating pathological symptoms that arise from bacterial and viral infections. For example, the ability to induce phosphorylation of AKT and ERK, can serve to enhance cell migration and tube formation, improve, wound healing after injury, and thus are useful in treating infections (such as bacterial and viral infections), as well as conditions characterized by diseases or syndromes resulting from vascular dysfunction, including but not limited to sepsis, acute respiratory distress syndrome (ARDS), acute lung injury, acute kidney injury, wet-age related macular degeneration, open angle glaucoma, diabetic retinopathy, and diabetic nephropathy.

The monomers in the plurality of polypeptide polymers comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a polymer, including but not limited to a homo-polymer, and (b) binding to a constant region of an IgG antibody.

TABLE 1

Sequences and original building blocks used for all designs.

| Name | Fc binder (underlined) | Monomer (standard font) | Oligomer (bold font) | Sequence |
|---|---|---|---|---|
| d2.3 SEQ ID NO: 1 | DHR79 | EXT6-DHR62 | bex2c2_G2 | (M)SDEEERNELIKRIREAAQRAREAAERTGDPRVRELARELARIAQIAFYLVLHDPSSSEVNEALKAVVKAIELAVRALEEAEKTGDPEVRELAREVVRLAVEVATATAAGENDTLRKVAERALRLAKEAAKRGDAKAAKQAAKIAKLAAANAGDEDVLKKVELVRLA**IELVEIVVENAKRKGDDDKEAAEAALAAFRIVLAAAQLAGIASLEVLELALRLIKEVVENAQREGYDIAVAAIAAAVAFAVVAVAAAAADITSSEVLELAIRLIKEVVENAQREGYVILLAALAAAAAFVVVAAAAKRAGITSSETLKRAIEEIRKRVEEAQREGNDISEAARQAAEEFRKKAEELK**(GSLEHHHHHH) |
| d2.4 SEQ ID NO: 2 | DHR79 | EXT6-DHR62 | bex2c2_G2 | (M)SDEEERNELIKRIREAAQRAREAAERTGDPRVRELARELARIAQIAFYLVLHDPSSSEVNEALKAVVKAIELAVRALEAAEKTGDPRVRELAREVVKAAVDVAEAAQAGLNDKLREVAEKALRLAKEALKEGDSTAAELAAEIARLAAKLAGDEDVLKKVKLVLEAIKLV**KIVVENAKRKGDDSKEAAEAAVAAFLIVLAAAKLAGIASEEVLELAARLIKEVVENAQREGYDIAVAAIAAAVAFAVVAVAAAAADITSSEVLELAIRLIKEVVENAQREGYVILLAALAAAAAFVVVAAAAKRAGITSSETLKRAIEEIRKRVEEAQREGNDISEAARQAAEEFRKKAEELK**(GSLEHHHHHH) |
| d2.7 SEQ ID NO: 3 | DHR79 | DHR76 | bex2c2_G3 | (M)SDEEERNELIKRIREAAQRAREAAERTGDPRVRELARELAKLAQIAFYLVLHDPSAKEVNLALELIVKAIELAVRALEEAEKTGDPHARELAREIVRLAVELARAVAEAAEEAKKQGNSELAEQVARAAQVALEVIKAAITAAKQGDRKAFRAALELVLEVIKAIEEAVKQGNPKKVAEVAL**KAELIRIVVQNAANKGDDADEAVEAARAAFEIVLAAAQLAGIDSEEVLELAARLIKEVVENAQREGYDIAVAAIAAAVAFAVVAVAAAAADITSSEVLELAIRLIKEVVENAVREGYVILLAALAAAAAFVVVAAAAKRAGITSSETLKRAIEEIRKRVEEAQREGNDISEAARQAAEEFRKKAEELK**(GSLEHHHHHH) |
| t32.4_old SEQ ID NO: 4 | Protein A | EXT6-DHR70 | tj04c3_int5v2 | (M)FNKSQQSAFYLILNMPNLNEAQRNGFIQSLKDDPAKSEVVAGEAAIEAARNASKKGSPETAREAVRLALELVQEAARVARKTGSTELLIAAAKLAIEVARVALKVGSPEAAREAVRAALELVQELIRAARKTGSKEVLEEAAKLALEVALVAAAVGSSEAA**AKAVATAVEALKEAGASEDEIAEIVARVISEVIRILKENGSEYKVICVSVAKIVAEIVEALKRSGTSEDEIAEIVARVISEVIRTLKESGSDYLIICVCVAIIVAEIVEALKRSGTSEDEIAEIVARVISEVIRTLKESGSSYEVIKECVQIIVLAIILALMKSGTEVEEILLILLRVKTEVRRTLKESGS**(GSLEHHHHHH) |
| t32.4 (akat.4_r1) SEQ ID NO: 5 | Protein A | EXT6-DHR70 | tj04c3 1 int5v2 | (M)FNKSQQSAFYLILNMPNLNEAQRNGFIQSLKDDPSKSEVVAGEAAIEAARNALKKGSPETAREAVRLALELVQEAERQARKTGSTERLIAAAKLAIEVARVALKVGSPETAREAVRTALELVQELIRQARKTGSKEVLEEAAKLALEVAKVAAEVGSPETA**ARAVATAVEALKEAGASEDEIAEIVARVISEVIRILKESGSEYKVICRAVARIVAEIVEALKRSGTSEDEIAEIVARVISEVIRTLKESGSDYLIICVCVAIIVAEIVEALKRSGTSEDEIAEIVARVISEVIRTLKESGSSYEVIKECVQIIVLAIILALMKSGTEVEEILLILLRVKTEVRRTLKES**(GSLEHHHHHH) |

TABLE 1-continued

Sequences and original building blocks used for all designs.

| Name | Fc binder (under-lined) | Monomer (standard font) | Oligomer (bold font) | Sequence |
|---|---|---|---|---|
| t32.8 SEQ ID NO: 6 | Protein A | EXT6-DHR39 | tj04C3_int5v2 | (M)FNKDQQSAFYEVLNMPNLNEAQRNGFIQSLKDDPSQSLKILIKAAAGGDSELEEVAKRIVKELAEQGRSEKEAAKEAAELIERITRAAGGNSDLIELAVRIVKILEEQGRSPSEAAKEAVEAIEAIVRAAGGDSEA**IKVAAEIAKTIITQKESGSEYKEICRTVARIVAEIVEKLKRNGASEDEIAEIVAAIIAAVILTLKLSGSDYLIICVCVAIIVAEIVEALKRSGTSEDEIAEIVARVISAVIRVLKESGSSYEVIKECVQIIVLAIILALMKSGTEVEEILLILLRVKTEVRRTLKES**(GSLEHHHHHH) |
| o42.1 SEQ ID NO: 7 | Protein | EXT6-ADHR9 | tj10C4_G1 | (M)FNKDQQSAFYEILNMPNLNEALRNGFIQLLKDDPSKSTVILTAAKVAAELSEKIRTLKESGSSYEQIAETVAKAVAKLVEKLKRNGVSEDEIALAVALIISAVIQTLKESGSSYEVIAEIVARIVAEIVEALKRSGTSEDEIAEIVARVISEVIRTLKESGSSYEVIAEIVARIVAEIVEALKRSGTSEDEIAKIVARVIAEVLRTLKESGSSEEVIKEIVARIITEIKEALKRSGTSEDEIELITLMIEAALEI**AKLKSSGSEYEEICEDVARRIAELVEKLKRDGTSAVEIAKIVAAIISAVIAMLKASGSSYEVICECVARIVAEIVEALKRSGTSAAIIALIVALVISEVIRTLKESGSSFEVILECVIRIVLEITEALKRSGTSEQDVMLIVMAVLLVVLATLQLS**(GSLEHHHHHH) |
| i52.3 SEQ ID NO: 8 | DHR79 | EXT6-DHR71 | 5H2LD-10_5 | (M)SDEEERNELIKRIREAAQRAREAAERTGDPRVRELARELARLAQRAFYLVLHDPSSSDVNEALKLIVEAIEAAVRALEAAERAGDPELREDAREAVRLAVEAAEEVQRNPSSSTANLLLKAIVALAEALAAAANGDKEKFKKAAESALEIAKRVVEVASKEGDPEAVLEAAKVALRVAELAAKNGDKEVFKKAAESALEVAKRLVEVASKEGDPELVLEAAKVALRVAELAAKNGDKEVFQKAAASAVEVALRLTEVASKEGDSELETEAAKVITRVRELASKQGDAA**VAILAETAEVKLEIEESKKRPQSESAKNLILIMQLLINQIRLLVLQIRMLDEQRQE**(GSLEHHHHHH) |
| i52.6 SEQ ID NO: 9 | DHR79 | EXT6-DHR57 | 5H2LD-10_5 | (M)SDEEERNELIKRIREAAQRAREAAERTGDPRVRELARELARLAQRAFYLVLHDPSSSDVNEALKLIVEAIEAAVRALEAAERTGDPKVREEARELVRRAVEAAEEVQRNPSSSEVNEKLKAIVVEIEVKVASLEAKEVTDPDKALKIAKKVIELALEAVKENPSTEALRAVLEAVRLASEVAKRVTDPDKALKIAKLVIELALEAVKEDPSTDALRAVLEAVRLASEVAKRVTDPDKALKIAKLVLELAAEAVKEDPSTDALRAAKEAERLATEVAKRVTDPKKAREIEML**VLKLQMEAILAETEEVKKEIEESKKRPQSESAKNLILIMQLLINQIRLLALQIRMLALQLQE**(GSLEHHHHHH) |

As detailed in the examples that follow, the monomers comprise 3 domains (as reflected in the columns of Table 1):

(1) An (Fc) binding domain;

(2) A helical polypeptide (monomer) that helps position the Fc-binder domain and oligomer domain at the correct orientation to promote higher order structures (sometimes referred to as cages, or nanoparticles); and (3) An oligomer domain that can associate via non-covalent interactions to form polymers (including but not limited to homo-polymers), such as dimers, trimers, tetramers, or pentamers (C2, C3, C4, or C5 cyclic symmetry, respectively).

In some embodiments, the oligomer domain can self-associate via non-covalent interactions to form a homo-polymer with an identical polypeptide. In another embodiment, the oligomer domain can associate via non-covalent interactions to form a pseudo-polymer with similar polypeptide that has some amino acid sequence differences, so long as each monomer has the required amino acid sequence identity to the reference polypeptide.

The polypeptide monomers fuse these domains at an orientation that when in oligomeric form and combined with IgG, forms the desired higher order structures as detailed herein.

Each polypeptide monomer has two interfaces: (1) A Fc-binding interface (defined for each polypeptide in Table 3); and (2) An oligomerization domain interface (defined for each polypeptide in Table 2). The polypeptides of the disclosure, when expressed, will form a cyclic oligomer with C2, C3, C4, or C5 symmetry via the oligomerization domain. When combined with antibody or dimer, a higher order, cage-like, polyhedral structure spontaneously assembles via interaction of the antibodies with Fc binding interfaces. The resulting higher order structures have C2 cyclic symmetry at the Fc position and cyclic 2, 3, 4, or 5-symmetry at each oligomerization domain interface. The resulting particles form precisely ordered and structurally homogeneous antibody-bound nanoparticle structures.

As used herein, a Tie-2 antibody "antibody" includes reference to full length and any functional antibody fragments (i.e.: that selectively bind to the Tie 2 receptor) including the Fc domain. In some embodiments, the antibody includes heavy and light chains. In other embodiments, the antibody may comprise a fusion protein comprising a protein that selectively bind to the Tie 2 receptor and an Fc domain, that dimerizes since the Fc domains naturally dimerizes. In other embodiments, the antibody may comprise an Fc fragment chemically modified to a protein that selectively bind to the Tie 2 receptor, which dimerizes since the Fc domains naturally dimerizes.

The Tie-2 dimers include two monomers of the fibrinogen-like domain derived from angiopoietin (F domain) fused to an Fc domain. The two monomers dimerize since the Fc domain naturally dimerizes. The F domain amino acid sequence present in each monomer comprises or consists of the amino acid sequence of SEQ ID NO: 10:

(SEQ ID NO: 10)

```
KAELASEKPFRDCADVYQAGFNKSGIYTIYINNMPEPKKVECNMDVNGG
GWTVIQHREDGSLDFQRGWKEYKMGFGNPSGEYWLGNEFIFAITSQRQY
MLRIELMDWEGNRAYSQYDRFHIGNEKQNYRLYLKGHTGTAGKQSSLIL
HGADFSTKDADNDNCMCKCALMLTGGWWFDACGPSNLNGMFYTAGQNHG
KLNGIKWHYFKGPSYSLRSTTMMIRPLDF.
```

When combined with Tie2 antibodies or the dimers, a higher order, cage-like, polyhedral structure spontaneously assembles via interaction of the antibodies or dimers with Fc binding interfaces. The resulting higher order structures have cyclic symmetry at each Fc-binding interface and each oligomerization domain interface. For example, the Tie2 antibody heavy and light chains can be co-expressed in cells to produce the Tie2 antibody, which can then be mixed with the polymers to form the particles of the disclosure. Alternatively, the Tie2-binding domain fused to an Fc domain can be expressed in cells, which associate to form the dimer, which can then be mixed with the polymers to form the particles of the disclosure In one embodiment, amino acid residues that would be present at a polymeric interface (as defined in Table 2) in a polymer of the polypeptide monomer of any one of SEQ ID NOS:1-9 are conserved (i.e.: identical to the amino acid residue at the same position in the reference polypeptide).

TABLE 2

Predicted interface residues at oligomeric interface (i.e., not the Fc/Fc-binder interface) by residue position

| Name | Interface residues postions |
|---|---|
| d2.3 SEQ ID NO: 1 | 122, 185, 188, 189, 192, 195, 196, 199, 200, 202, 203, 204, 234, 235, 238, 239, 242, 245, 246, 249, 250, 252, 253, 280, 281, 282, 284, 285, 288, 292, 295, 296, 299, 303, 338 |
| d2.4 SEQ ID NO: 2 | 185, 188, 189, 192, 195, 196, 199, 200, 202, 203, 235, 238, 239, 242, 245, 246, 249, 250, 252, 253, 280, 281, 282, 284, 285, 288, 292, 295, 296, 299, 303, 338 |
| d2.7 SEQ ID NO: 3 | 202, 205, 206, 209, 213, 216, 217, 219, 220, 221, 251, 252, 255, 256, 259, 262, 263, 266, 267, 269, 270, 297, 298, 299, 301, 302, 305, 309, 312, 313, 316, 320, 355 |
| t32.4_old SEQ ID NO: 4 | 202, 203, 204, 207, 208, 252, 254, 255, 258, 261, 262, 265, 266, 269, 278, 308, 312, 315, 316, 318, 319, 320, 322, 323, 325, 326, 327, 328, 329, 330, 331, 332, 333, 335, 336, 337, 339, 340, 343 |
| t32.4 (aka t.4_r1) SEQ ID NO: 5 | 202, 203, 204, 207, 208, 252, 254, 255, 258, 261, 262, 265, 266, 269, 278, 308, 312, 315, 316, 318, 319, 320, 322, 323, 325, 326, 327, 328, 329, 330, 331, 332, 333, 335, 336, 337, 339, 340, 343 |
| t32.8 SEQ ID NO: 6 | 155, 156, 157, 160, 161, 205, 207, 208, 211, 214, 215, 218, 219, 222, 231, 232, 261, 265, 268, 269, 271, 272, 273, 275, 276, 278, 279, 280, 281, 282, 283, 284, 285, 286, 288, 289, 290, 292, 293, 296 |
| o42.1 SEQ ID NO: 7 | 288, 289, 290, 294, 338, 339, 340, 341, 343, 344, 348, 364, 368, 369, 372, 373, 375, 376, 379, 383, 388, 389, 390, 391, 392, 393, 394, 395, 396, 397, 398, 400, 401, 402, 404, 405, 408, 409, 412 |
| i52.3 SEQ ID NO: 8 | 201, 205, 209, 236, 248, 252, 255, 277, 281, 282, 284, 286, 287, 289, 290, 293, 294, 297, 300, 301, 304, 305, 307, 308, 309, 310, 311, 312, 313, 314, 315, 316, 318, 319, 320, 321, 322, 323, 324, 325, 326, 327, 328, 329, 330, 331, 332, 333, 334, 335, 336, 337, 338, 339, 340, 341, 343 |
| i52.6 SEQ ID NO: 9 | 203, 206, 276, 282, 285, 288, 289, 292, 293, 295, 296, 299, 302, 303, 306, 309, 310, 313, 314, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352 |

In another embodiment, amino acid residues in the monomers present at a Fc binding interface as defined in Table 3 are conserved.

TABLE 3

| Name | Fc binder used in design | Interface residue positions |
|---|---|---|
| d2.3 SEQ ID NO: 1 | DHR79 | 4, 7, 8, 11, 12, 14, 15, 18, 19, 22, 35, 41, 42, 44, 45, 46, 48, 49, 50, 52, 53 |
| d2.4 SEQ ID NO: 2 | DHR79 | 4, 7, 8, 11, 12, 14, 15, 18, 19, 22, 35, 41, 42, 44, 45, 46, 48, 49, 50, 52, 53 |
| d2.7 SEQ ID NO: 3 | DHR79 | 4, 7, 8, 11, 12, 14, 15, 18, 19, 22, 35, 41, 42, 44, 45, 46, 48, 49, 50, 52, 53 |
| t32.4_old SEQ ID NO: 4 | Protein A | 2, 3, 4, 6, 7, 8, 10, 11, 14, 21, 24, 25, 28, 32 |
| t32.4 (aka t.4_r1) SEQ ID NO: 5 | Protein A | 2, 3, 4, 6, 7, 8, 10, 11, 14, 21, 24, 25, 28, 32 |
| t32.8 SEQ ID NO: 6 | Protein A | 2, 3, 4, 6, 7, 8, 10, 11, 14, 21, 24, 25, 28, 32 |
| o42.1 SEQ ID NO: 7 | Protein A | 2, 3, 4, 6, 7, 8, 10, 11, 14, 21, 24, 25, 28, 32 |
| i52.3 SEQ ID NO: 8 | DHR79 | 4, 7, 8, 11, 12, 14, 15, 18, 19, 22, 35, 41, 42, 44, 45, 46, 48, 49, 50, 52, 53 |
| i52.6 SEQ ID NO: 9 | DHR79 | 4, 7, 8, 11, 12, 14, 15, 18, 19, 22, 35, 41, 42, 44, 45, 46, 48, 49, 50, 52, 53 |

In a further embodiment, amino acid substitutions relative to the reference monomer amino acid sequence comprise, consist essentially of, or consist of substitutions at polar residues in the reference polypeptide. In other embodiments, polar residues on the surface of the polypeptide monomer that are not at the Fc or oligomeric interfaces may be substituted with other polar residues while maintaining folding and assembly properties of the designs.

As used herein, "polar" residues are C, D, E, H, K, N, Q, R, S, T, and Y. "Non-polar" residues are defined as A, G, I, L, M, F, P, W, and V.

In one embodiment, amino acid substitutions relative to the reference monomer amino acid sequence comprise, consist essentially of, or consist of substitutions at polar residues at non-Gly/Pro residues in loop positions, as defined in Table 4, in the reference polypeptide monomer.

TABLE 4

Predicted secondary structure for all listed designs, using pyrosetta's display_secstruct() function. L = Loop, H = Helix

| Name | Sequence |
|---|---|
| d2.3 (SEQ ID NO: 1) | LLHHHHHHHHHHHHHHHHHHHHHHHHHHLLHHHHHHHHHHHHHHHHHHHHHHHLLLHHHHHHHHHHHHHHHHHHHHH<br>HHHHHHHLLHHHHHHHHHHHHHHHHHHHHHHHLLHHHHHHHHHHHHHHHHHHHHHLLHHHHHHHHHHHHHHHHHHLL<br>HHHHHHHHHHHHHHHHHHHHHHHHHHHHLLLHHHHHHHHHHHHHHHHHHHHLLLLHHHHHHHHHHHHHHHHHHHHHH<br>LLLHHHHHHHHHHHHHHHHHHHHHHLLLLHHHHHHHHHHHHHHHHHHHHHLLHHHHHHHHHHHHHHHHHHHHHHHLL<br>LLHHHHHHHHHHHHHHHHHHHHHLLLHHHHHHHHHHHHHHHHHHHHHLLLLLLLLLL |
| d2.4 (SEQ ID NO: 2) | LLHHHHHHHHHHHHHHHHHHHHHHHHHHLLHHHHHHHHHHHHHHHHHHHHHHHLLLHHHHHHHHHHHHHHHHHHHHH<br>HHHHHHHLLHHHHHHHHHHHHHHHHHHHHHHHLLHHHHHHHHHHHHHHHHHHHHHLLHHHHHHHHHHHHHHHHHHLL<br>HHHHHHHHHHHHHHHHHEHHHHHHHHHHLLLHHHHHHHHHHHHHHHHHHHHLLLLHHHHHHHHHHHHHHHHHHHHHH<br>LLLHHHHHHHHHHHHHHHHHHHHHHLLLLHHHHHHHHHHHHHHHHHHHHHLLHHHHHHHHHHHHHHHHHHHHHHHLL<br>LLHHHHHHHHHHHHHHHHHHHHHLLLHHHHHHHHHHHHHHHHHHHHHLLLLLLLLLL |
| d2.7 (SEQ ID NO: 3) | LLHHHHHHHHHHHHHHHHHHHHHHHHHHLLHHHHHHHHHHHHHHHHHHHHHHHLLLHHHHHHHHHHHHHHHHHHHHH<br>HHHHHHHLLHHHHHHHHHHHHHHHHHHHHHHHHHHHHHHLHHHHHHHHHHHHHHHHHHHHHHHHHHHHHLLHHHHH<br>HHHHHHHHHHHHHHHHHHLLHHHHHHHHHHHHHHHHHHHHHHHHHHHHHHLLLHHHHHHHHHHHHHHHHLLLLHHHH<br>HHHHHHHHHHHHHHHHLLLHHHHHHHHHHHHHHHHHHHHHHHLLLHHHHHHHHHHHHHHHHHHHHHHHHLLHHHHHH<br>HHHHHHHHHHHHHHHLLLLHHHHHHHHHHHHHHHHHHHHHLLHHHHHHHHHHHHHHHHHHHHLLLLLLLLLLLL |
| t32.4_ old (SEQ ID NO: 4) | LLLHHHHHHHHHHHHHLLLLHHHHHHHHHHHHHLHHHHHHHHHHHHHHHHHHHHHHLLHHHHHHHHHHHHHHHHHHH<br>HHHHHHLLHHHHHHHHHHHHHHHHHHHHHLLHHHHHHHHHHHHHHHHHHHHHHHHHLLHHHHHHHHHHHHHHHHHHH<br>HHLLHHHHHHHHHHHHHHHHHLLLHHHHHHHHHHHHHHHHHHHHHHLLLHHHHHHHHHHHHHHHHHHHHHHLLLLHH<br>HHHHHHHHHHHHHHHHHHHLLLHHHHHHHHHHHHHHHHHHHHHHHLLHHHHHHHHHHHHHHHHHHHHHHHLLLHHHH<br>HHHHHHHHHHHHHHHHLLLLHHHHHHHHHHHHHHHHHHHHHHHLLLLLLLLLLLLL |
| t32.4 (aka t.4_r1) (SEQ ID NO: 5) | LLLHHHHHHHHHHHHHLLLLHHHHHHHHHHHHHLHHHHHHHHHHHHHHHHHHHHHHLLHHHHHHHHHHHHHHHHHHH<br>HHHHHHLLHHHHHHHHHHHHHHHHHHHHHLLHHHHHHHHHHHHHHHHHHHHHHHHHLLHHHHHHHHHHHHHHHHHHH<br>HHLLHHHHHHHHHHHHHHHHHLLLHHHHHHHHHHHHHHHHHHHHHHLLLHHHHHHHHHHHHHHHHHHHHHHLLLLHH<br>HHHHHHHHHHHHHHHHHHHLLLHHHHHHHHHHHHHHHHHHHHHHHLLHHHHHHHHHHHHHHHHHHHHHHHLLLHHHH<br>HHHHHHHHHHHHHHHHLLLLHHHHHHHHHHHHHHHHHHHHHHHLLLLLLLLLLLLL |
| t32.8 (SEQ ID NO : 6) | LLLHHHHHHHHHHHHLLLLHHHHHHHHHHHHHHLHHHHHHHHHHHHHLLHHHHHHHHHHHHHHHHHHHLLHHHHHHH<br>HHHHHHHHHHHLLLHHHHHHHHHHHHHHHHHHHLLLHHHHHHHHHHHHHHHHHHHHLLLHHHHHHHHHHHHHHHHHL<br>LLLHHHHHHHHHHHHHHEHHHHHLLLLHHHHHHHHHHHHHHHHHHHHHHHHLLLLHHHHHHHHHHHHHHHHHHHHLL<br>LHHHHHHHHHHHHHHHHHHHHHLLLHHHHHHHRHHHHHHHHHHHHHHLLLLHHHHHHHHHHHHHHHHHHHHHHLLLL<br>LLLLLLLLL |
| o42.1 (SEQ ID NO: 7) | LLLHHHHHHHHHHHHLLLLHHHHHHHHHHHHHHLHHHHHHHHHHHHHHHHHHHHHHHHHHLLLHHHHHHHHHHHHHH<br>HHHHHHHHLLLLHHHHHHHHHHHHHHHHHHHHHHLLHHHHHHHHHHHHHHHHHHHHHHLLLLHHHHHHHHHHHHHHH<br>HHHHHHHLLLHHHHHHHHHHHHHHHHHHHHHHLLLHHHHHHHHHHHHHHHHHHHHHHHLLHHHHHHHHHHHHHHHHH<br>HHHHLLLLHHHHHHHHHHHHHHHHHHHHHHHLLLHHHHHHHHHHHHHHHHHHHHHHHLLHHHHHHHHHHHHHHHHHH<br>HHHHLLLHHHHHHHHHHHHHHHHHHHHHHHLLLHHHHHHHHHHHHHHHHHHHHHHHLLHHHHHHHHHHHHHHHHHHH<br>HLLLLHHHHHHHHHHHHHHHHHHHHHHHHHLLLLLLLLLL |
| i52.3 (SEQ ID NO: 8) | LLHHHHHHHHHHHHHHHHHHHHHHHHHHHLLHRHHHHHHHHHHHHHHHHHHHHHHHLLLLHHHHHHHHHHHHHHHHH<br>HHHHHHHLLHHHHHHHHHHHHHHHHHHHHHHHHHLLLLHHHHHHHHHHHHHHHHHHHHLLHHHHHHHHHHHHHHHHH<br>HHHHHHHHLLHHHHHHHHHHHHHHHHHHHHHLHHHHHHHHHHHHHHHHHHHHHHHHHLLHHHHHHHHHHHHHHHHHH<br>HHHHLLHHHHHHHHHHHHHHHHHHHHHHHHHLHHHHHHHHHHHHHHHHHHHHHHLHHHHHHHHHHHHHHHHHHHHHH<br>LLLLHHHHHHHHHHHHHHHHHHHHHHHHHHHHHHHHHHLLLLLLLLLL |
| i52.6 (SEQ ID NO: 9) | LLLHHHHHHHHHHHHHLLLLHHHHHHHHHHHHHLHHHHHHHHHHHHHHHHHHHHHHLLHHHHHHHHHHHHHHHHHHH<br>HHHHHHLLHHHHHHHHHHHHHHHHHHHHHLLHHHHHHHHHHHHHHHHHHHHHHHHHLLHHHHHHHHHHHHHHHHHHH<br>HHLLHHHHHHHHHHHHHHHHHLLLHHHHHHHHHHHHHHHHHHHHHHLLLHHHHHHHHHHHHHHHHHHHHHHLLLLHH<br>HHHHHHHHHHHHHHHHHHHLLLHHHHHHHHHHHHHHHHHHHHHHHLLHHHHHHHHHHHHHHHHHHHHHHHLLLHHHH<br>HHHHHHHHHHHHHHHHLLLLHHHHHHHHHHHHHHHHHHHHHHHLLLLLLLLLLLLL |

In a further embodiment of any of these embodiments, amino acid changes from the reference polypeptide monomer are conservative amino acid substitutions. As used here, "conservative amino acid substitution" means that:

hydrophobic amino acids (Ala, Cys, Gly, Pro, Met, Sce, Sme, Val, Ile, Leu) can only be substituted with other hydrophobic amino acids;

hydrophobic amino acids with bulky side chains (Phe, Tyr, Trp) can only be substituted with other hydrophobic amino acids with bulky side chains;

amino acids with positively charged side chains (Arg, His, Lys) can only be substituted with other amino acids with positively charged side chains;

amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

In all embodiments disclosed herein, the polypeptides may comprise one or more additional functional groups or residues as deemed appropriate for an intended use. The polypeptides of the disclosure may include additional residues at the N-terminus or C-terminus, or a combination thereof; these additional residues are not included in determining the percent identity of the polypeptides of the invention relative to the reference polypeptide. Such residues may be any residues suitable for an intended use, including but not limited to detectable proteins or fragments thereof (also referred to as "tags"). As used herein, "tags" include general detectable moieties (i.e.: fluorescent proteins, antibody epitope tags, etc.), therapeutic agents, purification tags (His tags, etc.), linkers, ligands suitable for purposes of purification, ligands to drive localization of the polypeptide, peptide domains that add functionality to the polypeptides. In non-limiting embodiments, such functional groups may comprise one or more polypeptide antigens, polypeptide therapeutics, enzymes, detectable domains (ex: fluorescent proteins or fragments thereof), DNA binding proteins, transcription factors, etc. In one embodiment, the polypeptides may further comprise a functional polypeptide covalently linked to the amino-terminus and/or the carboxy-terminus. In other embodiments, the functional polypeptide may include, but is not limited to, a detectable polypeptide such as a fluorescent or luminescent polypeptide, receptor binding domains, etc.

In one embodiment, the plurality of homo-polymers comprises homo-dimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-3. In these embodiments, adding the recited polypeptides with Tie2 antibodies or dimers results in spontaneous assembly into a D2 dihedral structure containing two antibodies per particle.

In another embodiment, the plurality of homo-polymers comprises homo-trimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:4-6. In these embodiments, adding the recited polypeptides with Tie2 antibodies or dimers results in spontaneous assembly into a T32 tetrahedral structure containing six antibodies per particle.

In a further embodiment, the plurality of homo-polymers comprises homo-tetramers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7. In these embodiments, adding the recited polypeptides with Tie2 antibodies or dimers results in spontaneous assembly into an 042 octahedral structure containing twelve antibodies per particle.

In a still further embodiment, the plurality of homo-polymers comprises homo-pentamers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:8-9. In these embodiments, adding the recited polypeptides with Tie2 antibodies or dimers results in spontaneous assembly into an 152 icosahedral structure containing thirty antibodies per particle.

In one embodiment of all of these embodiments, the Tie2 antibodies or dimers comprise Tie 2 antibodies, wherein the Tie-2 antibodies comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of:

SEQ ID NOS: 11-12,
SEQ ID NOS: 13-14, and
SEQ ID NOS: 15-16.

12H8 heavy chain (FC domain underlined)

(SEQ ID NO: 11)

EVQLVESGGGLVKPGGSLKLSCAASGFTPSDYGMHWVRQAPEKGLEWVAYINSGSSTITYADTVKGRFTISRDNA

KNTLFLQMTSLRSEDTAIYYCARGYYGPYYFDYWGQGTALTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSSDKT

HTCPPCPAPELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALHNHYTQKSLSLSPGK light chain (SEQ ID NO: 12)

DIVMTQSHKFMSTSVGDRVSFTCKASQNVGTAVAWYQQKPGQSPKLLIYWASSRHTGVPDRFTGSGSGTDFTLTI

TNVQSEDLADYFCQEYSSYPLTFGVGTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

-continued

13H10
heavy chain (Fc domain underlined)
(SEQ ID NO: 13)
QVQLQQSGPELKKPGETVKISCKASGYTETDFSIHWVKQAPGKGLKWMGWINTETGETTYAEDFKGRFAFSLETS

ASTAYLQINNLKNEDTATYFCSRRYDYDTWFAYWGQGTLVTVSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKSSDKTH

TCPPCPAPELLGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNHYTQKSLSLSPCK light chain
(SEQ ID NO: 14)
DIVMTQAALSVPVTPGESVSISCRSSSSLLHRRGNTYLYWFLQRPGQSPQLLIYRMSNLASGVPDRFSGSGSGTA

FTLRISRVEAEDVGVYYCMQRLEYPFTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGEC

15B8
(SEQ ID NO: 15)
heavy chain (FC domain underlined)
QVQLQQPGVVLVMPGASVKLSCKASGYTFASYWMHWVKQRPGQGLEWIGEIDPSDSYRNYNQKFKGKATLTVDKS

SSTVNMQLSSLTSEDSAVYYCAKTSGIGRAMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKKVEPKSSDKT

HTCPPCPAPELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQVSLTCLVKGFY

PSDIAVEWESNGQPEMNYKTTPPVLDSDGSFFLYSKLTVDKSRWQQGNVFSCSVMHEALHNHYTQKSLSLSPGK light chain
(SEQ ID NO: 16)
DIQMIQSPASLSASVCETVTITCRASENIYSFVTWYQQKQGKSPQLLVFNAKNLVEGVPSSFSGSGSGTQFSLKI

DSLQPEDFGTYYCQHHYSIPYTFGGGTKLEMRRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

In another embodiment of all of these embodiments, the Tie2 antibodies or dimers comprise dimers, wherein the dimers comprise monomers comprising the amino acid sequence of SEQ ID NO:47, wherein (X) is optional and when present comprises an amino acid linker of any suitable length and amino acid content. As noted above, the Tie-2 dimers include two monomers of the fibrinogen-like domain derived from angiopoietin (F domain) fused to an Fc domain. The two monomers dimerize since the Fc domain naturally dimerizes. The F domain amino acid sequence present in each monomer comprises or consists of the amino acid sequence of SEQ ID NO:10:

Human Ang1 F Domain (Tie2 Receptor Binding Domain; SEQ ID NO:10): Bold Font Human IgG1 Fc: Underlined (SEQ ID NO: 47)
KAELASEKPFRDCADVYQAGFNKSGIYTIYINNMPEPKKVECNMDVNGGGWTVIQHREDGSLDFQRGWKEYKMGE

GNPSGEYWLGNEFIFAITSQRQYMLRIELMDWEGNRAYSQYDRFHIGNEKQNYRLYLKGHTGTAGKQSSLILEGA

DFSTKDADNDNCMCKCALMLTGGWWFDACGPSNLNGMFYTAGQNHGKLNGIRWHYFKGPSYSLRSTTMMIRPLDF

(X) EPKSSDKTHTCPPCPAPELLGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCSVMHEALHNHYT

QKSLSLSPGK

In one embodiment, the dimers comprise monomers comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of the amino acid sequence of SEQ ID NO:17 or 18, wherein residues in parentheses are optional. The residues in parentheses are either amino acid linkers (in these examples, GS-rich linkers), His-tags, or secretion signals (italicized—these may be absent, present, or replaced with any other secretion signal)

(SEQ ID NO: 17)

(*METDTLLLWVLLLWVPGSTG*)(HHHHHH)(GGS)KAELASEKPFRDCADVYQAGFNKSGIYTIYINNMPEPKKV
FCNMDVNGGGWTVIOHREDGSLDFQRGWKEYKMGFGNPSGEYWLGNEFIEAITSQRQYMLRIELMDWEGNRAYSQ
YDRFHIGNEKQNYRLYLKGHTGTAGKQSSLILHGADFSTKDADNDNCMCKCALMLTGGWWFDACGPSNLNGMFYT
AGQNHGKLNGIKWHYEKGPSYSLRSTTMMIRPLDE(GGSGGS)EPKSSDKTHTCPPCPAPELLGGPSVFLFPPKP
KDTLMISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSPDELTSNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO: 18)

(*METDTLLLWVLLLWVPGSTG*)KAELASEKPFRDCADVYQAGFNKSGIYTIYINNMPEPKKVFCNMDVNGGGWTV
IQHREDGSLDFQRGWKEYKMGFGNPSGEYWLGNEFIFAITSQRQYMLRIELMDWEGNRAYSQYDRFHIGNEKQNY
RLYLKGHTGTAGKQSSLILHGADFSTKDADNDNCMCKCALMLTGGWWFDACGPSNLNGMFYTAGQNHGKLNGIKW
HYFKGPSYSLRSTTMMIRPLDF(GGSGGS)EPKSSDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPAPIEKT
ISKAKGQPREPWVTTLEPSRDELTKNGVSLTCLVEGFYPSDIAVEWESNGQPENNYKTTPPVLDSDGSFFLYSKL
TVDKSRWQQGNWFSCSVMHEALHNHYTQESLSLSPGK(GGSHHHHHH)

In one specific embodiment of any of the above embodiments, the plurality of homo-polymers comprises homo-tetramers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7. In another specific embodiment of any of the above embodiments, the plurality of homo-polymers comprises homo-trimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5.

In another embodiment, the disclosure provides composition comprising a plurality of the particles of any embodiment herein comprising Tie2 receptor antibodies comprising Fc domains, and/or dimers of fibrinogen-like domain derived from angiopoietin (F domain) fused to an Fc domain. The compositions may be used, for example, in the methods and uses of the disclosure. In one embodiment, all antibodies or dimers in the composition are identical. In another embodiment, the antibodies or dimers in the composition are, in total, not identical. For example, the composition may comprise particles comprising Tie2 antibodies and particles comprising F domain dimers. In another embodiment, the composition may comprise particles comprising different Tie2 antibodies and/or F domain dimers having different amino acid sequences.

In another embodiment, the disclosure comprises pharmaceutical compositions comprising the Tie2 particle or composition of any embodiment herein, and a pharmaceutically acceptable carrier. The pharmaceutical compositions may be used, for example, in the methods and uses of the disclosure.

In another embodiment, the disclosure provides uses of the Tie 2 particles, compositions or pharmaceutical compositions for any suitable use, including but not limited to those described in the examples. In one embodiment, the disclosure provides methods for treating complications from bacterial or viral infections or any disease or syndrome resulting from vascular dysfunction, comprising administering to a subject having a bacterial or viral infection or any disease or syndrome resulting from vascular dysfunction an amount of the particles, compositions, or pharmaceutical compositions or any embodiment or combination of embodiments herein effective to treat the bacterial or viral infection. The methods may be used to treat any bacterial or viral infection, or any disease or syndrome resulting from vascular dysfunction as deemed appropriate by attending medical personnel. In one embodiment, the treating comprising treating or limiting development of diseases or syndromes resulting from vascular dysfunction, including but are not limited to sepsis, acute respiratory distress syndrome (ARDS), acute lung injury, acute kidney injury, wet-age related macular degeneration, open angle glaucoma, diabetic retinopathy, and diabetic nephropathy.

In another embodiment, the disclosure provides kits for generating the particles and compositions of the disclosure. In one embodiment, the kits comprise:

(a) a polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally wherein the polypeptides are as disclosed in any embodiment disclosed herein; and (b) Tie2 antibodies comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of SEQ ID NOS:11-12; SEQ ID NOS: 13-14; and SEQ ID NOS:15-16, and/or a fibrinogen-like domain derived from angiopoietin (F domain) fused to an Fc domain optionally comprising the amino acid sequence selected from the group consisting of SEQ ID NOS:17-18 and 47.

In this embodiment, when the two components are combined the particles spontaneously assemble via interaction of the antibodies or dimers with Fc binding interfaces.

In another embodiment, the kits comprise:

(a) host cells capable of expressing a polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS: 1-9, wherein residues in parentheses are optional (i.e.: not considered in the percent identity requirement), wherein the polypeptide is capable of (a) assembling into a homo-polymer, and (b) binding to a constant region of an IgG antibody; optionally wherein the polypeptides are as disclosed for any embodiment herein; and (b) host cells capable of expressing Tie2 antibodies amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs selected from the group consisting of SEQ ID NOS:11-12; SEQ ID NOS:13-14; and SEQ ID NOS:15-16, and/or a fibrinogen-like domain derived from angiopoietin (F domain) fused to an Fc domain optionally comprising the amino acid sequence selected from the group consisting of SEQ ID NOS: 17-18 and 47.

In this embodiment, the two components can be produced by the host cells and then combined so that the particles spontaneously assemble via interaction of the antibodies or dimers with Fc binding interfaces.

In another embodiment, the disclosure provides polypeptides comprising an amino acid sequence comprising or consisting of the amino acid sequence of any one of SEQ ID NOS: 17-18 and 47. The polypeptides may be used in producing the Tie 2 particles disclosed herein.

In another aspect, the disclosure provides nucleic acids encoding the polypeptide comprising or consisting of the amino acid sequence of any one of SEQ ID NOS: 17-18 and 47. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In another aspect, the disclosure provides expression vectors comprising the nucleic acids of the disclosure operatively linked to control sequence. "Expression vector" includes vectors that operatively link a nucleic acid coding region or gene to any control sequences capable of effecting expression of the gene product. "Control sequences" operatively linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In a further embodiment, the disclosure provides host cells comprising the polypeptide, nucleic acid, and/or expression vector of any embodiment disclosed herein. In various embodiments, the host cells can be either prokaryotic or eukaryotic.

In another aspect, the disclosure provides particles, comprising:

(a) a plurality of polypeptide polymers, wherein (i) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:1;

(ii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:2;

(iii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:3;

(iv) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:4;

(v) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5;

(vi) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:6;

(vii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7;

(viii) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:8; or (ix) each monomer in the polymers comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:9; wherein residues in parentheses are optional (i.e.: not considered in the percent identity requirement); and (b) a plurality of α-TNFRSF (tumor necrosis factor receptor superfamily) antibodies comprising Fc domains;

wherein (i) each α-TNFRSF antibody in the plurality of antibodies comprises a first Fc domain and a second Fc domain;

(ii) each α-TNFRSF antibody in the plurality of antibodies is (A) non-covalently bound via the first Fc domain to one polypeptide monomer chain of a first polymer, and (B) non-covalently bound via the second Fc domain to one polypeptide monomer of a second polymer; and (iii) each polypeptide monomer chain of each polymer is non-covalently bound to one Fc domain;

wherein the particle comprises dihedral, tetrahedral, octahedral, or icosahedral symmetry.

As shown in the examples that following, the particles of the disclosure targeting cell-surface TNFRSF receptors enhance signaling compared to free antibodies or Fc-fusions in DR5-mediated apoptosis, and were shown to induce tumor cell apoptosis. Thus, the compositions may be used to treat tumors.

In this aspect, "antibody" includes reference to full length and any functional antibody fragments that selectively bind a TNFRSF including the Fc domain; fusion proteins comprising a protein that binds a TNFRSF and an Fc domain, that dimerizes since the Fc domains naturally dimerizes; and an Fc fragment chemically modified to a protein that binds a TNFRSF, which dimerizes since the Fc domains naturally dimerizes.

When combined with α-TNFRSF antibody, a higher order, cage-like, polyhedral structure spontaneously assembles via interaction of the antibodies with Fc binding interfaces. The resulting higher order structures have C2 cyclic symmetry at the Fc position and cyclic 2, 3, 4, or 5-symmetry at each homo-oligomerization domain interface.

All embodiments of the polypeptide monomers disclosed herein are equally applicable to this aspect of the disclosure. Thus, in various non-limiting embodiments, residues present at a polymeric interface, as defined in Table 2, in a polymer of the polypeptide of any one of SEQ ID NOS:1-9 may be conserved; residues present at a Fc binding interface of any one of SEQ ID NOS:1-9 as defined in Table 3 may be conserved; substitutions relative to the reference sequence of any one of SEQ ID NOS:1-9 may comprise, consist essentially of, or consist of substitutions at polar residues in the reference polypeptide; substitutions relative to the reference sequence of any one of SEQ ID NOS:1-9 may comprise, consist essentially of, or consist of substitutions at polar residues at non-Gly/Pro residues in loop positions, as defined in Table 4, in the reference polypeptide; and/or amino acid changes from the reference polypeptide of any one of SEQ ID NOS:1-9 may be conservative amino acid substitutions. In all embodiments, the polypeptide monomers may further comprise a functional polypeptide covalently linked to the amino-terminus and/or the carboxy-terminus. In various non-limiting embodiments, the functional polypeptide may include, but is not limited to, a detectable polypeptide such as a fluorescent or luminescent polypeptide, receptor binding domains, etc.

In one embodiment, the α-TNFRSF antibody heavy and light chains can be co-expressed in cells to produce the α-TNFRSF antibody, which can then be mixed with the polymers to form the particles of the disclosure.

In some embodiments, the polypeptide monomers in each polymer are 100% identical, and the polymers are homo-oligomers. In other embodiments, the polymers may comprise monomers with some amino acid differences, so long as each monomer has the required amino acid sequence identity to the reference polypeptide. In these embodiments, the polymers are not necessarily homo-oligomers. In light of this, as will be understood by those of skill in the art, the plurality of polymers in a given particle may comprise all homo-oligomers, the particle may comprise polymers that are not homo-oligomers, or a combination thereof. Similarly, the particle may comprise all homo-oligomers, and each homo-oligomer may be identical, or the plurality of homo-oligomers may comprise 2 or more different homo-oligomers.

In one embodiment, the plurality of polymers comprises dimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-3. In these embodiments, adding the recited polypeptides with to α-TNFRSF antibodies results in spontaneous assembly into a D2 dihedral structure containing two antibodies per particle.

In another embodiment, the plurality of polymers comprises trimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:4-6. In these embodiments, adding the recited polypeptides with α-TNFRSF antibodies results in spontaneous assembly into a T32 tetrahedral structure containing six antibodies per particle.

In a further embodiment, the plurality of polymers comprises tetramers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7. In these embodiments, adding the recited polypeptides with α-TNFRSF antibodies results in spontaneous assembly into an 042 octahedral structure containing twelve antibodies per particle.

In one embodiment, the plurality of polymers comprises pentamers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:8-9. In these embodiments, adding the recited polypeptides with α-TNFRSF antibodies results in spontaneous assembly into an 152 icosahedral structure containing thirty antibodies per particle.

Any TNFRSF may be targeted as appropriate for an intended use of the particles and compositions thereof. In various embodiments, the α-TNFRSF antibody targets one or more of DR5/TRAIL-R2/TNFRSF10B/CD262, CD40, 4-1BB, and TWEAKR (Tumor Necrosis Factor-like Weak Inducer of Apoptosis Receptor)/TNFRSF12A/CD266. In various further embodiments, the α-TNFRSF antibodies comprise an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of heavy and light chain pairs (when both heavy and light chain are needed) selected from the group consisting of SEQ ID NO: 19 and 20;
SEQ ID NO: 21 and 22;
SEQ ID NO: 23 and 24;
SEQ ID NO: 25 and 26;
SEQ ID NO: 27 and 28;
SEQ ID NO: 29;
SEQ ID NO: 30;
SEQ ID NO: 31 and 32;
SEQ ID NO: 33;
SEQ ID NO: 34 and 35;
SEQ ID NO: 36 and 37;
SEQ ID NO: 38 and 39;
SEQ ID NO: 40 and 41;
SEQ ID NO: 42 and 43;
SEQ ID NO: 44 and 45;
SEQ ID NO: 44 and 46;
SEQ ID NO: 48 and 49;
SEQ ID NO: 50 and 51;
SEQ ID NO: 52 and 53
SEQ ID NO: 54 and 55;
SEQ ID NO: 56;
Lob 7/6 heavy and light chains as disclosed in published US patent application US US20090074711 (incorporated by reference herein in its entirety); and
Heavy and light chain pairs disclosed in 2018094300 (incorporated by reference herein in its entirety).

TABLE 5

| Antibody sequences |
| --- |
| CD40 Targeting antibodies<br>Selicrelumab<br>(Heavy chain)<br>QVQLVQSGAE VKKPGASVKV SCKASGYTFT GYYMHWVRQA PGQGLEWMGW INPDSGGTNY<br>AQKFQGRVTM TRDTSISTAY MELNRLRSDD TAVYYCARDQ PLGYCTNGVC SYFDYWGQGT<br>LVTVSSASTK GPSVFPLAPC SRSTSESTAA LGCLVKDYFP EPVTVSWNSG ALTSGVHTFP<br>AVLQSSGLYS LSSVVTVPSS NFGTQTYTCN VDHKPSNTKV DKTVERKCCV ECPPCPAPPV<br>AGFSVFLFPP KPKDTLMISR TPEVTCVVVD VSHEDPEVQF NWYVDGVEVH NAKTKPREEQ<br>FNSTRFVVSV LTVVHQDWLN GKEYKCKVSN KGLPAPIEKT ISKTKGQPRE PQVYTLPPSR<br>EEMTKNQVSL TCLVKGFYPS DIAVEWESNG QPENNYKTTP PMLDSDGSFF LYSKLTVDKS<br>RWQQGNVFSC SVMHEALHNH YTQKSLSLSP GK (SEQ ID NO: 19) |
| (Light chain)<br>DIQMTQSPSS VSASVGDRVT ITCRASQGIY SWLAWYQQKP GKAPNLLIYT ASTLQSGVPS<br>RFSGSGSGTD FTLTISSLQP EDFATYYCQQ ANIFPLTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC (SEQ ID NO: 20) |
| Bleselumab<br>(Heavy chain)<br>QLQLQESGPG LLKPSETLSL TCTVSGGSIS SPGYYGGWIR QPPGKGLEWI GSIYKSGSTY<br>HNPSLKSRVT ISVDTSKNQF SLKLSSVTAA DTAVYYCTRP VVRYFGWFDP WGQGTLVTVS<br>SASTKGPSVF PLAPCSRSTS ESTAALGCLV KDYFPEPVTV SWNSGALTSG VHTFPAVLQS<br>SGLYSLSSVV TVPSSSLGTK TYTCNVDHKP SNTKVDKRVE SKYGPPCPPC PAPEFEGGPS<br>VFLFPPKPKD TLMISRTPEV TCVVVDVSQE DPEVQFNWYV DGVEVHNAKT KPREEQFNST<br>YRVVSVLTVL HQDQLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSFFLYSR LTVDKSRWQE<br>GNVFSCSVMH EALHNHYTQK SLSLSLGK (SEQ ID NO: 21) |
| (Light chain)<br>AIQLTQSPSS LSASVGDRVT ITCRASQGIS SALAWYQQKP GKAPKLLIYD ASNLESGVPS<br>RFSGSGSGTD FTLTISSLQP EDPATYYCQQ FNSYPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC (SEQ ID NO: 22) |
| 4-1BB Targeting antibodies<br>Urelumab<br>(Heavy chain)<br>QVQLQQWGAG LLKPSETLSL TCAVYGGSFS GYYWSWIRQS PEKGLEWIGE INHGGYVTYN<br>PSLESRVTIS VDTSKNQFSL KLSSVTAADT AVYYCARDYG PGNYDWYFDL WGRGTLVTVS<br>SASTKGPSVF PLAPCSRSTS ESTAALGCLV KDYFPEPVTV SWNSGALTSG VHTFPAVLQS<br>SGLYSLSSVV TVPSSSLGTK TYTCNVDHKP SNTKVDKRVE SKYGPPCPPC PAPEFLGGPS<br>VFLFPPKPKD TLMISRTPEV TCVVVDVSQE DPEVQFNWYV DGVEVHNAKT KPREEQFNST<br>YRVVSVLTVL HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSFFLYSR LTVDKSRWQE<br>GNVFSCSMVH EALHNHYTQK SLSLSGK (SEQ ID NO: 23) |
| (Light chain)<br>EIVLTQSPAT LSLSPGERAT LSCRASQSVS SYLAWYQQKP GQAPRLLIYD ASNRATGIPA<br>RFSCSGSGTD FTLTISSLEP EDFAVYYCQQ RSNWPPALTF CGGTKVEIKR TVAAPSVFIF<br>PPSDEQLKSG TASVVCLLNN FYPREAKVQW KVDNALQSGN SQESVTEQDS KDSTYSLSST<br>LTLSRADYEK HKVYACEVTH QGLSSPVTKS FNRGEC (SEQ ID NO: 24) |

TABLE 5-continued

Antibody sequences

Utomilumab
(Heavy chain)
EVQLVQSGAE VKKPGESLRI SCKGSGYSFS TYWISWVRQM PGKGLEWMGK IYPGDSYTNY
SPSFQGQVTI SADKSISTAY LQWSSLKASD TAMYYCARGY GIFDYWGQGT LVTVSSASTK
GPSVFPLAPC SRSTSESTAA LGCLVKDYFP EPVTVSWNSG ALTSGVHTFP AVLQSSGLYS
LSSVVTVPSS NFGTQTYTCN VDHKPSNTKV DKTVERKCCV ECPPCPAPPV AGPSVFLFPP
KPKDTLMISR TPEVTCVVVD VSHEDPEVQF NWYVDGVEVH NAKTKPREEQ FNSTFRVVSV
LTVVHQDWLN GKEYKCKVSN KGLPAPIEKT ISKTKGQPRE PQVYTLPPSR EEMTKNQVSI
TCLVKGFYPS DIAVEWESNG QPENNYKTTP PMLDSDGSFF LYSKLTVDKS RWQQGNVFSC
SVMHEALHNH YTQKSLSLSP GK (SEQ ID NO: 25)

(Light chain)
SYELTQPPSV SVSPGQTASI TCSGDNIGDQ YAHWYQQKPG QSPVLVIYQD KNRPSGIPER
FSGSNSGNTA TLTISGTQAM DEADYYCATY TGFGSLAVFG GGTKLTVLGQ PKAAPSVTLE
PPSSEELQAN KATLVCLISD FYPGAVTVAW KADSSPVKAG VETTTPSKQS NNKYAASSYL
SLTPEQWKSH RSYSCQVTHE GSTVEKTVAP TECS (SEQ ID NO: 26)

DR5/TRAILR2 Targeting antibodies
Drozitumab
(Heavy chain, Fc region underlined)
EVQLVQSGGG VERPGGSLRL SCAASGFTFD DYANSWVRQA PGKGLEWVSG INWQGGSTGY
ADSVKGRVTI SRDNAKNSLY LQMNSLRAED TAVYYCAKIL GAGRGWYFDY WGKGTTVTVS
SASTKGPSVF PLAPSSKSTS GGTAALGCLV KDYFPEPVTV SWNSGALTSG VHTFPAVLQS
SGLYSLSSVV TVPSSSLGTQ TYICNVNHKP SNTKVDKKVE PKSCDKTHTC PPCPAPELLG
GPSVFLFPPK PKDTLMISRT PEVTCVVVDV SHEDPEVKFN WYVDGVEVHN AKTKPREEQY
NSTYRVVSVL TVLHQDWLNG KEYKCKVSNK ALPAPIEKTI SKAKGQPREP QVYTLPPSRE
EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K (SEQ ID NO: 27)

(Light chain)
SELTQDPAVS VALGQTVRIT CSGDSLRSYY ASWYQQKPGQ APVLVIYGAN NRPSGIPDRF
SGSSSGNTAS LTITGAQAED EADYYCNSAD SSGNHVVFGG GTKLTVLGQP KAAPSVTLFP
PSSEELQANK ATLVCLISDF YPGAVTVAWK ADSSPVKAGV ETTTPSKQSN NKYAASSYLS
LTPEQWKSHK SYSCQVTHEG STVEKTVAPT ECS (SEQ ID NO; 28)

scTRAIL-Fc
Heavy chain only needed, Fc region underlined
QPVAAHITGTRGRSNTLSSPNSKNEKALGPKINSWESSRSGHSFLSNLHLRNGELVIHEKGFYYIYSQTYFRFQE
EIKEMTKNDKQMVQYIYKYTSYPDPILLMKSARNSCWSKDAEYGLYSIYQGGIFELKENDRIFVSVTNEHLIDMD
HEASFFGAFLVGGSGSGNGSRVAAHITGTRGRSNTLSSPNSKNEKALGRKINSWESSRSGHSFLSNLHLRNGELV
IHEKGFYYIYSQTYFRFQEEIKENTKNDKQMVQYIYKYTSYPDPILLMKSARNSCWSKDAEYGLYSIYQGGIFEL
KENDRIFVSVTNEHLIDMDHEASFFGAFLVGGSGSGNGSRVAAHITGTRGRSNTLSSPNSKNEKALGRKINSWES
SRSGHSFLSNLHLRNGELVIHEKGFYYIYSQTYFRFQEEIKENTKNDKQMVQYIYKYTSYPDPILLMKSARNSCW
SKDAEYGLYSIYQGGIFELKENDRIFVSVTNEHLIDMDHEASFFGAFLVGGPGSSSSSSGSCDKTHTCPPCPAP
ELLGGPSVFLFPPKPKDTLMISRTPEVTCVVVDVSHEDPEVKFNWYVDGVEVHNAKTKPREEQYSSTYRVVSVLT
VLHQDWLNCKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK (SEQ ID
NO: 29)

KMTR2
H1scFv heavy chain (no light chain needed, Fc region underlined)
QVQLQQSGPGLVKPSQTLSLTCAISGDSVSSTTVAWDWIRQSPSRGLEWLGRTYYRSKWYNEYAVSVKSRITINV
DTSKNQISLQLNSVTPEDTAVYYCAREPDAGRGAFDIWGQGTTVTSPLRWGRFGWRGLGRGWLRSPVTQSPGTLS
LSPGERATLSCRASQSVSSSHLAWYQQKPGQAPRLLIYGASSRATGIPDRFSGSGSGTDFTLTISSLEPEDFAVY
YCQQRSNWPPRAVFGQGTRLEIKGGSGGSEPKSSDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 30)

H1 Heavy chain (pairs with L1, Fc region underlined)
QVQLQQSGPGLVKPSQTLSLTCAISGDSVSSTTVAWDWIRQSPSRGLEWLGRTYYRSKWYNEYAVSVKSRITINV
DTSKNQISLQLNSVTPEDTAVYYCAREPDAGRGAFDIWGQGTTVTSPASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKSS
DKTHTCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEALHNHYTQKSLSLSP
GK (SEQ ID NO: 31)

L1 Light chain (pairs with H1)
LRSPVTQSPGTLSLSPGERATLSCRASQSVSSSHLAWYQQKPGQAPRLLIYGASSRATGIPDRFSGSGSGTDFTL
TISSLEPEDFAVYYCQQRSNWPPRAVFGQGTRLEIKRTVAAPSVFIFPPSDEQLKSGTASVVCLLNNFYPREAKV
QWVDNALGSGNSQESVTEQDSKDSTYSLSSTLTLSKADYEKHKVYACEVTHQGLSSPVTKSFNRGEC (SEQ
ID NO: 32)

TABLE 5-continued

| Antibody sequences |
| --- |
| H6scFv heavy chain (no light chain needed, Fc region underlined)<br>QVQLQQSGPGRVQPSQTLSLTCAISGDSVSNNNAAWYWIRQSPSRGLEWLGRTYYRSKWYNDYAVSVKSRITISP<br>DTSKNQFSLQLNSVTPEDTAVYYCARRGDGNSYFDYWGQGTLVTVSSGILRWGRFGWRGLGRGWLEIVLTQSPGT<br>LSLSPGERATLSCRASQSVSSGYVSWYROKPGQAPRLLIYGASTRATGIPDRFSGSGSGTDFTLTISRLEPEDFA<br>VYYCHQYGSSPNTYGQGTKVGIKGGSGGSEPKSSDKTHTCPPCPAPELLGGPSVFLFPPKPKDTLMISRTPEVTC<br>VVVDVSHEDPEVKFNWYVDGVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKTTPPVLDSDGSFFLYSKLT<br>VDKSRWQQGNVFSCSVMHEALHNHYTQKSLSLSPGK (SEQ ID NO: 33) |
| H6 Heavy chain (pairs with L6, Fc region underlined)<br>QVQLQQSGPGRVQPSQTLSLTCAISGDSVSNNNAAWYWIRQSPSRGLEWLGRTYYRSKWYNDYAVSVKSRITISP<br>DTSKNQFSLQLNSVTPEDTAVYYCARRGDGNSYFDYWGQGTLVTVSSASTKGPSVFPLAPSSKSTSGGTAALGCL<br>VKDYPFEFVTVSWNSGALTSGVHTFPAVLQSSGLYSLSSVVTVPSSSLGTQTYICNVNHKPSNTKVDKKVEPKSS<br>DKTHTCPPCPAPELLGGPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPSRDELTKNQVSLTCLVK<br>GFYPSDIAVEWESNGQPENNYKTTPPVLDSDGSFFLYSKLTVDKSRWQQGNVFSCSVMHEALHNHYTQKSLSLSP<br>GK (SEQ ID NO: 34) |
| L6 Light chain (pairs with H6)<br>LEIVLTQSPGTLSLSPGERATLSCRASQSVSSGYVSWYRQKPGQAPRLLIYGASTRATGIPDRFSGSGSGTDFTL<br>TISRLEPEDFAVYYCHQYGSSPNTYGQGTKVGIKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRGEC (SEQ ID<br>NO: 35) |
| 1E62<br>Heavy chain, Fc region underlined<br>EVQLVQSGGGVERPGGSLRLSCAASGFTFDDYGMSSVRQAPGKGLEWVSGINWNGGSTGYADSVKGRVTISRDNA<br>KNSLYLQMNSLRAEDTAVYYCAKILGAGRGWYFDLWGKGTTVTVSSASTKGPSVFPLAPSSKSTSGGTAALGCLV<br>KDYFPEPVTVSWNSGALTSGVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALHNHYTQKSLSLSPG<br>K (SEQ ID NO: 36) |
| Light chain, Fc region underlined<br>SELTQDPAVSVALGQTVRITCQGDSLRSYYASWYQQKPGQAPVLVIYGKNNRPSGIPDRFSGSSSGNTASLTITG<br>AQAEDEADYYCNSRDSSGNHVVFGGGTKLTVLGQPKAAPSVTLFPPSSEELQANKATLVCLISDFYPGAVTVAWK<br>ADSSPVKAGVETTTPSKQSNNKYAASSLLSLTPEQWKSHKSYSCQVTHEGSTVEKTVAPTEC (SEQ ID<br>NO: 37) |
| Conatumumab/AMG 655<br>Conatumumab//AMG 655 heayy chain (Fc region underlined)<br>QVQLQESGPGLVKPSQTLSLTCTVSGGSISSGDYFWSWIRQLPGKGLEWICHIHNSGTTYYNPSLKSRVT<br>ISVDTSKKQFSLRLSSVTAADTAVYYCARDRGGDYYYGMDVWGQGTTVTVSSASTKGPSVFPLAPSSKSTSGGTA<br>ALGCLVDKYFPEPVTVSWNSGALTSGVHTFPAVLQSSGLYSLSSVVTVPSSSLGTQTYICNVNHK<br>PSNTKVDKRVEPKSCDKTHTCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTISKAKGQPREPQVYTLPPSR<br>EEMTKNQVSLTCLVKGFYPSDIAVEWESNGQPENNYKTTPPVLDSDGSFFLYSKLTVDLSRWQQGNVFSCSVMHE<br>ALHLMYTAKSLSLSPGE (SEQ ID NO: 38) |
| Conatumumab/AMG 655 light chain<br>EIVLTQSPGTLSLSPGERATLSCRASQGISRSYLAWYQQKPGQAPSLLIYGASSRATGIPDRFSGSGSGTDFTLT<br>ISRLEPEDFAVYYCQQFGSSPWTFGQGTEVEIKRTVAAPSVFIFPPSDEQLKSGTASVVCLLNNFYPREAKVQWK<br>VDNALQSGNSQESVTEQDSKDSTYLSSTLTLSKADEKHKVYACEVTHQGLSSPVTKSFNRGEC (SEQ ID<br>NO: 39) |
| TWEAKR Targeting antibodies<br>Enavatuzumab<br>(Heavy chain, Fc region underlined)<br>EVQLVESGGG LVQPGGSLRL SCAASGFTFS SYWMSWVRQA PGKGLEWVAE IRLKSDNYAT<br>HYAESVKGRF TISRDDSKNS LYLQMNSLRA EDTAVYYCTG YYADAMDYWG QGTLVTVSSA<br>STKGPSVFPL APSSKSTSGG TAALGCLVKD YFPEPVTVSW NSGALTSGVH TFPAVLQSSG<br>LYSLSSVVTV PSSSLGTQTY ICNVNHKPSN TKVDKKVEPK SCDKTHTCPP CPAPELLGGP<br>SVFLFPPKPK DTLMISRTPE VTCVVVDVSH EDPEVKFNWY VDGVEVHNAK TKPREEQYNS<br>TYRVVSVLTV LHQDWLNGKE YKCKVSNKAL PAPIEKTISK AKGQPREPQV YTLPPSREEM<br>TKNQVSLTCL VKGFYPSDIA VEWESNGQPE NNYKTTPPVL DSDGSFFLYS KLTVDKSRWQ<br>QGNVFSCSVM HEALHNHYTQ KSLSLSPGK (SEQ ID NO: 40) |
| (Light chain)<br>DTQMTQSPSS LSASVGDRVT ITCRASQSVS TSSYSYMHWY QQKPGKAPKL LIKYASNLES<br>GVPSRFSGSG SGTDFTLTIS SLQPEDFATY YCQHSWEIPY TFGGGTKVEI KRTVAAPSVE<br>IFPPSDEQLK SGTASVVCLL NNFYPREAKV QWKVDNALQS GNSQESVTEQ DSKDSTYSLS<br>STLTLSKADY EKHKVYACEV THQGLSSPVT KSFNRGEC (SEQ ID NO: 41) |

TABLE 5-continued

Antibody sequences

Dacetuzumab (WO2016069919)
hS2C6 heavy chain (SEQ ID NO: 42)

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

TABLE 5-continued

| Antibody sequences |
| --- |
| Phe Phe Leu Tyr Ser Lys Leu Thr Val Asp Lys Ser Arg Trp Gln Gln<br>405 410 415 |
| Gly Asn Val Phe Ser Cys Ser Val Met His Glu Ala Leu His Asn His<br>420 425 430 |
| Tyr Thr Gln Lys Ser Leu Ser Leu Ser Pro Gly Lys |
| hS2C6 light chain (SEQ ID NO: 43)<br>Asp Ile Gln Met Thr Gln Ser Pro Ser Ser Leu Ser Ala Ser Val Gly<br>1 5 10 15 |
| Asp Arg Val Thr Ile Thr Cys Arg Ser Ser Gln Ser Leu Val His Ser<br>20 25 30 |
| Asn Gly Asn Thr Phe Leu His Trp Tyr Gln Gln Lys Pro Gly Lys Ala<br>35 40 45 |
| Pro Lys Leu Leu Ile Tyr Thr Val Ser Asn Arg Phe Ser Gly Val Pro<br>50 55 60 |
| Ser Arg Phe Ser Gly Ser Gly Ser Gly Thr Asp Phe Thr Leu Thr Ile<br>65 70 75 80 |
| Ser Ser Leu Gln Pro Glu Asp Phe Ala Thr Tyr Phe Cys Ser Gln Thr<br>85 90 95 |
| Thr His Val Pro Trp Thr Phe Gly Gln Gly Thr Lys Val Glu Ile Lys<br>100 105 110 |
| Arg Thr Val Ala Ala Pro Ser Val Phe Ile Phe Pro Pro Ser Asp Glu<br>115 120 125 |
| Gln Leu Lys Ser Gly Thr Ala Ser Val Val Cys Leu Leu Asn Asn Phe<br>130 135 140 |
| Tyr Pro Arg Glu Ala Lys Val Gln Trp Lys Val Asp Asn Ala Leu Gln<br>145 150 155 160 |
| Ser Gly Asn Ser Gln Glu Ser Val Thr Glu Gln Asp Ser Lys Asp Ser<br>165 170 175 |
| Thr Tyr Ser Leu Ser Ser Thr Leu Thr Leu Ser Lys Ala Asp Tyr Glu<br>180 185 190 |
| Lys His Lys Val Tyr Ala Cys Glu Val Thr His Gln Gly Leu Ser Ser<br>195 200 205 |
| Pro Val Thr Lys Ser Phe Asn Arg Gly Glu Cys<br>210 215 |
| Lucatumumab: WO2012075111)<br>Light chain of HCD122 human anti-CD40 antibody (SEQ ID NO: 44)<br>Met Ala Leu Pro Ala Gln Leu Leu Gly Leu Leu Met Leu Trp Val Ser<br>1 5 10 15 |
| Gly Ser Ser Gly Asp Ile Val Met Thr Gln Ser Pro Leu Ser Leu Thr<br>20 25 30 |
| Val Thr Pro Gly Glu Pro Ala Ser Ile Ser Cys Arg Ser Ser Gln Ser<br>35 40 45 |
| Leu Leu Tyr Ser Asn Gly Tyr Asn Tyr Leu Asp Trp Tyr Leu Gln Lys<br>50 55 60 |
| Pro Gly Gln Ser Pro Gln Val Leu Ile Ser Leu Gly Ser Asn Arg Ala<br>65 70 75 80 |
| Ser Gly Val Pro Asp Arg Phe Ser Gly Ser Gly Ser Gly Thr Asp Phe<br>85 90 95 |
| Thr Leu Lys Ile Ser Arg Val Glu Ala Glu Asp Val Gly Val Tyr Tyr<br>100 105 110 |
| Cys Met Gln Ala Arg Gln Thr Pro Phe Thr Phe Gly Pro Gly Thr Lys<br>115 120 125 |

TABLE 5-continued

Antibody sequences

```
Val Asp Ile Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                  220

Gly Leu Ser Ser Pro Val Thr Lys Ser Phe Asn Arg Gly Glu Cys
225                 230                 235
```

Heavy chain of HCD122 human anti-CD40 antibody (SEQ ID NO: 45)

```
Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ala Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

TABLE 5-continued

Antibody sequences

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

Heavy chain of variant of HCD122 human anti-CD40 antibody (SEQ ID NO: 46)

```
Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

TABLE 5-continued

Antibody sequences

Thr Val Pro Ser Ser Ser Leu Gly Thr Gln Thr Tyr Ile Cys Asn Val
210 215 220

Asn His Lys Pro Ser Asn Thr Lys Val Asp Lys Arg Val Glu Pro Lys
225 230 235 240

Ser Cys Asp Lys Thr His Thr Cys Pro Pro Cys Pro Ala Pro Glu Leu
245 250 255

Leu Gly Gly Pro Ser Val Phe Leu Phe Pro Pro Lys Pro Lys Asp Thr
260 265 270

Leu Met Ile Ser Arg Thr Pro Glu Val Thr Cys Val Val Val Asp Val
275 280 285

Ser His Glu Asp Pro Glu Val Lys Phe Asn Trp Tyr Val Asp Gly Val
290 295 300

Glu Val His Asn Ala Lys Thr Lys Pro Arg Glu Glu Gln Tyr Asn Ser
305 310 315 320

Thr Tyr Arg Val Val Ser Val Leu Thr Val Leu His Gln Asp Trp Leu
325 330 335

Asn Gly Lys Glu Tyr Lys Cys Lys Val Ser Asn Lys Ala Leu Pro Ala
340 345 350

Pro Ile Glu Lys Thr Ile Ser Lys Ala Lys Gly Gln Pro Arg Glu Pro
355 360 365

Gln Val Tyr Thr Leu Pro Pro Ser Arg Glu Glu Met Thr Lys Asn Gln
370 375 380

Val Ser Leu Thr Cys Leu Val Lys Gly Phe Tyr Pro Ser Asp Ile Ala
385 390 395 400

Val Glu Trp Glu Ser Asn Gly Gln Pro Glu Asn Asn Tyr Lys Thr Thr
405 410 415

Pro Pro Val Leu Asp Ser Asp Gly Ser Phe Phe Leu Tyr Ser Lys Lys
420 425 430

Thr Val Asp Lys Ser Arg Trp Gln Gln Gly Asn Val Phe Ser Cys Ser
435 440 445

Val Met His Glu Ala Leu His Asn His Tyr Thr Gln Lys Ser Leu Ser
450 455 460

Leu Ser Pro Gly Lys
465

GITR Targeting antibodies

AMG228 heavy chain (Fc region underlined)
QVQLVESGGGVVQPGRSLRLSCVASGFTFSSYGMHWIRQAPGKGLEWVAVIWYEGSNKYYAESVKGRFTISRDNS
KNTLYLQMNSLRAEDTAVYYCARGGRLGLDYYSGMDVWGQGTTVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHNHYTQKSLSLS
PGK (SEQ ID NO: 48)

AMG2228 light chain
DIQMTQSPSSLSASVGDRVTITCRASQGIRNDLGWYQQKPGKAPKRLIYATSSLQSGVPSRFSGSGSGTEFTLTI
SSLQPEDFATYYCLQHNTYPWTFGQGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC (SEQ ID
NO: 49)

TRX518 heavy chain (Fc region underlined)
QVTLKESGPGILKPSQTLSLTCSFSGFSLSTSCMGVGWIRQPSGKGLEWLAHIWWDDDKYYNPSLKSQLTISKDT
SRNQVFLKITSVDTADAATYYCARTRRYFPFAYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSSDKT
HTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHNHYTQKSLSLSPGK
(SEQ ID NO: 50)

TABLE 5-continued

Antibody sequences

TRX518 light chains
DIVMTQSQKFMSTSVGDRVSVTCKASQNVGTNVAWYQQKPGQSPKALIYSASYRYSGVPDRFTGSGSGTDFTLTI
NNVHSEDLAEYFCQQYNTDPLTFGAGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC (SEQ ID
NO: 51)

MK-4166 heavy chain (Fc region underlined)
QVQLVESGGGVVQPGRSLRLSCAASGFTFSSYAMSWVRQAPGKGLEWVASISSGGTTYYPDSVKGRFTISRDNSK
NTLYLQMNSLRAEDTAVYYCARVGGYYDSMDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSSDKTH
TCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHYTQKSLSLSPGK
(SEC ID NO: 52)

MK-4166 light chain
EIVLTQSPGTLSLSPGERATLSCRASESVDNYGVSFMNWYQQKPGQAPRLLIYAASNQGSGIPDRFSGSGSGTDF
TLTISRLEPEDFAVYYCQQTKEVTWTFGQGTKVEIKRTVAAPSVFIFPPSDEQLKSGTASVVCLLNNFYPREAKV
QWKDNALQSGNSQESVTEQDSKDSTYSLSSTLTLSKADYEKHKVYACEVTHQGLSSPVTKSFNRGEC (SEQ
ID NO: 53)

BMS-986156 heavy chain (Fc region underlined)
QVTLKESGPGILKPSQTLSLTCSFSGFSLSTSGMGVGWIRQPSGKGLEWLAHIWWDDDKYYNPSLKSQLTISKDT
SRNQVFLKITSVDTADAATYYCARTRRYFPPAYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSSDKT
HTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHNHYTQKSLSLSPGK
(SEQ ID NO: 54)

BMS-986156 light chain
DIVMTQSQKFMSTSVGDRVSVTCKASQNVGTNVAWYQQKPGQSPKALIYSASYRYSGVPDRFTGSGSGTDFTLTI
NNVHSEDLAEYFCQQYNTDPLTFGAGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC (SEQ ID
NO: 55)

scGITRL-Fc (Heavy chain only needed, Fc region underlined)
ETAKEPCMAKFGPLPSKWQMASSEPPCVNKVSDWKLEILQNGLYLIYGQVAPNANYNDVAPFEVRLYKNKDMIQT
LTNKSKIQNVGGTYELHVGDTIDLIFNSEHQVLKNNTYWGIILLANPQFISGSGSGNGSETAKEPCMAKFGPLPS
KWQMASSEPPCVNKVSDWKLEILQNGLYLIYGQVAPNANYNDVAPFEVRLYKNKDMIQTLTNKSKIQNVGGTYEL
HVGDTIDLIFNSEHQVLKNNTYWGIILLANPQFISGSGSGNGSETAKEPCMAKFGPLPSKWQMASSEPPCVNKVS
DWKLEILQNGLYLIYGQVAPNANYNDVAPFEVRLYKNKDMIQTLTNKSKIQNVGGTYELHVGDTIDLIFNSEHQV
LKNNTYWGIILLANPQFISGSSSSSSSGSCDKTHTCPPCPAPELLGGPSVFLFPPKPKDTLMISRTPEVTCVVV
DVSHEDFEVKFNWYVDGVEVHNAKTKPREEQYSSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSGSLSPGK (SEQ ID NO: 56)

In one specific embodiment of any of the above embodiments, the plurality of homo-polymers comprises homo-tetramers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:7. In another specific embodiment of any of the above embodiments, the plurality of homo-polymers comprises homo-trimers of the polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence of SEQ ID NO:5.

In another embodiment, the disclosure provides compositions comprising a plurality of the particles of any embodiment herein comprising α-TNFRSF antibodies. The compositions may be used, for example, in the methods and uses of the disclosure. In one embodiment, all antibodies in the composition are identical. In another embodiment, the antibodies are, in total, not identical.

In another embodiment, the disclosure comprises pharmaceutical compositions comprising the α-TNFRSF antibody particles or compositions of any embodiment herein, and a pharmaceutically acceptable carrier. The pharmaceutical compositions may be used, for example, in the methods and uses of the disclosure.

In another embodiment, the disclosure provides uses of the α-TNFRSF antibody particles, compositions or pharmaceutical compositions for any suitable use, including but not limited to those described in the examples. In one embodiment, the disclosure provides methods for treating method for treating a tumor, comprising administering to a subject having a tumor an amount of the particles, compositions, or pharmaceutical composition or any embodiment or combination of embodiments herein effective to induce tumor cell apoptosis. In one embodiment, the tumor overexpresses DR5 relative to a control tumor or a threshold DR5 expression level. As shown in the examples that following, the particles of the disclosure targeting cell-surface TNFRSF receptors enhance signaling compared to free antibodies or Fc-fusions in DR5-mediated apoptosis, and were shown to induce tumor cell apoptosis. Thus, the compositions may be used to treat tumors.

In another embodiment, the disclosure provides kits for generating the α-TNFRSF antibody particles and compositions of the disclosure. In one embodiment, the kits comprise:

(a) one or more polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in embodiment herein; and (b) α-TNFRSF antibodies comprising an antibody selected from the group consisting of Lob 7/6, Lucatumumab, Dacetuzumab, Selicrelumab, Bleselumab, Urelumab, Utomilumab, Drozitumab, scTRAIL-Fc, KMTR2, 16E2, and Conatumumab (also referred to as AMG 655); optionally as further specified by the heavy and light chain amino acid sequences described above.

In this embodiment, when the two components are combined the particles spontaneously assemble via interaction of the antibodies or dimers with Fc binding interfaces.

In another embodiment, the kits comprise:

(a) host cells capable of expressing one or more polypeptide comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from the group consisting of SEQ ID NOS:1-9, wherein residues in parentheses are optional (i.e.: not considered in the percent identity requirement), wherein the polypeptide is capable of (a) assembling into a homo-polymer, and (b) binding to a constant region of an IgG antibody; optionally the polypeptides as further limited in any embodiment herein; and (b) host cells capable of expressing α-TNFRSF antibodies comprising an antibody selected from the group consisting of Lob 7/6, Lucatumumab, Dacetuzumab, Selicrelumab, Bleselumab, Urelumab, Utomilumab, Drozitumab, scTRAIL-Fc, KMTR2, 16E2, and Conatumumab (also referred to as AMG 655); optionally as further specified by the heavy and light chain amino acid sequences described above.

In this embodiment, the two components can be produced by the host cells and then combined so that the particles spontaneously assemble via interaction of the antibodies or dimers with Fc binding interfaces.

As described in the examples, the particles have substantial internal volume that can be used to package nucleic acid or protein cargo. Thus, in another embodiment that can be combined with any other embodiment, the particles comprise a cargo within the particle internal volume. Any suitable cargo may be packaged within the particles, including but not limited to nucleic acids or polypeptides useful for an intended purpose.

The polypeptides described herein may be chemically synthesized or recombinantly expressed. The particles, polypeptides polymers, monomers, antibodies, and/or dimers may be linked to other compounds to promote an increased half-life in vivo or promote increased stability or activity in blood or at an injection site. Such linkage can be covalent or non-covalent as is understood by those of skill in the art, and may be accomplished, by way of non-limiting example, by methods including but not limited to chemical crosslinking, PEGylation, HESylation, PASylation, and/or glycosylation.

In another embodiment, one or more monomer in the polypeptide polymer may be linked covalently to either the antibody or dimer, in order to increase half-life in vivo or promote increased stability or activity in blood or injection site.

The pharmaceutical compositions of the disclosure may comprise (a) the particles, or compositions of any embodiment or combination of embodiments herein, and (b) a pharmaceutically acceptable carrier. The pharmaceutical compositions may further comprise (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the composition additionally includes a stabilizer, e.g., a molecule which substantially prevents or reduces chemical and/or physical instability of the nanostructure, in lyophilized or liquid form. Exemplary stabilizers include sucrose, sorbitol, glycine, inositol, sodium chloride, methionine, arginine, and arginine hydrochloride.

The particles, or compositions may be the sole active agent in the composition, or the composition may further comprise one or more other agents suitable for an intended use.

As used herein, "treat" or "treating" means accomplishing one or more of the following: (a) reducing severity of symptoms of the disorder in the subject; (b) limiting increase in symptoms in the subject; (c) increasing survival; (d) decreasing the duration of symptoms; (e) limiting or preventing development of symptoms; and (f) decreasing the need for hospitalization and/or the length of hospitalization for treating the disorder.

As used herein, "limiting" means to limit development of the disorder in subjects at risk of such disorder.

As used herein, an "amount effective" refers to an amount of the particle, composition, or pharmaceutical composition that is effective for treating and/or limiting development of the disorder. The particle, composition, or pharmaceutical composition of any embodiment herein are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally.

Polypeptide compositions may also be administered via microspheres, liposomes, immune-stimulating complexes (ISCOMs), or other microparticulate delivery systems or sustained release formulations introduced into suitable tissues (such as blood). Dosage regimens can be adjusted to provide the optimum desired response (e.g., a therapeutic or prophylactic response). A suitable dosage range may, for instance, be 0.1 μg/kg-100 mg/kg body weight of the particle, composition, or pharmaceutical composition thereof. The composition can be delivered in a single bolus, or may be administered more than once (e.g., 2, 3, 4, 5, or more times) as determined by attending medical personnel.

Examples

We set out to design proteins that drive the assembly of arbitrary antibodies into symmetric assemblies with well-defined structures. We reasoned that symmetric protein assemblies could be built out of IgG antibodies, which are two-fold symmetric proteins, by placing the symmetry axes of the antibodies on the two-fold axes of the target architecture and designing a second protein to hold the antibodies in the correct orientation. As we aimed for a format that would work for many different antibodies, we chose as the nanoparticle interface the interaction between the constant fragment crystallizable (Fc) domain of IgG and the Fc-binding helical bundle protein A.

a General Computational Method for Antibody Cage Design

To design a homo-oligomer terminating with an Fc-binding interface that has the correct geometry to hold the IgGs in the correct relative orientation for the desired architecture, we computationally fused three protein building blocks together: Fc-binders, monomers, and homo-oligomers. The Fc-binder forms the first nanocage interface between the antibody and the nanocage-forming design, the homo-oligomer forms the second nanocage interface between designed protein chains, and the monomer links the two interfaces together in the correct orientation to generate the desired nanomaterial.

Figure 6:
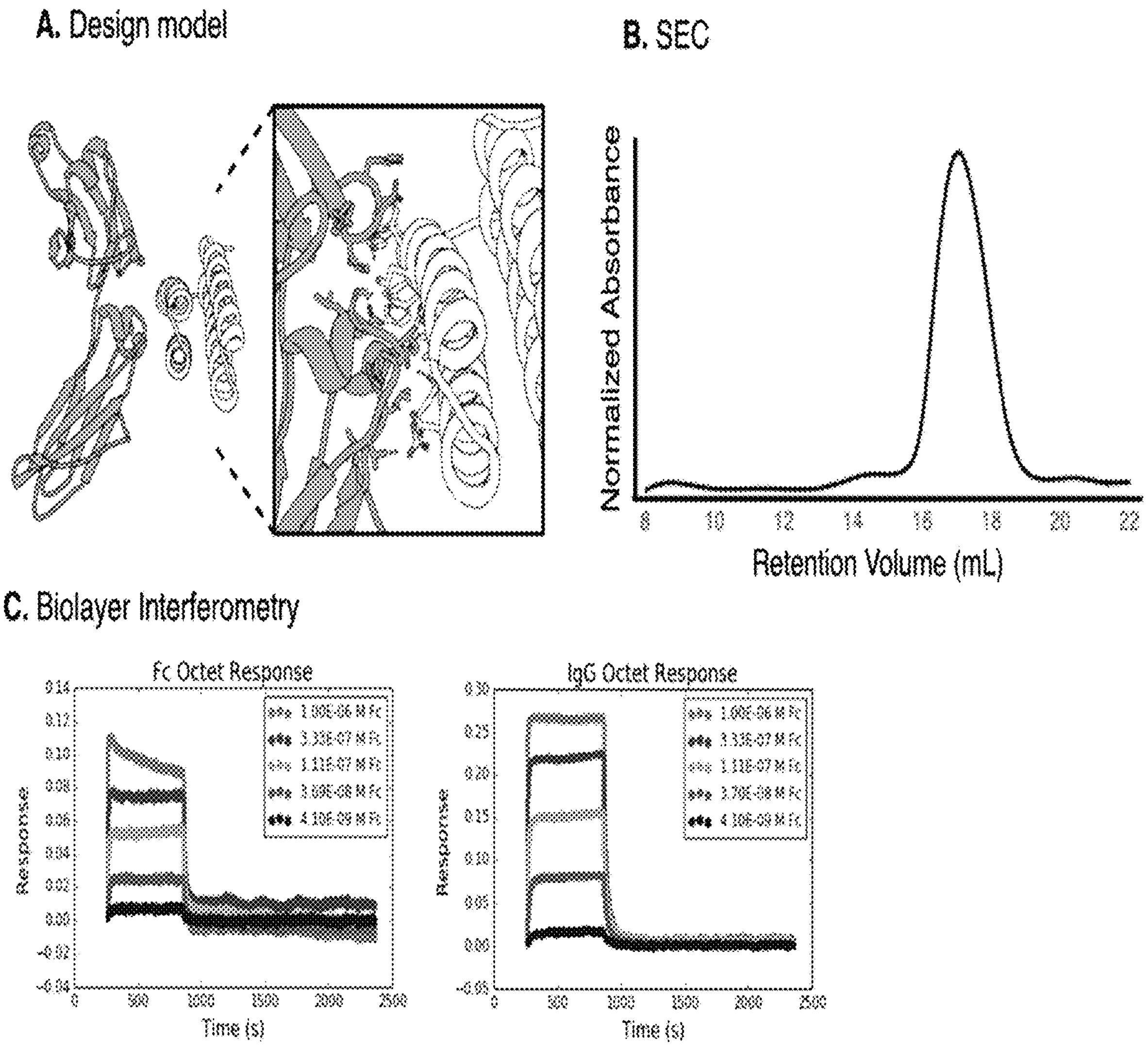
FIG. 6(A-C). Designed Fc-binding designed helical repeat. A, Model of the helical repeat protein DHR79 docked against antibody Fc (PDB ID: 1DEE). Residues from protein A (PDB ID: 1L6X) are grafted at the interface between the Fc and the helical repeat protein. B, SEC trace of the Fc-binding helical repeat monomer. C, Biolayer interferometry (BLI) of the Fc-binding helical repeat design with Fc (left) or with hIgG1 (right), with summary statistics (below).

To generate usable Fc-binding building blocks beyond protein A itself, we designed a second Fc-binding building block by grafting the protein A interface residues onto a designed helical repeat protein (FIG. 6). To create designs predicted to form antibody nanocages (hereafter AbCs, for Antibody Cage), we used a library consisting of these 2 Fc-binding proteins, 42 de novo designed helical repeat protein monomers, and between 1-3 homo-oligomers (2 C2s, 3 C3s, 1 C4, and 1 C5). An average of roughly 150 residues were available for fusion per protein building block, avoiding all positions involved in any protein-protein interface, leading to on the order of 107 possible tripartite (Fc-binder/monomer/homo-oligomer) fusions. For each of these tripartite fusions, the rigid body transform between the internal homo-oligomeric interface and the Fc-binding interface is determined by the shapes of each of its three building blocks and the locations and geometry of the "junctions" that link them into a single subunit.

We used a recently described computational protocol (WORMS) that rapidly samples all possible fusions from our building block library to identify those with the net rigid body transforms required to generate dihedral, tetrahedral, octahedral, and icosahedral AbCs (20, 21). To describe the final nanocage architectures, we follow a naming convention which summarizes the point group symmetry and the cyclic symmetries of the building blocks. For example, a T32 assembly has tetrahedral point group symmetry and is built out of a C3 cyclic symmetric antibody-binding designed oligomer, and the C2 cyclic symmetric antibody Fc. While the antibody dimer aligns along the two-fold axis in all architectures, the designed component is a second homodimer in D2 dihedral structures; a homotrimer in T32 tetrahedral structures, 032 octahedral structures, and 132 icosahedral structures; a homotetramer in 042 octahedral structures; and a homopentamer in 152 icosahedral structures.

To make the fusions, the protocol first aligns the model of the Fc and Fc-binder protein along the C2 axis of the specified architecture (FIG. 1*a-b*). The Fc-binder is then fused to a monomer, which is in turn fused to a homo-oligomer. Rigid helical fusions are made by superimposing residues in alpha helical secondary structure from each building block; in the resulting fused structure one building block chain ends and the other begins at the fusion point, forming a new, continuous alpha helix (FIG. 1*c*). For proper nanocage assembly to occur, fusions are made so that the antibody two-fold axis and the symmetry axis of the homo-oligomer intersect at precise angles at the center of the architecture (FIG. 1*d*). To generate D2 dihedral, T32 tetrahedral, O32 or O42 octahedral, and 132 or 152 icosahedral nanocages, the required respective intersection angles are 90.0°, 54.7°, 35.3°, 45.0°, 20.9°, and 31.7°. We allowed angular and distance deviations from the ideal architecture of at most 5.7° and 0.5 Å, respectively (see Methods). Candidate fusion models were further filtered based on the number of contacts around the fusion junction (to gauge structural rigidity) and clashes between backbone atoms. Next, the amino acid identities and conformations around the newly formed building block junction were optimized using the SymPackRotamersMover in Rosetta™ to maintain the rigid fusion geometry required for assembly (FIG. 1*e*). Following sequence design, we selected for experimental characterization six D2 dihedral, eleven T32 tetrahedral, four O32 octahedral, two O42 octahedral, fourteen I32 icosahedral, and eleven I52 icosahedral designs predicted to form AbCs (FIG. 1*f*).

Structural Characterization

Synthetic genes encoding designed protein sequences appended with a C-terminal 6× histidine tag were expressed in *E. coli*. Designs were purified from clarified lysates using immobilized metal affinity chromatography (IMAC), and size exclusion chromatography (SEC) was used as a final purification step. Across all geometries, 34 out of 48 AbC-forming designs had a peak on SEC that roughly corresponded to the expected size of the design model. Designs were then combined with human IgG1 Fc, and the assemblies were re-purified via SEC. Eight of these AbC-forming designs assembled with Fc into a species that eluted as a monodisperse peak at a volume consistent with the target nanoparticle molecular weight (FIG. 2*a-b;* 3 D2 dihedral, 2 T32 tetrahedral, 1 O42 octahedral, and 2 152 icosahedral AbCs). For the i52.6 design, adding 100 mM L-arginine to the assembly buffer prevented aggregation after combining with Fc; all other designs readily self-assembled in Tris-buffered saline. Most other designs still bound Fc, as evidenced by SEC, native gels, or by visibly precipitating with Fc after combination, but did not form monodisperse nanoparticles by SEC (Table 6), perhaps because of deviations from the target fusion geometry.

TABLE 6

Success rates of designed antibody-binding cage-forming oligomers.

| Geometry | # ordered | Soluble component | Good SEC component | Forms cage with Fc |
|---|---|---|---|---|
| D2 dihedron | 6 | 5 | 4 | 3 |
| T32 tetrahedron | 11 | 8 | 7 | 2 |
| O32 octahedron | 4 | 3 | 3 | 0 |
| O42 octahedron | 2 | 1 | 1 | 1 |
| I32 icosahedron | 14 | 14 | 10 | 0 |
| I52 icosahedron | 11 | 11 | 10 | 2 |
| Total | 48 | 42 | 35 | 8 |

Figure 2:
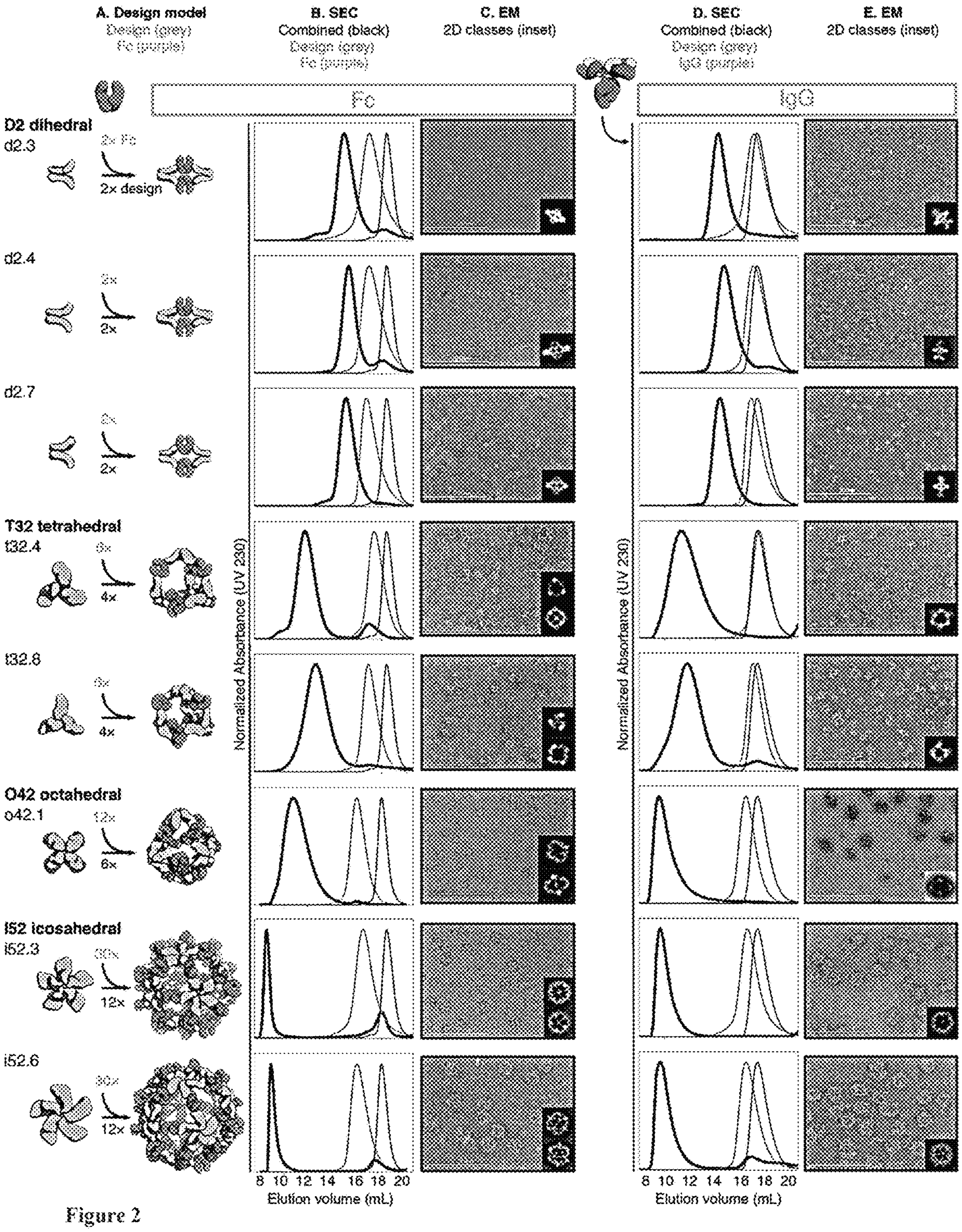
FIG. 2(A-F). Structural characterization of AbCs. A, Design models, with antibody Fc and designed AbC-forming oligomers. B, Overlay of SEC traces of assembly formed by mixing design and Fc with those of the single components. C, EM images with 2D averages in inset; all data is from negative-stain EM with the exception of designs o42.1 and i52.3 (cryo-EM). D-E, SEC (D) and NS-EM representative micrographs with 2D class averages (E) of the same designed antibody cages assembled with full human IgG1 (with the 2 Fab regions intact).

Solubility (column 2) refers to the presence of protein in the post-lysis, post-centrifugation, pre-IMAC soluble fraction as read out by SDS gel. Good SEC component (column 3) refers to SEC traces with some peak corresponding to the approximate predicted size of the nanocage-forming design model. Data for cage formation with Fc are shown in FIG. 2 and 3.

NS-EM micrographs and two-dimensional class averages revealed nanocages with shapes and sizes corresponding to the design models (FIG. 2*c*). AbCs also formed when assembled with intact antibodies (IgG with Fc and Fab domains), again generating monodisperse nanocages as shown by SEC and NS-EM (FIG. 2*d-e*). There is considerably more evidence of flexibility in the electron micrographs of the IgG-AbCs than the Fc-AbCs, as expected given the flexibility of the Fc-Fab hinge. In all cases, 2D class averages collected from the NS-EM data of AbCs made with intact IgG were still able to resolve density corresponding to the non-flexible portion of the assembly (FIG. 2*e*).

Figure 3:
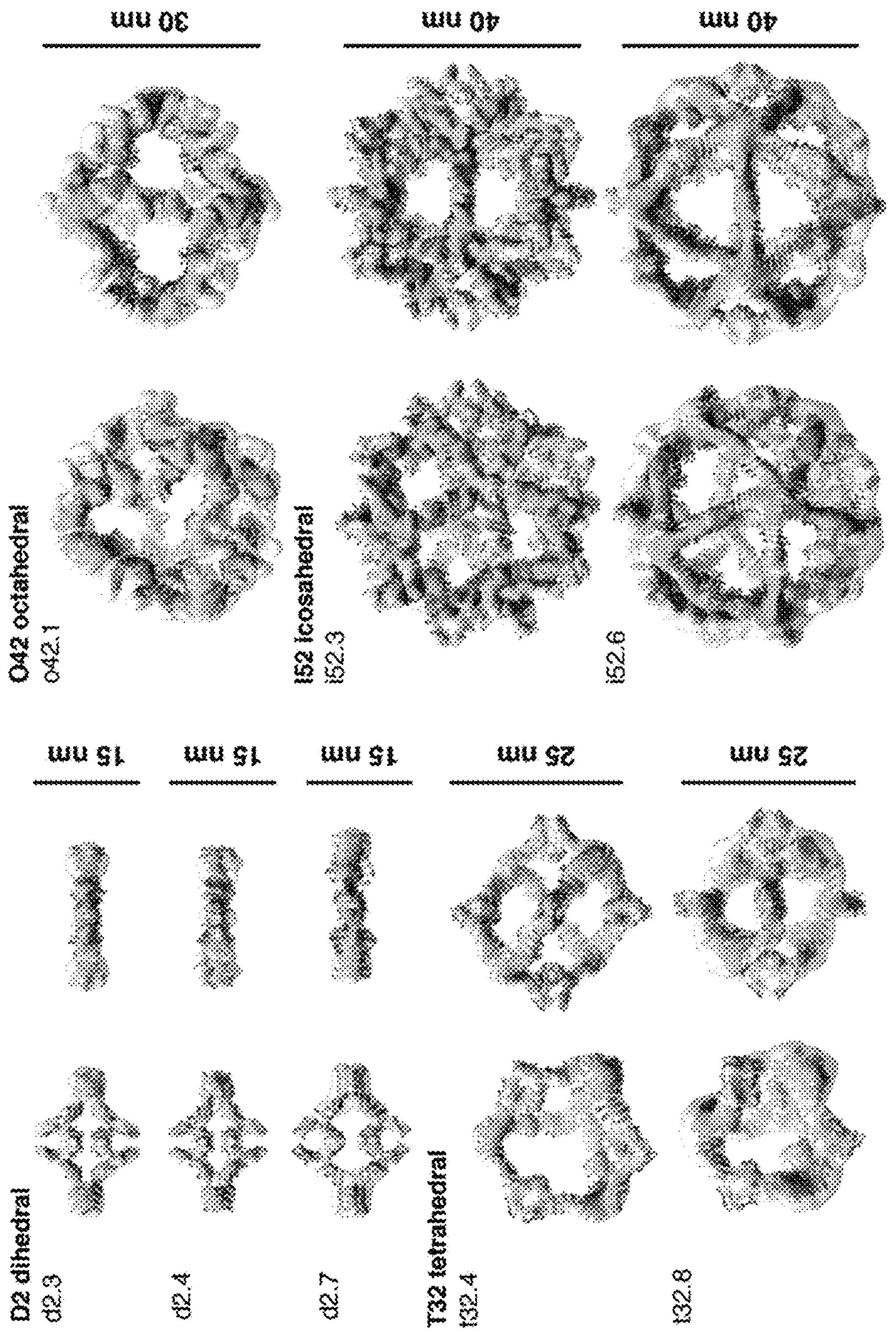
FIG. 3. 3D reconstructions of AbCs formed with Fc. Computational design models (cartoon representation) of each AbC are fit into the experimentally-determined 3D density from EM. Each nanocage is viewed along an unoccupied symmetry axis (left), and after rotation to look down one of the C2 axes of symmetry occupied by the Fc (right). 3D reconstructions from o42.1 and i52.3 are from cryo-EM analysis; all others, from NS-EM.

Single-particle NS-EM and cryo-EM reconstructed 3D maps of the AbCs formed with Fc are in close agreement with the computational design models (FIG. 3). Negative-stain EM reconstructions for the dihedral (d2.3, d2.4, d2.7), tetrahedral (t32.4, t32.8), and one of the icosahedral (i52.6) nanocages clearly show dimeric "U"-shaped Fcs and longer designed protein regions that fit together as computationally predicted. A single-particle cryo-EM reconstruction for the o42.1 design has clear density for the six designed tetramers sitting at the C4 vertices, which twist along the edges of the octahedral architecture to bind twelve dimeric Fcs, leaving the eight C3 faces unoccupied. Cryo-EM density for i52.3 with Fc likewise recapitulates the 20-faced shape of a regular icosahedron, with 12 designed pentamers protruding outwards at the C5 vertices (due to the longer length of the C5 building block compared to the monomer or Fc-binder), binding to 30 dimeric Fcs at the center of the edge, with 20 unoccupied C3 faces. In all cases, the computationally designed models fit clearly into the EM densities Enhancing Cell Signaling with AbCs The designed AbCs provide a general platform for investigating the effect of associating cell surface receptors into clusters on signaling pathway activation. Binding of antibodies to cell surface receptors can result in antagonism of signaling as engagement of the natural ligand is blocked (25). While in some cases receptor clustering has been shown to result in activation (11, 26, 27), there have been no systematic approaches to varying the valency and geometry of receptor engagement that can be readily applied to many different signaling pathways. We took advantage of the fact that almost any receptor-binding antibody, of which there are many, can be readily assembled into a wide array of different architectures using our AbC-forming designs to investigate the effect of receptor clustering on signaling. We assembled antibodies and Fc-fusions targeting a variety of signaling pathways into nanoparticles and investigated their effects as described in the following paragraphs.

Designed Tie2 Agonists for the Treatment of Sepsis and ARDS

This work focuses on the use of antibody fragment crystallizable (Fc)-fusions to angiopoietin-1 F-domain to enhance angiogenesis signaling.

Tie-2 Pathway Activation by Fc-Angiopoietin 1 Nanocages

Figure 4:
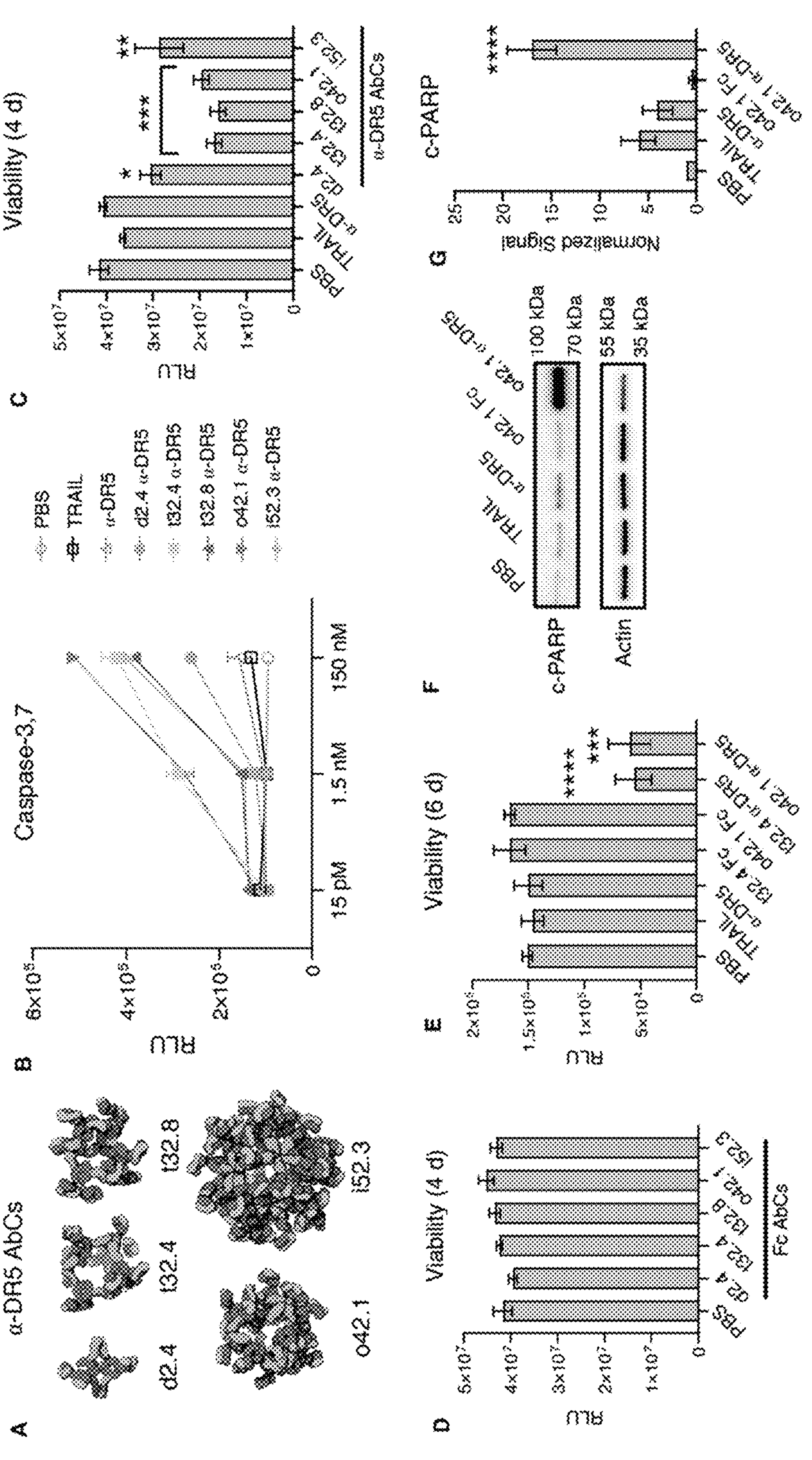
FIG. 4(A-K). AbCs activate apoptosis and angiogenesis signaling pathways. (A and B) Caspase-3/7 is activated by AbCs formed with α-DR5 antibody (A), but not the free antibody, in RCC4 renal cancer cells (B). (C and D) α-DR5 AbCs (C), but not Fc AbC controls (D), reduce cell viability 4 days after treatment. (E) -DR5 AbCs reduce viability 6 days after treatment. (F and G) o42.1 α-DR5 AbCs enhance PARP cleavage, a marker of apoptotic signaling; (G) is a quantification of (F) relative to PBS control. (H) The F-domain from angiopoietin-1 was fused to Fc (A1F-Fc) and assembled into octahedral (o42.1) and icosahedral (i52.3) AbCs. (I) Representative Western blots show that A1F-Fc AbCs, but not controls, increase pAKT and pERK1/2 signals. (J) Quantification of (I): pAKT quantification is normalized to o42.1 A1F-Fc signaling (no pAKT signal in the PBS control); pERK1/2 is normalized to PBS. (K) A1F-Fc AbCs increase vascular stability after 72 hours. (Left) Quantification of vascular stability compared with PBS. (Right) Representative images; scale bars, 100 mm. All error bars represent means±SEM; means were compared using analysis of variance and Dunnett post-hoc tests (tables 11 and 12). *P<0.05; P<0.01; *P<0.001; ****P<0.0001.
Figure 4:
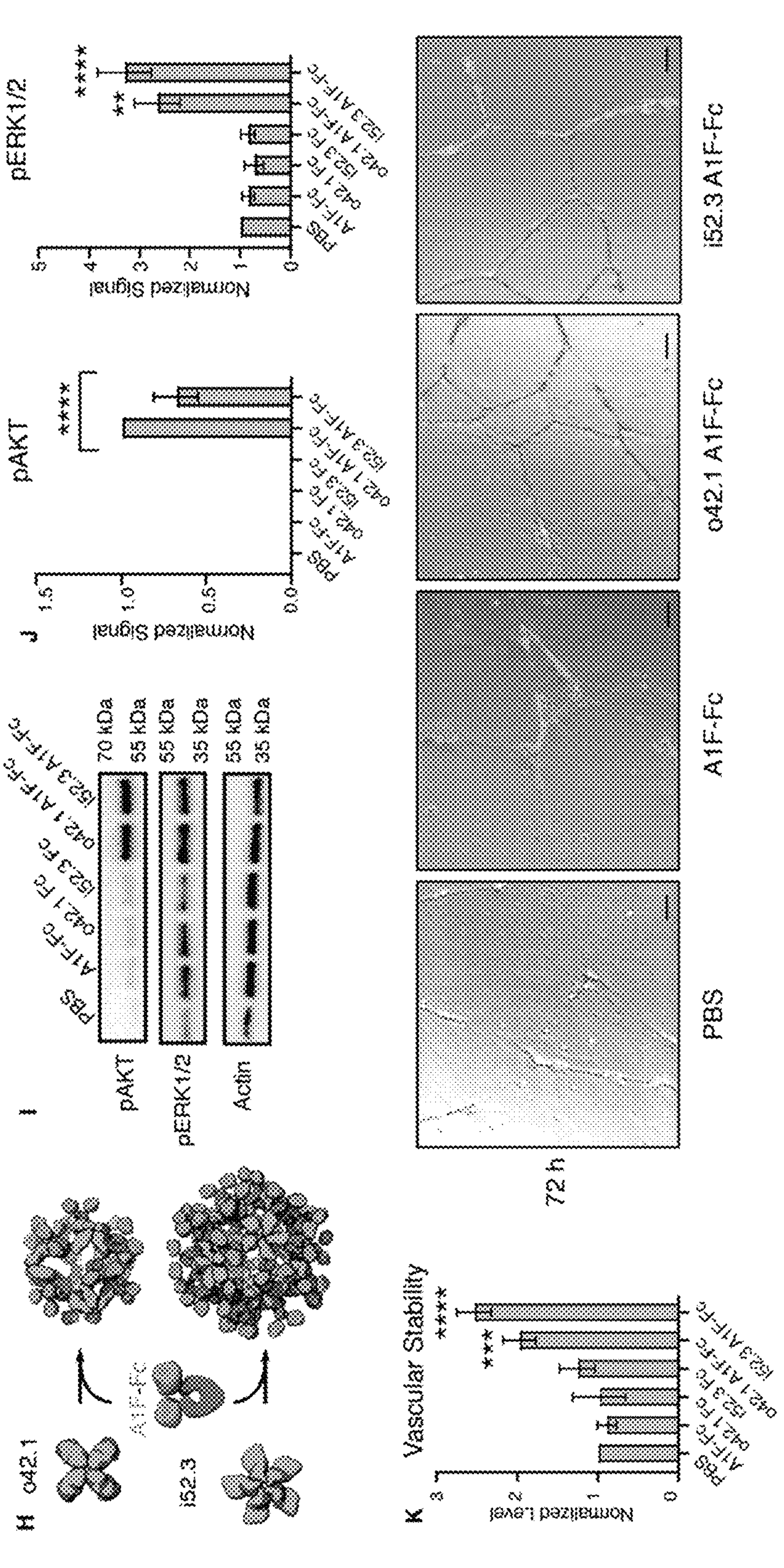

Certain receptor tyrosine kinases (RTKs), such as the Angiopoietin-1 receptor (Tie2), activate downstream signaling cascades when clustered (31, 32). Scaffolding the F-domain from angiopoietin-1 (A1F) onto nanoparticles induces phosphorylation of AKT and ERK, enhances cell migration and tube formation in vitro, and improves wound healing after injury in vivo (32). Therapeutics with these activities could be useful in treating conditions characterized by cell death and inflammation, such as sepsis and acute respiratory distress syndrome (ARDS). To determine whether the AbC platform could be used to generate such agonists, we assembled o42.1 and i52.3 AbCs with Fc fusions to A1F (FIG. 4*g*, FIG. 4*a-b*). The octahedral and icosahedral A1F-AbCs, but not Fc-only controls or free Fc-Ang1F, significantly increased AKT and ERK1/2 phosphorylation above baseline (FIG. 4*h-i*) and enhanced cell migration and vascular stability (FIG. 4*j-k*, FIG. 8*c-d*). These results show that the AbCs are more potent inducers of angiogenesis than free A1F-Fc, and as the components can be readily produced in large quantities, they are promising therapeutic candidates.

TNFR Superfamily Agonism by Antibody Cages

The designed AbCs provide a general platform for investigating the effect of associating cell surface receptors into clusters on signaling pathway activation. Binding of antibodies to cell surface receptors can result in antagonism of signaling as engagement of the natural ligand is blocked (6). There have been no systematic approaches to varying the valency and geometry of receptor engagement that can be readily applied to many different signaling pathways. We took advantage of the fact that almost any receptor-binding antibody, of which there are many, can be readily assembled into a wide array of different architectures using our AbC-forming designs to investigate the effect of receptor clustering on signaling. This work focuses on the use of antibodies targeting two tumor necrosis family receptor superfamily members: Death Receptor 5 (DR5) and CD40.

Induction of Tumor Cell Apoptosis by α-DR5 Nanocages

Death Receptor 5 (DR5) is a tumor necrosis factor receptor (TNFR) superfamily cell surface protein that initiates a caspase-mediated apoptotic signaling cascade terminating in cell death when cross-linked by its trimeric native ligand, TNF-related apoptosis-inducing ligand (TRAIL) (9, 10, 27-30). Like other members of the family, DR5 can also form alternative signaling complexes that activate non-apoptotic signaling pathways such as the NF-κB pro-inflammatory pathway and pathways promoting proliferation and migration upon ligand binding (29). Because DR5 is overexpressed in some tumors, multiple therapeutic candidates have been developed to activate DR5, such as α-DR5 mAbs and recombinant TRAIL, but these have failed clinical trials due to low efficacy and the development of TRAIL resistance in tumor cell populations (29, 30). Combining trimeric TRAIL with bivalent α-DR5 IgG leads to a much stronger apoptotic response than either component by itself, likely due to induction of larger-scale DR5 clustering via the formation of two-dimensional arrays on the cell surface (27).

We investigated whether α-DR5 AbCs formed with the same IgG (conatumumab) could have a similar anti-tumor effect without the formation of unbounded arrays. Five designs across four geometries were chosen (d2.4, t32.4, t32.8, o42.1, and i52.3) to represent the range of valencies and shapes (FIG. 4*a*). All α-DR5 AbCs were found to form single peaks on SEC and yielded corresponding NS-EM micrographs that were consistent with the formation of assembled particles (FIG. 2*d*-*e*).

Figure 7:
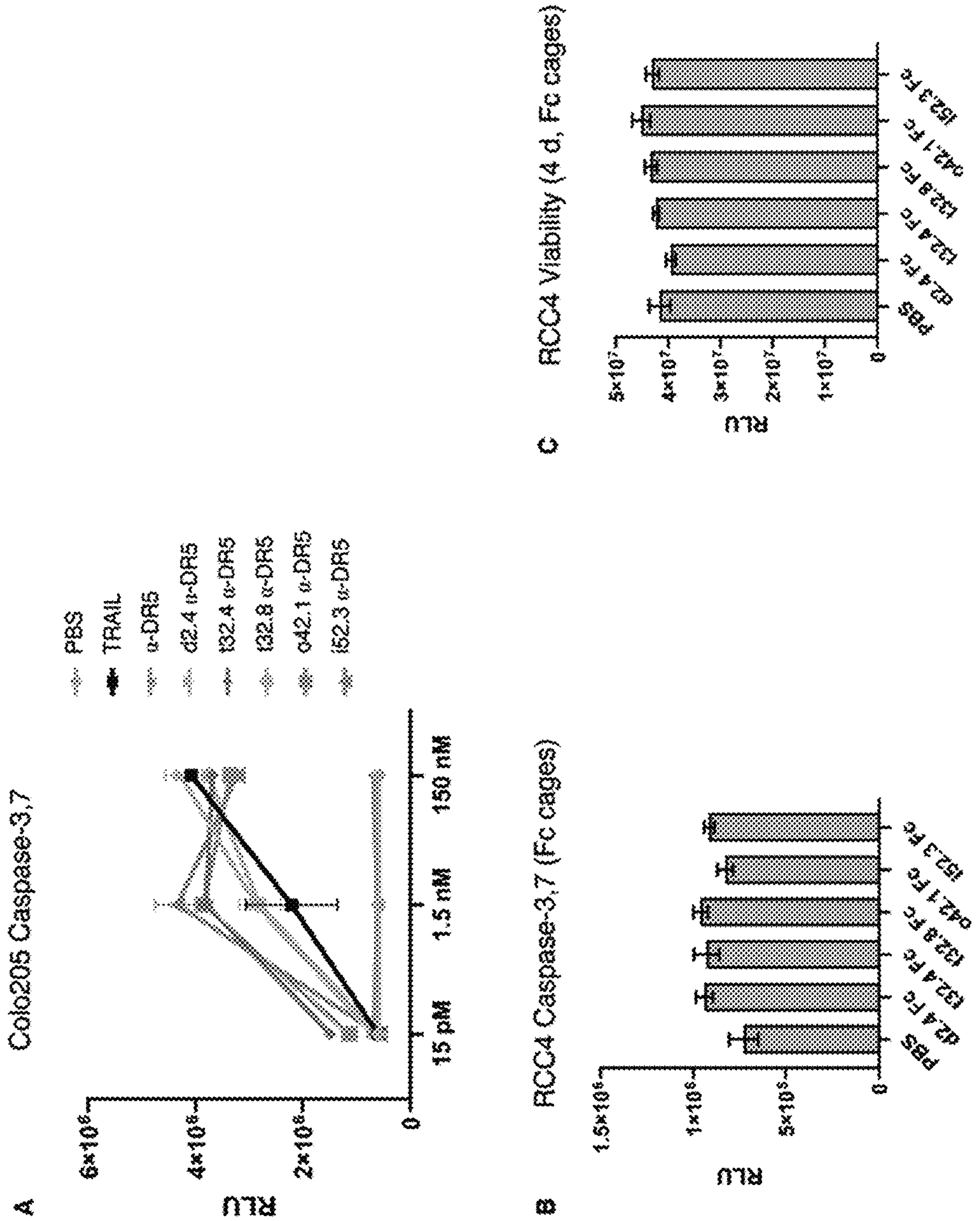
FIG. 7(A-F). Additional α-DR5 AbC experiments. A, α-DR5 AbCs and TRAIL activate caspase-3,7 in Colo205 colorectal cancer cell lines. B-C, AbCs formed with Fc from hIgG1 do not activate caspase-3,7 (B) or reduce viability (C) in RCC4 cells. D, α-DR5 AbCs do not greatly activate caspase-3,7 after 2 d (D) or reduce viability (E) in a primary tubular kidney cell line (RAM009). F, Cleaved PARP is activated by α-DR5 in RCC4 cells, but not by TRAIL, α-DR5, or Fc AbCs.
Figure 7:
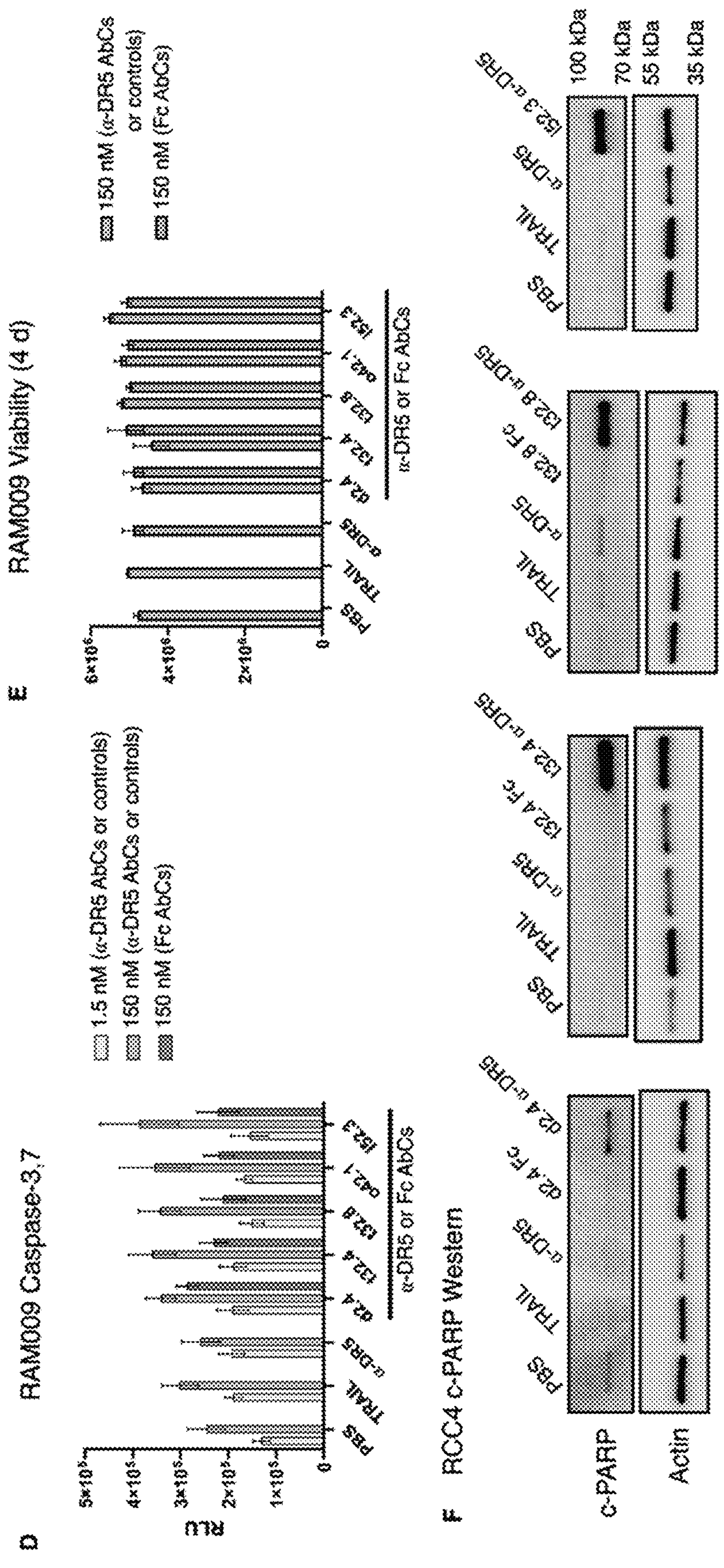
Figure 8:
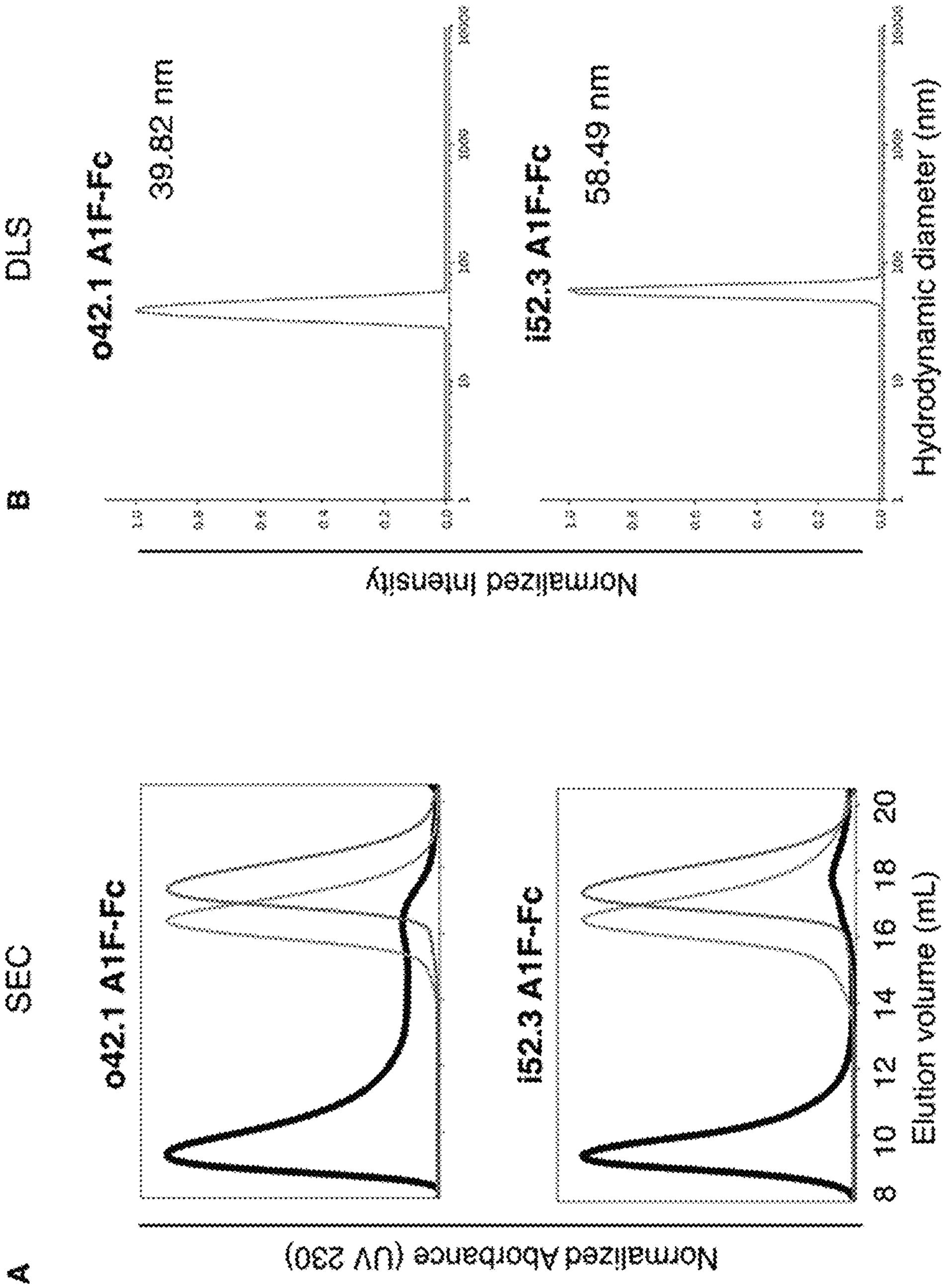
FIG. 8(A-E). Additional A1F-Fc AbC experiments. A-B, o42.1 and i52.3 AbCs formed with A1F-Fc are monodisperse and of the expected size per SEC on a Superose 6 column (A) and DLS (B). SEC shows the assembly trace in black, the relevant AbC design component in light grey, and the A1F-Fc in dark grey. C, A control assembly displaying 8 A1F ligands ("H8-A1F") produced similar levels of pAKT and pERK1/2 activation to A1F-Fc AbCs along with a comparable increase in vascular stability; data for all other conditions besides H8-A1F are replotted for convenience from FIG. 4*i-k*. D, Representative images of o42.1, i52.3 AbCs, and H8-A1F formed with Fc in the vascular stability assays; scale bars are 100 μm. E, o42.1 A1F-Fc AbCs were incubated with 100% human serum (HS) for 24 hours at 4 °C or 37 °C and applied to HUVEC cells at 150 nM. pAKT signal showed no decrease from o42.1 A1F-Fc particles incubated with serum. Statistical analyses are reported in Table 12.
Figure 8:
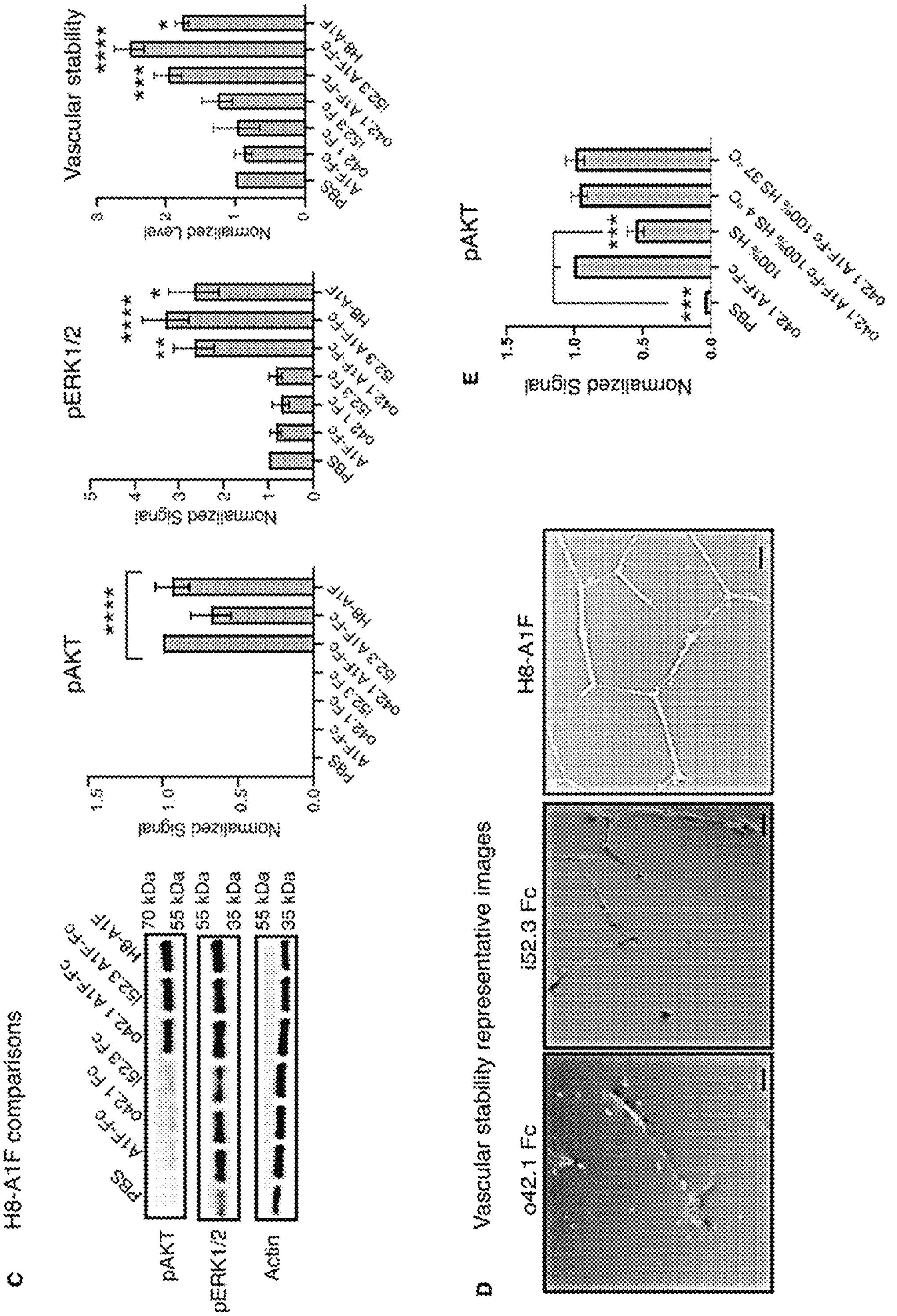

All five α-DR5 AbCs caused caspase 3/7-mediated apoptosis at similar levels to TRAIL in a colorectal tumor cell line, whereas the antibody alone or AbCs formed with bare Fc did not lead to caspase-3/7 activity or cell death, even at the highest concentrations tested (FIG. 4*a*, 7*a*-*b*). On the TRAIL-resistant renal cell carcinoma line RCC4, we found that all α-DR5 AbCs induced caspase-3,7 activity (FIG. 4*b*) and designs t32.4, t32.8, and o42.1 greatly reduced cell viability at 150 nM concentration (FIG. 4*c*). Designs t32.4 and o42.1 activated caspase at 100-fold lower concentrations (1.5 nM), and prolonged treatment of RCC4 with α-DR5 AbCs t32.4 and o42.1 at 150 nM resulted in the killing of nearly all cells after six days, suggesting that RCC4 cells do not acquire resistance to the nanocages (FIG. 4*e*). Free α-DR5 antibody, TRAIL, (FIG. 4*b*-*c*) or Fc-only AbCs (FIG. 4*d*, 7*c*) did not activate caspase or lead to cell death in RCC4 tumor cell lines.

We next investigated the downstream pathways activated by the α-DR5 AbCs by analyzing their effects on cleaved PARP, a measure of apoptotic activity, as well as the NF-kB target cFLIP. Consistent with the caspase and cell viability data, o42.1 α-DR5 AbCs increased cleaved PARP, while free α-DR5 antibody, TRAIL or o42.1 Fc AbCs did not result in an increase in cleaved PARP over baseline (FIG. 4*f*-*g*). All other α-DR5 AbCs were also found to increase cleaved PARP (FIG. 7*f*). These results suggest that α-DR5 AbCs may overcome TRAIL resistance by inhibiting anti-apoptotic pathways, which enhances the apoptotic cascade induced by DR5 super-clustering. Finally, the α-DR5 AbCs did not induce apoptosis in healthy primary kidney tubular cells (FIG. 7*d*-*e*).

α-CD40 Nanocages Activate CD40-Expressing CHO Cells

CD40, a TNFR superfamily member expressed on antigen presenting dendritic cells and B cells, is cross-linked by trimeric CD40 ligand (CD40L or CD154) on T cells, leading to signaling and cell proliferation (33, 34). We investigated whether assembling a non-agonist α-CD40 antibody (LOB7/6) into nanocages could substitute for the need for cell surface presentation. Octahedral AbCs were assembled with LOB7/6 IgG; SEC, dynamic light scattering (DLS), and NS-EM (FIG. 5*a*-*d*) characterization showed these to be monodisperse with the expected octahedral shape. The octahedral α-CD40 LOB7/6 AbCs were found to induce robust CD40 activation in CD40-expressing reporter CHO cells (J215A, Promega), at concentrations hundredfold less than a control activating α-CD40 antibody (Promega), while no activation was observed for the free LOB7/6 antibody or octahedral AbC formed with non-CD40 binding IgG (FIG. 5*e*, Table 7). This demonstrates that nanocage assembly converts the non-agonist α-CD40 mAb into a CD40 pathway agonist.

TABLE 7

EC50s from CD40 activation experiments.

| | EC50 log(μM) | 95% CI log(μM) |
|---|---|---|
| o42.1 IgG control | −1.422 | Not found |
| α-CD40 | 1.466 | 1.247 to 1.833 |
| LOB7/6 | −1.471 | Not found |
| o42.1 LOB7/6 | 0.1134 | −0.001058 to 0.2037 |

EC50 values were interpolated from the response curves determined using the log(agonist) vs. response - Variable slope (four parameters) fit using Graphpad Prism ™ Software

TABLE 8

List of antibodies formed into cages as verified by at minimum size exclusion chromatography.

| Ab reactivity | Ab subclass | Designs (validated by SEC at minimum) | Comments |
|---|---|---|---|
| α-CD4 | mIgG2b | o42.1 | OKT4 |
| α-CD40 | mIgG2a or mIgG2b | o42.1 | LOB7/6 or 82111 (respectively) |
| α-DRS (human) | hIgG1 | d2.3, d2.4, d2.7, t32.4, t32.8, o42.1, i52.3, i52.6 | conatumumab |
| α-DR5 (mouse) | Armenian hamster IgG | t32.4, o42.1 | MD5-1 |
| α-EGPR | hIgG1 | mIgG2b | cetuximab |
| α-LRP6 | hIgG1 | t32.4, o42.1 | YW210.09 |
| α-RSV F | hIgG1 | d2.3, d2.4, d2.7, t32.4, t32.8, o42.1, i52.3, i52.6 | mpe8 |
| Non-specific | Rabbit IgG | d2.4, o42.1 | Rabbit serum IgG |

Successfully formed cages (by SEC) listed by the antibody target reactivity, antibody species and isotype, and designs used.

TABLE 9

List of Fc-fusions formed into cages as verified by at minimum size exclusion chromatography.

| Fc-fusion ligand | Fc subclass | Designs (validated by SEC at minimum) | Comments |
|---|---|---|---|
| Angiopoietin-1 F-domain | hIgG1 | d2.4, t32.4, t32.8, o42.1, i52.3 | |
| Angiotensin-converting enzyme 2 (ACE2) | hIgG1 | o42.1 | |
| CD80 | hIgG1 | o42.1 | |
| mRuby2 | hIgG1 | d2.4, t32.4, t32.8, o42.1, i52.3 | |
| sfGFP | hIgG1 | d2.4, t32.4, t32.8, o42.1, i52.3 | |
| VEGF-a | hIgG1 | t32.4, o42.1 | |
| VEGF-c | hIgG1 | t32 4, o42.1 | |

Successfully formed cages (by SEC) listed by the ligand that was fused to Fc, the Fc sequence species and isotype, and designs used Discussion Our approach goes beyond previous computational design efforts to create functional nanomaterials by integrating form and function; our AbCs employ antibodies as both structural and functional components. By fashioning designed antibody-binding, cage-forming oligomers through rigid helical fusion, a wide range of geometries and orientations can be achieved. This design strategy can be generalized to incorporate other homo-oligomers of interest into cage-like architectures. For example, nanocages could be assembled with viral glycoprotein antigens using components terminating in helical antigen-binding proteins, or from symmetric enzymes with exposed helices available for fusion to maximize proximity of active sites working on successive reactions. The AbCs offer considerable advantages in modularity compared to previous fusion of functional domain approaches; any of the thousands of known antibodies with sufficient protein A binding can be simply mixed with the appropriate design to drive formation of the desired symmetric assembly, and we have demonstrated this principle using multiple different IgGs and Fc-fusions (Tables 8-9). EM and SEC demonstrate monodispersity comparable to IgM and not (to our knowledge) attained by any other antibody-protein nanoparticle formulations.

AbCs show considerable promise as signaling pathway agonists. Assembly of antibodies against RTK- and TNFR-family cell-surface receptors into AbCs led to activation of diverse downstream signaling pathways involved in cell death, proliferation, and differentiation. While antibody-mediated clustering has been previously found to activate signaling pathways (11, 27, 33), our approach has the advantage of much higher structural homogeneity, allowing more precise tuning of phenotypic effects and more controlled formulation. AbCs also enhanced antibody-mediated viral neutralization. There are exciting applications to targeted delivery, as the icosahedral AbCs have substantial internal volume (around 15,000 nm3, based on an estimated interior radius of 15.5 nm) that could be used to package nucleic acid or protein cargo, and achieving different target specificity in principle is as simple as swapping one antibody for another. We anticipate that the AbCs developed here, coupled with the very large repertoire of existing antibodies, will be broadly useful across a wide range of applications in biomedicine.

REFERENCES AND NOTES

1. R.-M. Lu, Y.-C. Hwang, I.-J. Liu, C.-C. Lee, H.-Z. Tsai, H.-J. Li, H.-C. Wu, Development of therapeutic antibodies for the treatment of diseases. J. Biomed. Sci. 27, 1 (2020).
2. H. J. Kang, Y. J. Kang, Y.-M. Lee, H.-H. Shin, S. J. Chung, S. Kang, Developing an antibody-binding protein cage as a molecular recognition drug modular nanoplatform. Biomaterials. 33, 5423-5430 (2012).
3. H. Kim, Y. J. Kang, J. Min, H. Choi, S. Kang, Development of an antibody-binding modular nanoplatform for antibody-guided targeted cell imaging and delivery. RSC Advances. 6 (2016), pp. 19208-19213.
4. A. M. Cuesta, N. Sainz-Pastor, J. Bonet, B. Oliva, L. Alvarez-Vallina, Multivalent antibodies: when design surpasses evolution. Trends Biotechnol. 28, 355-362 (2010).
5. N. Nuñez-Prado, M. Compte, S. Harwood, A. Álvarez-Méndez, S. Lykkemark, L. Sanz, L. Álvarez-Vallina, The coming of age of engineered multivalent antibodies. Drug Discovery Today. 20 (2015), pp. 588-594.
6. A. Miller, S. Carr, T. Rabbitts, H. Ali, Multimeric antibodies with increased valency surpassing functional affinity and potency thresholds using novel formats. MAbs. 12, 1752529 (2020).
7. M. Klement, J. Zheng, C. Liu, H.-L. Tan, V. V. T. Wong, A. B.-H. Choo, D.-Y. Lee, D. S.-W. Ow, Antibody engineering of a cytotoxic monoclonal antibody 84 against human embryonic stem cells: Investigating the effects of multivalency on cytotoxicity. Journal of Biotechnology. 243 (2017), pp. 29-37.
8. N. S. Laursen, R. H. E. Friesen, X. Zhu, M. Jongeneelen, S. Blokland, J. Vermond, A. van Eijgen, C. Tang, H. van Diepen, G. Obmolova, M. van der Neut Kolfschoten, D. Zuijdgeest, R. Straetemans, R. M. B. Hoffman, T. Nieusma, J. Pallesen, H. L. Turner, S. M. Bernard, A. B. Ward, J. Luo, L. L. M. Poon, A. P. Tretiakova, J. M. Wilson, M. P. Limberis, R. Vogels, B. Brandenburg, J. A. Kolkman, I. A. Wilson, Universal protection against influenza infection by a multidomain antibody to influenza hemagglutinin. Science. 362, 598-602 (2018).
9. O. Seifert, A. Plappert, S. Fellermeier, M. Siegemund, K. Pfizenmaier, R. E. Kontermann, Tetravalent Antibody-scTRAIL Fusion Proteins with Improved Properties. Molecular Cancer Therapeutics. 13 (2014), pp. 101-111.
10. M. Siegemund, F. Schneider, M. Hutt, O. Seifert, I. Müller, D. Kulms, K. Pfizenmaier, R. E. Kontermann, IgG-single-chain TRAIL fusion proteins for tumour therapy. Sci. Rep. 8, 7808 (2018).
11. R. S. Riley, E. S. Day, Frizzled7 Antibody-Functionalized Nanoshells Enable Multivalent Binding for Wnt Signaling Inhibition in Triple Negative Breast Cancer Cells. Small. 13 (2017), doi:10.1002/smll.201700544.
12. E. Hiramoto, A. Tsutsumi, R. Suzuki, S. Matsuoka, S. Arai, M. Kikkawa, T. Miyazaki, The IgM pentamer is an asymmetric pentagon with an open groove that binds the AIM protein. Sci Adv. 4, eaau1199 (2018).

13. N. P. King, W. Sheffler, M. R. Sawaya, B. S. Vollmar, J. P. Sumida, I. André, T. Gonen, T. O. Yeates, D. Baker, Computational design of self-assembling protein nanomaterials with atomic level accuracy. Science. 336, 1171-1174 (2012).
14. J. B. Bale, S. Gonen, Y. Liu, W. Sheffler, D. Ellis, C. Thomas, D. Cascio, T. O. Yeates, T. Gonen, N. P. King, D. Baker, Accurate design of megadalton-scale two-component icosahedral protein complexes. Science. 353, 389-394 (2016).
15. G. Ueda, A. Antanasijevic, J. A. Fallas, W. Sheffler, J. Copps, D. Ellis, G. Hutchinson, A. Moyer, A. Yasmeen, Y. Tsybovsky, Y.-J. Park, M. J. Bick, B. Sankaran, R. A. Gillespie, P. J. M. Brouwer, P. H. Zwart, D. Veesler, M. Kanekiyo, B. S. Graham, R. Sanders, J. P. Moore, P. J. Klasse, A. B. Ward, N. King, D. Baker, Tailored Design of Protein Nanoparticle Scaffolds for Multivalent Presentation of Viral Glycoprotein Antigens, doi:10.1101/2020.01.29.923862.
16. M. Graille, E. A. Stura, A. L. Corper, B. J. Sutton, M. J. Taussig, J.-B. Charbonnier, G. J. Silverman, Crystal structure of a *Staphylococcus aureus* protein A domain complexed with the Fab fragment of a human IgM antibody: Structural basis for recognition of B-cell receptors and superantigen activity. Proceedings of the National Academy of Sciences. 97 (2000), pp. 5399-5404.
17. T. J. Brunette, F. Parmeggiani, P.-S. Huang, G. Bhabha, D. C. Ekiert, S. E. Tsutakawa, G. L. Hura, J. A. Tamer, D. Baker, Exploring the repeat protein universe through computational protein design. Nature. 528, 580-584 (2015).
18. J. A. Fallas, G. Ueda, W. Sheffler, V. Nguyen, D. E. McNamara, B. Sankaran, J. H. Pereira, F. Parmeggiani, T. J. Brunette, D. Cascio, T. R. Yeates, P. Zwart, D. Baker, Computational design of self-assembling cyclic protein homo-oligomers. Nat. Chem. 9, 353-360 (2017).
19. P.-S. Huang, G. Oberdorfer, C. Xu, X. Y. Pei, B. L. Nannenga, J. M. Rogers, F. DiMaio, T. Gonen, B. Luisi, D. Baker, High thermodynamic stability of parametrically designed helical bundles. Science. 346, 481-485 (2014).
20. I. Vulovic, Q. Yao, Y.-J. Park, A. Courbet, A. Norris, F. Busch, A. Sahasrabuddhe, H. Merten, D. D. Sahtoe, G. Ueda, J. A. Fallas, S. J. Weaver, Y. Hsia, R. A. Langan, A. Plückthun, V. H. Wysocki, D. Veesler, G. J. Jensen, D. Baker, Generation of ordered protein assemblies using rigid three-body fusion, doi:10.1101/2020.07.18.210294.
21. Y. Hsia, R. Mout, W. Sheffler, N. I. Edman, I. Vulovic, Y.-J. Park, R. L. Redler, M. J. Bick, A. K. Bera, A. Courbet, A. Kang, T. J. Brunette, U. Nattermann, E. Tsai, A. Saleem, C. M. Chow, D. Ekiert, G. Bhabha, D. Veesler, D. Baker, Hierarchical design of multi-scale protein complexes by combinatorial assembly of oligomeric helical bundle and repeat protein building blocks (2020).
22. T. O. Yeates, Y. Liu, J. Laniado, The design of symmetric protein nanomaterials comes of age in theory and practice. Curr. Opin. Struct. Biol. 39, 134-143 (2016).
23. B. M. Baynes, D. I. C. Wang, B. L. Trout, Role of arginine in the stabilization of proteins against aggregation. Biochemistry. 44, 4919-4925 (2005).
24. D. Schneidman-Duhovny, M. Hammel, J. A. Tamer, A. Sali, Accurate SAXS profile computation and its assessment by contrast variation experiments. Biophys. J. 105, 962-974 (2013).
25. J. L. Taupin, P. Legembre, J. Bitard, S. Daburon, V. Pitard, F. Blanchard, L. Duplomb, A. Godard, Y. Jacques, J. F. Moreau, Identification of agonistic and antagonistic antibodies against gp190, the leukemia inhibitory factor receptor, reveals distinct roles for its two cytokine-binding domains. J. Biol. Chem. 276, 47975-47981 (2001).
26. K. Mohan, G. Ueda, A. R. Kim, K. M. Jude, J. A. Fallas, Y. Guo, M. Hafer, Y. Miao, R. A. Saxton, J. Piehler, V. G. Sankaran, D. Baker, K. C. Garcia, Topological control of cytokine receptor signaling induces differential effects in hematopoiesis. Science. 364 (2019), doi:10.1126/science.aav7532.
27. J. D. Graves, J. J. Kordich, T.-H. Huang, J. Piasecki, T. L. Bush, T. Sullivan, I N. Foltz, W. Chang, H. Douangpanya, T. Dang, J. W. O'Neill, R. Mallari, X. Zhao, D. G. Branstetter, J. M. Rossi, A. M. Long, X. Huang, P. M. Holland, Apo2L/TRAIL and the death receptor 5 agonist antibody AMG 655 cooperate to promote receptor clustering and antitumor activity. Cancer Cell. 26, 177-189 (2014).
28. J. Naval, D. de Miguel, A. Gallego-Lleyda, A. Anel, L. Martinez-Lostao, Importance of TRAIL Molecular Anatomy in Receptor Oligomerization and Signaling. Implications for Cancer Therapy. Cancers. 11 (2019), doi:10.3390/cancers11040444.
29. D. de Miguel, J. Lemke, A. Anel, H. Walczak, L. Martinez-Lostao, Onto better TRAILs for cancer treatment. Cell Death Differ. 23, 733-747 (2016).
30. M. H. Tuthill, A. Montinaro, J. Zinngrebe, K. Prieske, P. Draber, S. Prieske, T. Newsom-Davis, S. von Karstedt, J. Graves, H. Walczak, TRAIL-R2-specific antibodies and recombinant TRAIL can synergise to kill cancer cells. Oncogene. 34, 2138-2144 (2015).
31. V.-M. Leppanen, P. Saharinen, K. Alitalo, Structural basis of Tie2 activation and Tie2/Tie1 heterodimerization. Proc. Natl. Acad. Sci. U.S.A 114, 4376-4381 (2017).
32. Y.-T. Zhao, J. A. Fallas, S. Saini, G. Ueda, L. Somasundaram, Z. Zhou, I. Xavier, D. Ehnes, C. Xu, L. Carter, S. Wrenn, J. Mathieu, D. L. Sellers, D. Baker, H. Ruohola-Baker, F-domain valency determines outcome of signaling through the Angiopoietin pathway (2020).
33. R. S. Kombluth, M. Stempniak, G. W. Stone, Design of CD40 agonists and their use in growing B cells for cancer immunotherapy. Int. Rev. Immunol. 31, 279-288 (2012).
34. R. H. Vonderheide, M. J. Glennie, Agonistic CD40 Antibodies and Cancer Therapy. Clinical Cancer Research. 19 (2013), pp. 1035-1043.
35. E. R. Steenblock, S. H. Wrzesinski, R. A. Flavell, T. M. Fahmy, Antigen presentation on artificial acellular substrates: modular systems for flexible, adaptable immunotherapy. Expert Opin. Biol. Ther. 9, 451-464 (2009).
36. J. V. Kim, J.-B. Latouche, I. Riviere, M. Sadelain, The ABCs of artificial antigen presentation. Nat. Biotechnol. 22, 403-410 (2004).
39. E. E. Idusogie, L. G. Presta, H. Gazzano-Santoro, K. Totpal, P. Y. Wong, M. Ultsch, Y. G. Meng, M. G. Mulkerrin, Mapping of the Clq binding site on rituxan, a chimeric antibody with a human IgG1 Fc. J. Immunol. 164, 4178-4184 (2000).
40. F. DiMaio, N. Echols, J. J. Headd, T. C. Terwilliger, P. D. Adams, D. Baker, Improved low-resolution crystallographic refinement with Phenix and Rosetta. Nature Methods. 10 (2013), pp. 1102-1104.
41. F. W. Studier, F. William Studier, Protein production by auto-induction in high-density shaking cultures. Protein Expression and Purification. 41 (2005), pp. 207-234.
42. J. K. Leman, B. D. Weitzner, S. M. Lewis, J. Adolf-Bryfogle, N. Alam, R. F. Alford, M. Aprahamian, D. Baker, K. A. Barlow, P. Barth, B. Basanta, B. J. Bender, K. Blacklock, J. Bonet, S. E. Boyken, P. Bradley, C. Bystroff, P. Conway, S. Cooper, B. E. Correia, B. Coventry, R. Das, R. M. De Jong, F. DiMaio, L. Dsilva, R. Dunbrack, A. S. Ford, B. Frenz, D. Y. Fu, C. Geniesse, L. Goldschmidt, R. Gowthaman, J. J. Gray, D. Gront, S. Guffy, S. Horowitz, P.-S. Huang, T. Huber, T. M. Jacobs, J. R. Jeliazkov, D. K. Johnson, K. Kappel, J. Karanicolas, H. Khakzad, K. R. Khar, S. D. Khare, F. Khatib, A. Khramushin, I. C. King, R. Kleffner, B. Koepnick, T. Kortemme, G. Kuenze, B. Kuhlman, D. Kuroda, J. W. Labonte, J. K. Lai, G. Lapidoth, A. Leaver-Fay, S. Lindert, T. Linsky, N. London, J. H. Lubin, S. Lyskov, J. Maguire, L. Malmstrom, E. Marcos, O. Marcu, N. A. Marze, J. Meiler, R. Moretti, V. K. Mulligan, S. Nerli, C. Nom, S. O'Conchnir, N. Ollikainen, S. Ovchinnikov, M. S. Pacella, X. Pan, H. Park, R. E. Pavlovicz, M. Pethe, B. G. Pierce, K. B. Pilla, B. Raveh, P. Douglas Renfrew, S. S. Roy Burman, A. Rubenstein, M. F. Sauer, A. Scheck, W. Schief, O. Schueler-Furman, Y. Sedan, A. M. Sevy, N. G. Sgourakis, L. Shi, J. B. Siegel, D.-A. Silva, S. Smith, Y. Song, A. Stein, M. Szegedy, F. D. Teets, S. B. Thyme, R. Y.-R. Wang, A. Watkins, L. Zimmerman, R. Bonneau, Macromolecular modeling and design in Rosetta: recent methods and frameworks. Nat. Methods. 17, 665-680 (2020).

43. L. Jendeberg, P. Nilsson, A. Larsson, P. Denker, M. Uhlén, B. Nilsson, P.-A. Nygren, Engineering of Fcl and Fc3 from human immunoglobulin G to analyse subclass specificity for staphylococcal protein A. Journal of Immunological Methods. 201 (1997), pp. 25-34.

44. D. Corti, S. Bianchi, F. Vanzetta, A. Minola, L. Perez, G. Agatic, B. Guarino, C. Silacci, J. Marcandalli, B. J. Marsland, A. Piralla, E. Percivalle, F. Sallusto, F. Baldanti, A. Lanzavecchia, Cross-neutralization of four paramyxoviruses by a human monoclonal antibody. Nature. 501, 439-443 (2013).

45. K. N. Dyer, M. Hammel, R. P. Rambo, S. E. Tsutakawa, I. Rodic, S. Classen, J. A. Tamer, G. L. Hura, High-throughput SAXS for the characterization of biomolecules in solution: a practical approach. Methods Mol. Biol. 1091, 245-258 (2014).

Materials and Methods

Computational Design and Testing of Fc-Binder Helical Repeat Protein (DHR79-FcB)

The crystal structure of the B-domain from *S. aureus* protein A in complex with Fc fragment (PDB ID: 1L6X) was relaxed with structure factors using Phenix Rosetta™ 39 40). Briefly, the RosettaScripts™ MotifGraft mover was used to assess suitable solutions to insertions of the protein A binding motif extracted from 1L6X into a previously reported designed helical repeat protein (DHR79) (17). Specifically, a minimal protein A binding motif was manually defined and extracted and used as a template for full backbone alignment of DHR79 while retaining user-specified hotspot residues that interact with the Fc domain in the crystal structure at the Fc/DHR interface and retaining native DHR residues in all other positions. The MotifGraft alignment was followed by 5 iterations of FastDesign and 5 iterations of FastRelax in which the DHR side chain and backbone rotamers were allowed to move while the Fc context was completely fixed. The best designs were selected based on a list of heuristic filter values.

Designs were initially assessed via yeast surface display binding to biotinylated Fc protein. Upon confirmation of a qualitative binding signal, the design was closed into a pET29b expression vector with a C-terminal His-tag. The protein was expressed in BL21 DE3 in autoinduction medium (10 mL 50×M, 10 mL 50×5052, 480 mL almost TB, 1× chloramphenicol, 1× kanamycin) for 20 hours at 27 °C at 225 rpm (41). Cells were resuspended in lysis buffer (20 mM Tris, 300 mM NaCl, 30 mM imidazole, 1 mM PMSF, 5% glycerol (v/v), pH 8.0) and lysed using a microfluidizer at 18000 PSI. Soluble fractions were separated via centrifugation at 24,000×g. IMAC with Ni-NTA batch resin was used for initial purification; briefly, nickel-nitrilotriacetic acid (Ni-NTA) resin was equilibrated with binding buffer (20 mM Tris, 300 mM NaCl, 30 mM imidazole, pH 8.0), soluble lysate was poured over the columns, columns were washed with 20 column volumes (CVs) of binding buffer, and eluted with 5 CVs of elution buffer (20 mM Tris, 300 mM NaCl, 500 mM imidazole, pH 8.0). Size exclusion chromatography (SEC) with a Superdex 200 column was used as the polishing step (FIG. 6*b*). SEC buffer was 20 mM Tris/HCl pH 7.4, 150 mM NaCl.

Affinity of DHR79-FcB to biotinylated IgG1 and biotinylated Fc protein was assessed using Octet™ Biolayer Interferometry (BLI). DHR79-FcB exhibits a 71.7 nM affinity to IgG1 (full antibody) and a 113 nM affinity to the IgG1 Fc protein (FIG. 6*c*).

Computational Design of Antibody Nanocages

Input pdb files were compiled to use as building blocks for the generation of antibody cages. For the protein A binder model, the Domain D from *Staphylococcus aureus* Protein A (PDB ID 1DEE) was aligned to the B-domain of protein A bound to Fc (PDB ID 1L6X) 16 39). The other Fc-binding design structure, where protein A was grafted onto a helical repeat protein, was also modeled with Fc from 1L6X. PDB file models for monomeric helical repeat protein linkers (42) and cyclic oligomers (2 C2s, 3 C3s, 1 C4, and 2 C5s) that had at least been validated via SAXS were compiled from previous work from our lab (17-19). Building block models were manually inspected to determine which amino acids were suitable for making fusions without disrupting existing protein-protein interfaces.

These building blocks were used as inputs, along with the specified geometry and fusion orientation, into the alpha helical fusion software (20, 21). Fusions were made by overlapping helical segments at all possible allowed amino acid sites. Fusions are then evaluated for deviation for which the cyclic symmetry axes intersect according to the geometric criteria: D2, T32, O32, O42, I32, and I52 intersection angles are 45.0°, 54.7°, 35.3°, 45.0°, 20.9°, and 31.7°, respectively (22) with angular and distance tolerances of at most 5.7° and 0.5 Å respectively. Post-fusion .pdb files were manually filtered to ensure that the N-termini of the Fc domains are facing outwards from the cage, so that the Fabs of an IgG would be external to the cage surface. Sequence design was performed using Rosetta™ symmetric sequence design (SymPackRotamersMover in RosettaScripts™) on residues at and around the fusion junctions (42), with a focus on maintaining as many of the native residues as possible. Residues were redesigned if they clashed with other residues, or if their chemical environment was changed after fusion (e.g. previously-core facing residues were now solvent-exposed). Index residue selectors were used to prevent design at Fc residue positions.

Structural Characterization of Antibody Nanocages

Genes were codon optimized for bacterial expression of each designed antibody-nanocage forming oligomers, with a C-terminal glycine/serine linker and 6×C-terminal histidine tag appended. Synthetic genes were cloned into pet29b+ vectors between NdeI and XhoI restriction sites; the plasmid contains a kanamycin-resistant gene and T7 promoter for protein expression. Plasmids were transformed into chemically competent Lemo21(DE3) *E. coli* bacteria using a 15-second heat shock procedure as described by the manufacturer (New England Biolabs). Transformed cells were added to auto-induction expression media, as described above, and incubated for 16 hours at 37 °C and 200 rpm shaking (41). Cells were pelleted by centrifugation at 4000×g and resuspended in lysis buffer (150 mM NaCl, 25 mM Tris-HCl, pH 8.0, added protease inhibitor and DNAse). Sonication was used to lyse the cells at 85% amplitude, with 15 second on/off cycles for a total of 2 minutes of sonication time. Soluble material was separated by centrifugation at 16000×g. IMAC was used to separate out the His-tagged protein in the soluble fraction as described above. IMAC elutions were concentrated to approximately 1 mL using 10K MWCO spin concentrators, filtered through a 0.22 uM spin filter, and run over SEC as a final polishing step (SEC running buffer: 150 mM NaCl, 25 mM Tris-HCl, pH 8.0).

Designs that produced monodisperse SEC peaks around their expected retention volume were combined with Fc from human IgG1. Fc was produced recombinantly either using standard methods for expression in HEK293T cells or in *E. coli* (43). Cage components were incubated at 4 °C for at minimum 30 minutes. 100 mM L-arginine was added during the assembly to AbCs formed with the i52.6 design, as this was observed to maximize the formation of the designed AbC i52.6 and minimize the formation of visible "crashed out" aggregates (23). Fc-binding and cage formation were confirmed via SEC; earlier shifts in retention time (compared to either component run alone) show the formation of a larger structure. NS-EM was used as previously described to confirm the structures of designs that passed these steps.

For confirming AbC structures with intact IgGs, human IgG1 (hIgG1) was combined with AbC-forming designs following the same protocol for making Fc cages. This assembly procedure was also followed for all IgG or Fc-fusion AbCs reported hereafter. The data in FIG. 2*d-e* shows AbCs formed with the α-DR5 antibody AMG-655 23 for the following designs: d2.3, d2.4, d2.7, t32.4, o42.1, and i52.3. The data for t32.8 and i52.6 designs shown in FIG. 2*d-e* is from AbCs formed with the hIgG1 antibody mpe8 (44). Tables 8 and 9 show the list of IgGs and Fc fusions that have been formed into AbCs.

Dynamic light scattering measurements (DLS) were performed using the default Sizing and Polydispersity method on the UNcle™ (Unchained Labs). 8.8 μL of AbCs were pipetted into the provided class cuvettes. DLS measurements were run in triplicate at 25 °C with an incubation time of 1 second; results were averaged across runs and plotted using Graphpad Prism. The estimated hydrodynamic diameter is listed next to all DLS peaks shown below.

NS-EM Analysis of Fc and IRG AbCs

For all samples except o42.1 Fc and i52.3 Fc, 3.0 μL of each SEC-purified sample between 0.008-0.014 mg/mL in TBS pH 8.0 was applied onto a 400-mesh or 200-mesh Cu grid glow-discharged carbon-coated copper grids for 20 seconds, followed by 2× application of 3.0 μL 2% nano-W stain. Micrographs were recorded using Leginon software on a 120 kV FEI Tecnai G2 Spirit™ with a Gatan Ultrascan™ 4000 4k×4k CCD camera at 67,000 nominal magnification (pixel size 1.6 Å/pixel) or 52,000 nominal magnification (pixel size 2.07 Å) at a defocus range of 1.5-2.5 in. Particles were picked either with DoGPicker or cisTEM; both are reference-free pickers. Contrast-transfer function was estimated using GCTF or cisTEM. 2D class averages were generated in cryoSPARC or in cisTEM. Reference-free ab initio 3D reconstruction of selected 2D class averages from each dataset was performed in cryoSPARC or in cisTEM (Table 10).

TABLE 10

Details on data acquisition and data processing of different nanocages samples.

| Sample name | Stain | Voltage (kV) | Magnification | Pixel size (Å/pixel) | Particle picking | CTF estimation | 2D class averages | 3D reconstruction |
|---|---|---|---|---|---|---|---|---|
| d2.3 Fc | UF | 120 | 67,000 | 1.6 | cisTEM | cisTEM | cisTEM | cisTEM |
| d2.4 Fc | UF | 120 | 67,000 | 1.6 | DoG picker | GCTF | cryoSPARC | cryoSPARC |
| d2.7 Fc | nano-W | 120 | 67,000 | 1.6 | cisTEM | cisTEM | cisTEM | cisTEM |
| t32.4 Fc | nano-W | 120 | 67,000 | 1.6 | cisTEM | cisTEM | cisTEM | cisTEM |
| t32.8 Fc | nano-W | 120 | 67,000 | 1.6 | cisTEM | cisTEM | cisTEM | cisTEM |
| o42.1 Fc | cryo | 200 | 36,000 | 1.16 | Manual picking | GCTF | cryoSPARC | cryoSPARC |
| i52.3 Fc | cryo | 200 | 36,000 | 1.16 | Manual picking | GCTF | cryoSPARC | cryoSPARC |
| i52.6 Fc | nano-W | 120 | 52,000 | 2.07 | cisTEM | cisTEM | cisTEM | cisTEM |
| d2.3 hIgG1 | UF | 120 | 67,000 | 1.6 | cisTEM | cisTEM | cisTEM | N/A |
| d2.4 hIgG1 | UF | 120 | 67,000 | 1.6 | cisTEM | cisTEM | cisTEM | N/A |
| d2.7 hIgG1 | nano-W | 120 | 67,000 | 1.6 | cisTEM | cisTEM | cisTEM | N/A |
| t32.4 hIgG1 | nano-W | 120 | 67,000 | 1.6 | cisTEM | cisTEM | cisTEM | N/A |
| t32.8 hIgG1 | nano-W | 120 | 67,000 | 1.6 | cisTEM | cisTEM | cisTEM | N/A |
| o42.1 hIgG1 | UF | 120 | 67,000 | 1.6 | DoG picker | GCTF | cryoSPARC | N/A |
| i52.3 hIgG1 | nano-W | 120 | 52,000 | 2.07 | cisTEM | cisTEM | cisTEM | N/A |
| i52.6 hIgG1 | nano-W | 120 | 52,000 | 2.07 | cisTEM | cisTEM | cryoSPARC | N/A |
| D3-08 Fc | nano-W | 120 | 57,000 | 2.52 | cisTEM | cisTEM | cisTEM | cisTEM |
| D3-36 Fc | nano-W | 120 | 57,000 | 2.52 | cisTEM | cisTEM | cisTEM | cisTEM |

Cryo-EM Analysis of o42.1 and i52.3 AbCs 3.0 μL of i52.3 Fc sample at 0.8 mg/mL in TBS pH 8.0 with 100 mM Arginine was applied onto C-flat 1.2 μm glow-discharged copper grids. Grids were then plunge-frozen in liquid ethane, cooled with liquid nitrogen using and FEI MK4 Vitrobot with a 6 second blotting time and 0 force. The blotting process took place inside the Vitrobot chamber at 20 °C and 100% humidity. Data acquisition was performed with the Leginon data collection software on an FEI Talos electron microscope at 200 kV and a Gatan K2 Summit camera. The nominal magnification was 36,000× with a pixel size of 1.16 Å/pixel. The dose rate was adjusted to 8 counts/pixel/s. Each movie was acquired in counting mode fractionated in 50 frames of 200 ms/frame. Frame alignment was performed with MotionCorr2. Particles were manually picked within the Appion interface. Defocus parameters were estimated with GCTF. Reference-free 2D classification with cryoSPARC was used to select a subset of particles for Ab-Initio 3D reconstruction function in cryoSPARC.

A summary of data acquisition and processing is provided in Table 11.

DR5 and A1F-Fc Experiments

Cell Culture

Colorectal adenocarcinoma cell line-Colo205, and renal cell carcinoma cell line RCC4 were obtained from ATCC. Primary kidney tubular epithelial cells RAM009 were a gift from Dr. Akilesh (University of Washington). Colo205 cells were grown in RPMI1640 medium with 10% Fetal Bovine Serum (FBS) and penicillin/streptomycin. RCC4 cells were grown in Dulbecco's Modified Eagle's Medium with 10% FBS and penicillin/streptomycin. RAM009 were grown in RPMI with 10% FBS, ITS-supplement, penicillin/streptomycin and Non Essential Amino Acids (NEAA). All cell lines were maintained at 37 °C in a humidified atmosphere containing 5% CO2.

Human Umbilical Vein Endothelial Cells (HUVECs, Lonza, Germany, catalog #C2519AS) were grown on 0.1% gelatin-coated 35 mm cell culture dish in EGM2 media. Briefly, EGM2 consist of 20% Fetal Bovine Serum, 1% penicillin-streptomycin, 1% Glutamax (Gibco, catalog #35050061), 1% endothelial cell growth factor (31), 1 mM sodium pyruvate, 7.5 mM HEPES, 0.08 mg/mL heparin, 0.01% amphotericin B, a mixture of 1×RPMI 1640 with and without glucose to reach 5.6 mM glucose concentration in the final volume. Media was filtered through a 0.45-micrometer filter. HUVECs at passage 7 were utilized in Tie2 signaling and cell migration experiments. HUVECs at passage 6 were used in tube formation assay.

Caspase 3/7 Glo Assay

Cells were passaged using trypsin and 20,000 cells/well were plated onto a 96-well white tissue culture plate and grown in appropriate media. Medium was changed the next day (100 μL/well) and cells were treated with either uncaged α-DR5 AMG655 antibody (150 nM), recombinant human TNF Related Apoptosis Inducing Ligand (rhTRAIL; 150 nM), Fc-only AbCs or α-DR5 AbCs (150 nM, 1.5 nM, 15 μM) and incubated at 37 °C for 24 hours. The following day 100 μL/well of caspase GLO™ reagent (Promega, USA) was added on top of the media and incubated for 2 hours at 37 °C. Luminescence was then recorded using Perkin EnVision microplate reader (Perkin Elmer). Statistical comparisons were performed using Graphpad Prism™ (see Table 11 for full detail).

TABLE 11

Statistical information for DR5 experiments.

| Experiment (FIG.) | Condition | Concentration | n | Test | Mean compared to | α | Summary | Adjusted P value |
|---|---|---|---|---|---|---|---|---|
| Caspase-3,7 RCC4 (4b) | PBS | 15 pM | 6 | 2way ANOVA with post-hoc Dunnett | N/A | N/A | N/A | N/A |
| | | 1.5 nM | 6 | 2way ANOVA with post-hoc Dunnett | 15 pM PBS | 0.05 | ns | 0.9996 |
| | | 150 nM | 6 | 2way ANOVA with post-hoc Dunnett | 15 pM PBS | 0.05 | ns | 0.9994 |
| | TRAIL | 15 pM | 6 | 2way ANOVA with post-hoc Dunnett | 15 pM PBS | 0.05 | ns | 0.9996 |
| | | 1.5 nM | 6 | 2way ANOVA with post-hoc Dunnett | 15 pM PBS | 0.05 | ns | 0.9996 |
| | | 150 nM | 6 | 2way ANOVA with post-hoc Dunnett | 15 pM PBS | 0.05 | ns | 0.9668 |
| | α-DR5 | 15 pM | 6 | 2way ANOVA with post-hoc Dunnett | 15 pM PBS | 0.05 | ns | 0.9997 |
| | | 1.5 nM | 6 | 2way ANOVA with post-hoc Dunnett | 15 pM PBS | 0.05 | ns | >0.9999 |
| | | 150 nM | 6 | 2way ANOVA with post-hoc Dunnett | 15 pM PBS | 0.05 | ns | 0.2005 |
| | d2.4 α-DR5 | 15 pM | 6 | 2way ANOVA with post-hoc Dunnett | 15 pM PBS | 0.05 | ns | 0.9995 |
| | | 1.5 nM | 6 | 2way ANOVA with post-hoc Dunnett | 15 pM PBS | 0.05 | ns | 0.9988 |
| | | 150 nM | 6 | 2way ANOVA with post-hoc Dunnett | 15 pM PBS | 0.05 | **** | <0.0001 |
| | t32.4 α-DR5 | 15 pM | 6 | 2way ANOVA with post-hoc Dunnett | 15 pM PBS | 0.05 | ns | 0.9998 |
| | | 1.5 nM | 6 | 2way ANOVA with post-hoc Dunnett | 15 pM PBS | 0.05 | **** | <0.0001 |
| | | 150 nM | 6 | 2way ANOVA with post-hoc Dunnett | 15 pM PBS | 0.05 | **** | <0.0001 |
| | t32.8 α-DR5 | 15 pM | 3 | 2way ANOVA with post-hoc Dunnett | 15 pM PBS | 0.05 | ns | 0.984 |
| | | 1.5 nM | 3 | 2way ANOVA with post-hoc Dunnett | 15 pM PBS | 0.05 | ns | 0.6177 |
| | | 150 nM | 3 | 2way ANOVA with post-hoc Dunnett | 15 pM PBS | 0.05 | **** | <0.0001 |
| | o42.1 α-DR5 | 15 pM | 6 | 2way ANOVA with post-hoc Dunnett | 15 pM PBS | 0.05 | ns | 0.9991 |
| | | 1.5 nM | 6 | 2way ANOVA with post-hoc Dunnett | 15 pM PBS | 0.05 | **** | <0.0001 |
| | | 150 nM | 6 | 2way ANOVA with post-hoc Dunnett | 15 pM PBS | 0.05 | **** | <0.0001 |

TABLE 11-continued

Statistical information for DR5 experiments.

| Experiment (FIG.) | Condition | Concen-tration | n | Test | Mean compared to | α | Summary | Adjusted P value |
|---|---|---|---|---|---|---|---|---|
| | i52.3 α-DR5 | 15 pM | 3 | 2way ANOVA with post-hoc Dunnett | 15 pM PBS | 0.05 | ns | 0.9442 |
| | | 1.5 nM | 3 | 2way ANOVA with post-hoc Dunnett | 15 pM PBS | 0.05 | ns | 0.8227 |
| | | 150 nM | 3 | 2way ANOVA with post-hoc Dunnett | 15 pM PBS | 0.05 | **** | <0.0001 |
| Viability 4d RCC4 (4c) | PBS | 150 nM | 3 | 1way ANOVA with post-hoc Dunnett | N/A | N/A | N/A | N/A |
| | TRAIL | 150 nM | 3 | 1way ANOVA with post-hoc Dunnett | PBS | 0.05 | ns | 0.5207 |
| | α-DR5 | 150 nM | 3 | 1way ANOVA with post-hoc Dunnett | PBS | 0.05 | ns | 0.9996 |
| | d2.4 α-DR5 | 150 nM | 3 | 1way ANOVA with post-hoc Dunnett | PBS | 0.05 | * | 0.0238 |
| | t32.4 α-DR5 | 150 nM | 3 | 1way ANOVA with post-hoc Dunnett | PBS | 0.05 | **** | <0.0001 |
| | t32.8 α-DR5 | 150 nM | 3 | 1way ANOVA with post-hoc Dunnett | PBS | 0.05 | **** | <0.0001 |
| | o42.1 α-DR5 | 150 nM | 3 | 1way ANOVA with post-hoc Dunnett | PBS | 0.05 | **** | <0.0001 |
| | i52.3 α-DR5 | 150 nM | 3 | 1way ANOVA with post-hoc Dunnett | PBS | 0.05 | ** | 0.0079 |
| Viability 4d RCC4 Fc cages (4d) | PBS | 150 nM | 3 | 1way ANOVA with post-hoc Dunnett | N/A | N/A | N/A | N/A |
| | d2.4 Fc | 150 nM | 3 | 1way ANOVA with post-hoc Dunnett | PBS | 0.05 | ns | 0.7157 |
| | t32.4 Fc | 150 nM | 3 | 1way ANOVA with post-hoc Dunnett | PBS | 0.05 | ns | 0.9976 |
| | t32.8 Fc | 150 nM | 3 | 1way ANOVA with post-hoc Dunnett | PBS | 0.05 | ns | 0.8556 |
| | o42.1 Fc | 150 nM | 3 | 1way ANOVA with post-hoc Dunnett | PBS | 0.05 | ns | 0.2309 |
| | i52.3 Fc | 150 nM | 3 | 1way ANOVA with post-hoc Dunnett | PBS | 0.05 | ns | 0.9302 |
| Viability 6d RCC4 (4e) | PBS | 150 nM | 6 | 1way ANOVA with post-hoc Dunnett | N/A | N/A | N/A | N/A |
| | TRAIL | 150 nM | 6 | 1way ANOVA with post-hoc Dunnett | PBS | 0.05 | ns | 0.9996 |
| | α-DR5 | 150 nM | 6 | 1way ANOVA with post-hoc Dunnett | PBS | 0.05 | ns | >0.9999 |
| | t32.4 Fc | 150 nM | 3 | 1way ANOVA with post-hoc Dunnett | PBS | 0.05 | ns | 0.9591 |
| | o42.1 Fc | 150 nM | 3 | 1way ANOVA with post-hoc Dunnett | PBS | 0.05 | ns | 0.9593 |
| | t32.4 α-DR5 | 150 nM | 6 | 1way ANOVA with post-hoc Dunnett | PBS | 0.05 | **** | <0.0001 |
| | o42.1 α-DR5 | 150 nM | 6 | 1way ANOVA with post-hoc Dunnett | PBS | 0.05 | *** | 0.0001 |
| c-PARP quant. (4g) | PBS | 150 nM | 4 | 1way ANOVA with post-hoc Dunnett | N/A | N/A | N/A | N/A |
| | TRAIL | 150 nM | 4 | 1way ANOVA with post-hoc Dunnett | PBS | 0.05 | ns | 0.0845 |
| | α-DR5 | 150 nM | 3 | 1way ANOVA with post-hoc Dunnett | PBS | 0.05 | ns | 0.4746 |
| | o42.1 Fc | 150 nM | 3 | 1way ANOVA with post-hoc Dunnett | PBS | 0.05 | ns | 0.9979 |
| | o42.1 α-DR5 | 150 nM | 3 | 1way ANOVA with post-hoc Dunnett | PBS | 0.05 | **** | <0.0001 |
| Caspase-3,7 Colo205 | PBS | 15 pM | 2 | 2way ANOVA with post-hoc Dunnett | N/A | N/A | N/A | N/A |
| | | 1.5 nM | 2 | 2way ANOVA with post-hoc Dunnett | 15 pM PBS | 0.05 | ns | >0.9999 |
| | | 150 nM | 2 | 2way ANOVA with post-hoc Dunnett | 15 pM PBS | 0.05 | ns | >0.9999 |
| | TRAIL | 15 pM | 2 | 2way ANOVA with post-hoc Dunnett | 15 pM PBS | 0.05 | ns | >0.9999 |
| | | 1.5 nM | 2 | 2way ANOVA with post-hoc Dunnett | 15 pM PBS | 0.05 | *** | 0.0006 |
| | | 150 nM | 2 | 2way ANOVA with post-hoc Dunnett | 15 pM PBS | 0.05 | **** | <0.0001 |

TABLE 11-continued

Statistical information for DR5 experiments.

| Experiment (FIG.) | Condition | Concen-tration | n | Test | Mean compared to | α | Summary | Adjusted P value |
|---|---|---|---|---|---|---|---|---|
| | α-DRS | 15 pM | 2 | 2way ANOVA with post-hoc Dunnett | 15 pM PBS | 0.05 | ns | 0.9997 |
| | | 1.5 nM | 2 | 2way ANOVA with post-hoc Dunnett | 15 pM PBS | 0.05 | ns | >0.9999 |
| | | 150 nM | 2 | 2way ANOVA with post-hoc Dunnett | 15 pM PBS | 0.05 | ns | 0.9996 |
| | d2.4 α-DR5 | 15 pM | 2 | 2way ANOVA with post-hoc Dunnett | 15 pM PBS | 0.05 | ns | 0.9996 |
| | | 1.5 nM | 2 | 2way ANOVA with post-hoc Dunnett | 15 pM PBS | 0.05 | **** | <0.0001 |
| | | 150 nM | 2 | 2way ANOVA with post-hoc Dunnett | 15 pM PBS | 0.05 | **** | <0.0001 |
| | t32.4 α-DR5 | 15 pM | 2 | 2way ANOVA with post-hoc Dunnett | 15 pM PBS | 0.05 | ns | 0.1074 |
| | | 1.5 nM | 2 | 2way ANOVA with post-hoc Dunnett | 15 pM PBS | 0.05 | **** | <0.0001 |
| | | 150 nM | 2 | 2way ANOVA with post-hoc Dunnett | 15 pM PBS | 0.05 | **** | <0.0001 |
| | t32.8 α-DR5 | 15 pM | 2 | 2way ANOVA with post-hoc Dunnett | 15 pM PBS | 0.05 | ns | >0.9999 |
| | | 1.5 nM | 2 | 2way ANOVA with post-hoc Dunnett | 15 pM PBS | 0.05 | **** | <0.0001 |
| | | 150 nM | 2 | 2way ANOVA with post-hoc Dunnett | 15 pM PBS | 0.05 | **** | <0.0001 |
| | o42.1 α-DR5 | 15 pM | 2 | 2way ANOVA with post-hoc Dunnett | 15 pM PBS | 0.05 | ns | 0.6538 |
| | | 1.5 nM | 2 | 2way ANOVA with post-hoc Dunnett | 15 pM PBS | 0.05 | **** | <0.0001 |
| | | 150 nM | 2 | 2way ANOVA with post-hoc Dunnett | 15 pM PBS | 0.05 | **** | <0.0001 |
| | i52.3 α-DR5 | 15 pM | 2 | 2way ANOVA with post-hoc Dunnett | 15 pM PBS | 0.05 | ns | >0.9999 |
| | | 1.5 nM | 2 | 2way ANOVA with post-hoc Dunnett | 15 pM PBS | 0.05 | **** | <0.0001 |
| | | 150 nM | 2 | 2way ANOVA with post-hoc Dunnett | 15 pM PBS | 0.05 | **** | <0.0001 |
| Caspase-3,7 RCC4 Fc | PBS | 150 nM | 3 | 1way ANOVA with post-hoc Dunnett | N/A | N/A | N/A | N/A |
| | d2.4 Fc | 150 nM | 6 | 1way ANOVA with post-hoc Dunnett | PBS | 0.05 | * | 0.0129 |
| | t32.4 Fc | 150 nM | 6 | 1way ANOVA with post-hoc Dunnett | PBS | 0.05 | * | 0.046 |
| | t32.8 Fc | 150 nM | 3 | 1way ANOVA with post-hoc Dunnett | PBS | 0.05 | ns | 0.9198 |
| | o42.1 Fc | 150 nM | 6 | 1way ANOVA with post-hoc Dunnett | PBS | 0.05 | ns | 0.2112 |
| | i52.3 Fc | 150 nM | 3 | 1way ANOVA with post-hoc Dunnett | PBS | 0.05 | ns | 0.9996 |
| RAM009 Caspase-3,7 | PBS | 1.5 nM | 6 | 2way ANOVA with post-hoc Dunnett | PBS | 0.05 | N/A | N/A |
| | | 150 nM | 6 | 2way ANOVA with post-hoc Dunnett | PBS | 0.05 | ns | 0.3848 |
| | TRAIL | 1.5 nM | 6 | 2way ANOVA with post-hoc Dunnett | PBS | 0.05 | ns | 0.9726 |
| | | 150 nM | 6 | 2way ANOVA with post-hoc Dunnett | PBS | 0.05 | ns | 0.0525 |
| | α-DR5 | 1.5 nM | 6 | 2way ANOVA with post-hoc Dunnett | PBS | 0.05 | ns | 0.9566 |
| | | 150 nM | 6 | 2way ANOVA with post-hoc Dunnett | PBS | 0.05 | ns | 0.2752 |
| | d2.4 α-DR5 | 1.5 nM | 6 | 2way ANOVA with post-hoc Dunnett | PBS | 0.05 | ns | 0.9677 |
| | | 150 nM | 6 | 2way ANOVA with post-hoc Dunnett | PBS | 0.05 | ** | 0.0076 |
| | t32.4 α-DR5 | 1.5 nM | 6 | 2way ANOVA with post-hoc Dunnett | PBS | 0.05 | ns | 0.9703 |
| | | 150 nM | 6 | 2way ANOVA with post-hoc Dunnett | PBS | 0.05 | ** | 0.0028 |
| | t32.8 α-DR5 | 1.5 nM | 6 | 2way ANOVA with post-hoc Dunnett | PBS | 0.05 | ns | 0.9996 |
| | | 150 nM | 6 | 2way ANOVA with post-hoc Dunnett | PBS | 0.05 | ** | 0.0067 |

TABLE 11-continued

Statistical information for DR5 experiments.

| Experiment (FIG.) | Condition | Concentration | n | Test | Mean compared to | α | Summary | Adjusted P value |
|---|---|---|---|---|---|---|---|---|
| | o42.1 α-DR5 | 1.5 nM | 6 | 2way ANOVA with post-hoc Dunnett | PBS | 0.05 | ns | 0.9991 |
| | | 150 nM | 6 | 2way ANOVA with post-hoc Dunnett | PBS | 0.05 | ** | 0.0038 |
| | i52.3 α-DR5 | 1.5 nM | 6 | 2way ANOVA with post-hoc Dunnett | PBS | 0.05 | ns | 0.9994 |
| | | 150 nM | 6 | 2way ANOVA with post-hoc Dunnett | PBS | 0.05 | *** | 0.0006 |
| | d2.4 Fc | 150 nM | 6 | 2way ANOVA with post-hoc Dunnett | PBS | 0.05 | ns | 0.9966 |
| | t32.4 Fc | 150 nM | 6 | 2way ANOVA with post-hoc Dunnett | PBS | 0.05 | ns | 0.9997 |
| | t32.8 Fc | 150 nM | 6 | 2way ANOVA with post-hoc Dunnett | PBS | 0.05 | ns | 0.9992 |
| | o42.1 Fc | 150 nM | 6 | 2way ANOVA with post-hoc Dunnett | PBS | 0.05 | ns | 0.9994 |
| | i52.3 Fc | 150 nM | 6 | 2way ANOVA with post-hoc Dunnett | PBS | 0.05 | ns | 0.9995 |
| RAM009 Viability | PBS | 150 nM | 6 | 2way ANOVA with post-hoc Dunnett | PBS | 0.05 | | |
| | TRAIL | 150 nM | 3 | 2way ANOVA with post-hoc Dunnett | PBS | 0.05 | ns | 0.9901 |
| | α-DR5 | 150 nM | 3 | 2way ANOVA with post-hoc Dunnett | PBS | 0.05 | ns | 0.9995 |
| | d2.4 α-DR5 | 150 nM | 3 | 2way ANOVA with post-hoc Dunnett | PBS | 0.05 | ns | 0.9996 |
| | t32.4 α-DR5 | 150 nM | 3 | 2way ANOVA with post-hoc Dunnett | PBS | 0.05 | ns | 0.9212 |
| | t32.8 α-DR5 | 150 nM | 3 | 2way ANOVA with post-hoc Dunnett | PBS | 0.05 | ns | 0.7875 |
| | o42.1 α-DR5 | 150 nM | 3 | 2way ANOVA with post-hoc Dunnett | PBS | 0.05 | ns | 0.7485 |
| | i52.3 α-DR5 | 150 nM | 3 | 2way ANOVA with post-hoc Dunnett | PBS | 0.05 | ns | 0.1419 |
| | d2.4 Fc | 150 nM | 3 | 2way ANOVA with post-hoc Dunnett | PBS | 0.05 | ns | 0.9996 |
| | t32.4 Fc | 150 nM | 3 | 2way ANOVA with post-hoc Dunnett | PBS | 0.05 | ns | 0.9718 |
| | t32.8 Fc | 150 nM | 3 | 2way ANOVA with post-hoc Dunnett | PBS | 0.05 | ns | 0.999 |
| | o42.1 Fc | 150 nM | 3 | 2way ANOVA with post-hoc Dunnett | PBS | 0.05 | ns | 0.9913 |
| | i52.3 Fc | 150 nM | 3 | 2way ANOVA with post-hoc Dunnett | PBS | 0.05 | ns | 0.9837 |

Titer Glo Cell Viability Assay (4 Day Viability)

Cells were plated onto a 96-well plate at 20,000 cells/well. The next day, cells were treated with 150 nM of α-DR5 AbCs, rhTRAIL and α-DR5 antibody for 4 days. At day 4, 100 μL of CellTiter-Glo reagent (Promega Corp. USA, #G7570) was added to the 100 μL of media per well, incubated for 10 min at 37 °C and luminescence was measured using a Perkin-Elmer Envision plate reader.

Alamar Blue Cell Viability Assay (6 Day Viability)

Cells were seeded onto a 12-well tissue culture plate at 50,000 cells/well. The next day, cells were treated with α-DR5 AbCs, rhTRAIL, or α-DR5 antibodies at 150 nM concentration. Three days later, cells were passaged at 30,000 cells/well and treated with 150 nM of α-DR5 cages, rhTRAIL and α-DR5 antibody for 3 days. At 6 days, the media was replaced with 450 μL/well of fresh media and 50 μL of Alamar™ blue reagent (Thermofisher Scientific, USA, #DAL1025) was then added. After 4 hours of incubation at 37 °C, 50 μL of media was transferred into a 96-well opaque white plate and fluorescence intensity was measured using plate reader according to manufacturer's instructions.

Protein Analysis

Cells were passaged onto a 12-well plate at 40,000 cells/well and were grown until 80% confluency is reached. Before treatment, the media was replaced with 500 μL of fresh media. For DR5 experiments, AMG-655 antibody and rhTRAIL were added at 150 nM concentration and Fc-only nanocages or α-DR5 nanocages were added at 150 nM, 1.5 nM and 15 pM concentration onto the media and incubated for 24 hours at 37 °C prior to protein isolation.

Media containing dead cells was transferred to a 1.5 ml Eppendorf tube, and the cells were gently rinsed with 1× phosphate buffered saline. 1× trypsin was added to the cells for 3 min. All the cells were collected into the 1.5 mL Eppendorf containing the medium with dead cells. Cells were washed once in PBS 1× and lysed with 70 μL of lysis buffer containing 20 mM Tris-HCl (pH 7.5), 150 mM NaCl, 15% Glycerol, 1% Triton, 3% SDS, 25 mM β-glycerophosphate, 50 mM NaF, 10 mM Sodium Pyrophosphate, 0.5% Orthovanadate, 1% PMSF (all chemicals were from Sigma-Aldrich, St. Louis, MO), 25 U Benzonase Nuclease (EMD Chemicals, Gibbstown, NJ), protease inhibitor cocktail (Pierce™ Protease Inhibitor Mini Tablets, Thermo Scientific, USA), and phosphatase inhibitor cocktail 2 (catalog #P5726), in their respective tubes. Total protein samples were then treated with 1 μL of Benzonase (Novagen, USA) and incubated at 37 °C for 10 min. 21.6 μL of 4× Laemmli Sample buffer (Bio-Rad, USA) containing 10% beta-mercaptoethanol was added to the cell lysate and then heated at 95 °C for 10 minutes. The boiled samples were either used for Western blot analysis or stored at −80 °C.

Production of A1F-Fc

Synthetic genes were optimized for mammalian expression and subcloned into the CMV/R vector (VRC 8400; PMID:15994776). XbaI and AvrII restriction sites were used for insertion of A1F-Fc. Gene synthesis and cloning was performed by Genscript. Expi 293F cells were grown in suspension using Expi293 Expression Medium (Thermo Fisher Scientific) at 150 RPM, 5% CO2, 70% humidity, 37 °C. At confluency of ~$2.5\times10^6$ cells/mL, the cells were transfected with the vector encoding A1F-Fc (1000 μg per 1 L of cells) using PEI MAX (Polysciences) as a transfection reagent. Cells were incubated for 96 hours, after which they were spun down by centrifugation (4,000×g, 10 min, 4 °C) and the protein-containing supernatant was further clarified by vacuum-filtration (0.45 μm, Millipore Sigma). In preparation of nickel-affinity chromatography steps, 50 mM Tris, 350 mM NaCl, pH 8.0 was added to clarified supernatant. For each liter of supernatant, 4 mL of Ni Sepharose™ excel resin (GE) was added to the supernatant, followed by overnight shaking at 4 °C. After 16-24 hours, resin was collected and separated from the mixture and washed twice with 50 mM Tris, 500 mM NaCl, 30 mM imidazole, pH 8.0 prior to elution of desired protein with 50 mM Tris, 500 mM NaCl, 300 mM imidazole, pH 8.0. Eluates were purified by SEC using a Superdex™ 200 Increase column.

Western Blotting

The protein samples were thawed and heated at 95 °C for 10 minutes. 10 μL of protein sample per well was loaded and separated on a 4-10% SDS-PAGE gel for 30 minutes at 250 Volt. The proteins were then transferred onto a Nitrocellulose membrane for 12 minutes using the semi-dry turbo transfer western blot apparatus (Bio-Rad, USA). Post-transfer, the membrane was blocked in 5% nonfat dry milk for 1 hour. After 1 hour, the membrane was probed with the respective antibodies: cleaved-PARP (Cell Signaling, USA) at 1:2000 dilution; cFLIP (R&D systems, USA) at 1:1000 dilution; pERK1/2 (Cell Signaling) at 1:5000 dilution; pFAK (Cell Signaling) at 1:1000 dilution; p-AKT(5473) (Cell Signaling) at 1:2000 dilution; and actin (Cell Signaling, USA) at 1:10,000 dilution. Separately, for p-AKT(5473) the membrane was blocked in 5% BSA for 3 hours followed by primary antibody addition. Membranes with primary antibodies were incubated on a rocker at 4 °C, overnight. Next day, the membranes were washed with 1×TBST (3 times, 10 minutes interval) and the respective HRP-conjugated secondary antibody (Bio-Rad, USA) (1:10,000) was added and incubated at room temperature for 1 hour. For p-AKT(5473), following washes, the membrane was blocked in 5% milk at room temperature for 1 hour and then incubated in the respective HRP-conjugated secondary antibody (1:2000) prepared in 5% milk for 2 hours. After secondary antibody incubation, all the membranes were washed with 1×TBST (3 times, 10 minutes interval) and developed using Luminol reagent and imaged using Bio-Rad ChemiDoc™ Imager. Data were quantified using the ImageJ™ software to analyze band intensity. Quantifications were done by calculating the peak area for each band. Each signal was normalized to the actin quantification from that lane of the same gel, to allow for cross-gel comparisons. Fold-changes were then calculated compared to PBS for all samples except for the pAKT reported for the ATF-Fc western blot (there was not enough pAKT signal for comparison, so o42.1 ATF-Fc was used for normalization). Statistical comparisons were performed using Graphpad Prism™ (see Tables 11, 12 for full detail).

Cell Migration ("Scratch") Assay

Passage 7 HUVECs were seeded onto 35 mm, 0.100 gelatin-coated plates and cultured in FGM-2. Once a monolayer of cells has been established, a scratch is made on the cell layer using a 200 μL pipette tip. Media is changed to DMFM Low glucose supplemented with 2% o Fetal Bovine Serum. Scaffolds were added into the media at 18 nM A1F-Fc concentrations. The imaging was performed in Leica Microscope at 10× magnification under phase contrast at 0 and 12 hours. The images are quantified using ImageJ software to calculate the level of cell migration as a ratio of change in wound area to initial wound area. Level of cell migration is normalized to PBS. Statistical comparisons were performed using Graphpad Prism (see Table 12 for full detail).

TABLE 12

Statistical information for A1F-Fe experiments.

| Experiment (FIG.) | Condition | n | Test | Mean compared to | α | Summary | Adjusted P value |
|---|---|---|---|---|---|---|---|
| pAKT (4j, 9c (H8)) | PBS | 13 | 1way ANOVA with post-hoc Dunnett | N/A | N/A | N/A | N/A |
| | A1F-Fc | 3 | 1way ANOVA with post-hoc Dunett | PBS | 0.05 | ns | >0.9999 |
| | o42.1 Fc | 4 | 1way ANOVA with post-hoc Dunnett | PBS | 0.05 | ns | >0.9999 |
| | i52.3 Fc | 3 | 1way ANOVA with post-hoc Dunnett | PBS | 0.05 | ns | >0.9999 |
| | o42.1 A1F-Fc | 9 | 1way ANOVA with post-hoc Dunnett | PBS | 0.05 | **** | <0.0001 |
| | i52.3 A1F-Fc | 8 | 1way ANOVA with post-hoc Dunnett | PBS | 0.05 | **** | <0.0001 |

TABLE 12-continued

Statistical information for A1F-Fe experiments.

| Experiment (FIG.) | Condition | n | Test | Mean compared to | α | Summary | Adjusted P value |
|---|---|---|---|---|---|---|---|
| | H8-A1F | 4 | 1way ANOVA with post-hoc Dunnett | PBS | 0.05 | **** | <0.0001 |
| pERK1-2 (4j; 9c (H8)) | PBS | 13 | 1way ANOVA with post-hoc Dunnett | N/A | N/A | N/A | N/A |
| | A1F-Fc | 3 | 1way ANOVA with post-hoc Dunnett | PBS | 0.05 | ns | 0.9997 |
| | o42.1 Fc | 4 | 1way ANOVA with post-hoc Dunnett | PBS | 0.05 | ns | 0.9957 |
| | i52.3 Fc | 3 | 1way ANOVA with post-hoc Dunnett | PBS | 0.05 | ns | 0.9997 |
| | o42.1 A1F-Fc | 9 | 1way ANOVA with post-hoc Dunnett | PBS | 0.05 | ** | 0.0032 |
| | i52.3 A1F-Fc | 8 | 1way ANOVA with post-hoc Dunnett | PBS | 0.05 | **** | <0.0001 |
| | H8-A1F | 6 | 1way ANOVA with post-hoc Dunnett | PBS | 0.05 | * | 0.0112 |
| Vascular stability (4k; 9c (H8)) | PBS | 7 | 1way ANOVA with post-hoc Dunnett | N/A | N/A | N/A | N/A |
| | A1F-Fc | 6 | 1way ANOVA with post-hoc Dunnett | PBS | 0.05 | ns | 0.9932 |
| | o42.1 Fc | 4 | 1way ANOVA with post-hoc Dunnett | PBS | 0.05 | ns | >0.9999 |
| | i52.3 Fc | 3 | 1way ANOVA with post-hoc Dunnett | PBS | 0.05 | ns | 0.8699 |
| | o42.1 A1F-Fc | 6 | 1way ANOVA with post-hoc Dunnett | PBS | 0.05 | *** | 0.0006 |
| | i52.3 A1F-Fc | 5 | 1way ANOVA with post-hoc Dunnett | PBS | 0.05 | **** | <0.0001 |
| | H8-A1F | 4 | 1way ANOVA with post-hoc Dunnett | PBS | 0.05 | * | 0.0208 |
| pAKT (HS exp.) | PBS | 3 | 1way ANOVA with post-hoc Dunnett | o42.1 A1F-Fc | 0.05 | *** | <0.0001 |
| | o42.1 A1F-Fc | 3 | 1way ANOVA with post-hoc Dunnett | o42.1 A1F-Fc | 0.05 | N/A | N/A |
| | 10% HS | 3 | 1way ANOVA with post-hoc Dunnett | o42.1 A1F-Fc | 0.05 | *** | 0.0002 |
| | o42.1 A1F-Fc 10% HS 4 °C | 3 | 1way ANOVA with post-hoc Dunnett | o42.1 A1F-Fc | 0.05 | ns | 0.9431 |
| | o42.1 A1F-Fc 10% HS | 3 | 1way ANOVA with post-hoc Dunnett | o42.1 A1F Fc | 0.05 | ns | 0.9998 |

Tube Formation Assay (Vascular Stability)

Tube formation was done with modified protocol from Liang et al., 2007. Briefly, passage 6 HUVECs were seeded onto 24-well plates precoated with 150 μL of 100% cold Matrigel™ (Corning, USA) at 150,000 cells/well density along with scaffolds at 89 nM A1F-Fc concentrations or PBS in low glucose DMEM medium supplemented with 0.5% FBS for 24 hours. At the 24 hour time point, old media is aspirated and replaced with fresh media without scaffolds. The cells continue to be incubated up to 72 hours. Cells were imaged at 48-hour and 72-hour time points using Leica Microscope at 10× magnification under phase contrast. Thereafter, the tubular formations were quantified by calculating the number of nodes, meshes and tubes using Angiogenesis Analyzer plugin in Image J software. Vascular stability is calculated by averaging the number of nodes, meshes, and tubes then normalizing to PBS. Statistical comparisons were performed using Graphpad Prism™ (see Table 12 for full detail).

Immune Cell Activation Materials and Methods

CD40 Luminescence Assay

Figure 5:
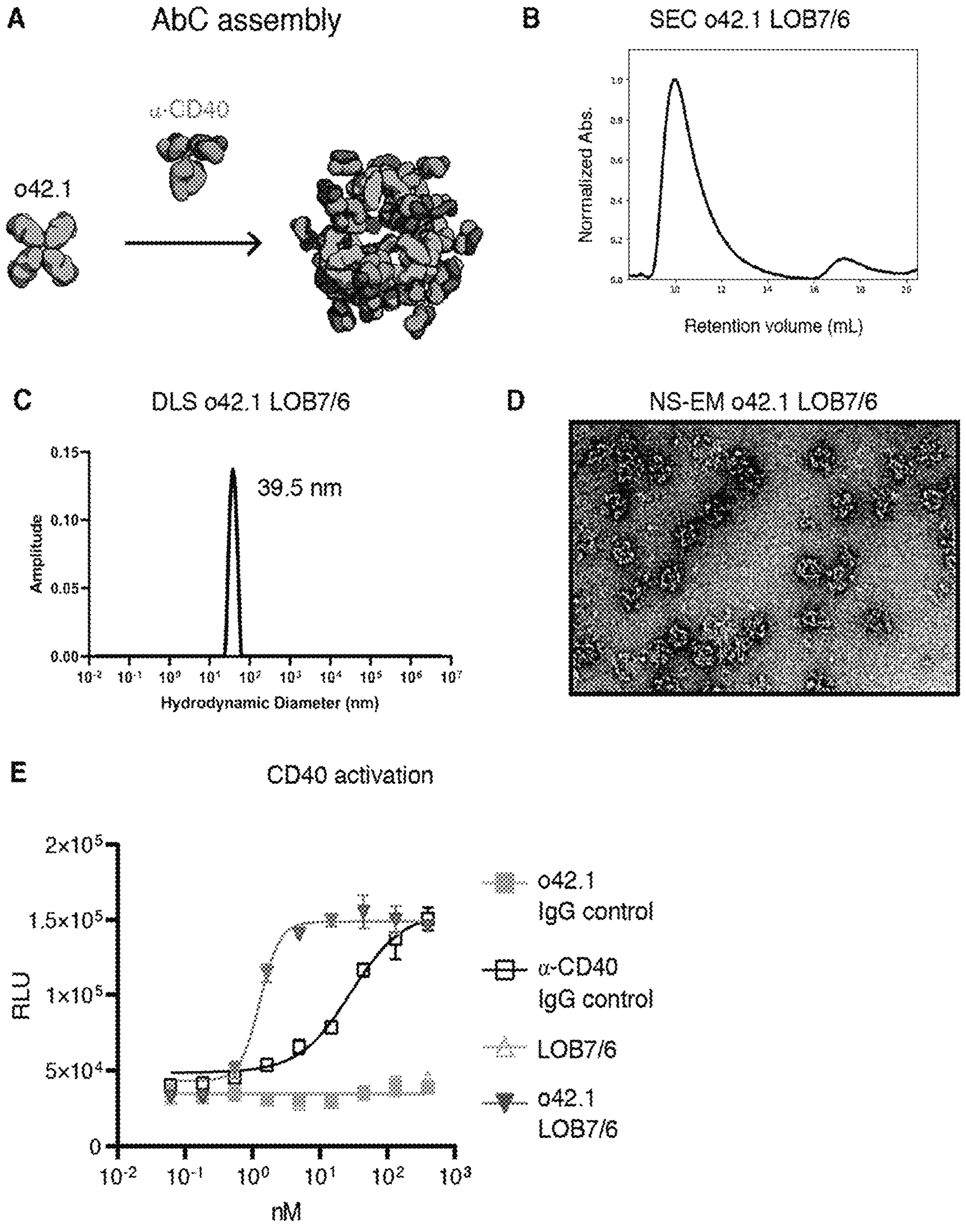
FIG. 5(A-E). α-CD40 AbCs activate CD40 signaling over uncaged IgGs. A-D, Octahedral AbCs produced with α-CD40 (A) form AbCs of the expected size and shape according to SEC (B), DLS (C), and NS-EM (D). E, CD40 pathways are activated by LOB7/6 α-CD40 octahedral nanocages but not by free LOB7/6. Scale bars represent means SD, n=3; EC50s reported in Table 7.

A non-agonistic antibody (clone LOB7/6, product code MCA1590T, BioRad), was combined with the octahedral o42.1 AbC-forming design as described above and the AbCs were characterized by DLS and NS-EM (FIG. 5). Negative control o42.1 AbC was made using a non-CD40 binding IgG (mpe8), which binds to RSV spike protein (45). These two AbCs, along with uncaged LOB7/6 and a positive control CD40-activating IgG (Promega, catalog #K118A) were diluted to make a 10-point, threefold dilution series for triplicate technical repeats starting at 1.2 μM. The positive control CD40-activating IgG (K118A) is a murine IgG1a antibody, and so it was not compatible for assembly with the o42.1 design, likely due to the low binding interface between protein A and mIgG1a (data not shown).

To assay CD40 activation, we followed manufacturer's instructions for a bioluminescent cell-based assay that measures the potency of CD40 response to external stimuli such as IgGs (Promega, JA2151). Briefly, CD40 effector Chinese Hamster Ovary (CHO) cells were cultured and reagents were prepared according to the assay protocol. The antibodies and AbCs were incubated with the CD40 effector CHO cells for 8 hours at 37 °C, 5% CO2. Bio-Glo™ Luciferase Assay System (G7941) included in the assay kit was used to visualize the activation of CD40 from luminescence readout from a plate reader. The Bio-Glo™ Reagent was applied to the cells and luminescence was detected by a Synergy Neo2 plate reader every min for 30 minutes. Data were analyzed by averaging luminescence between replicates and subtracting plate background. The fold induction of CD40-binding response was determined by RLU of sample normalized to RLU of no antibody controls. Data curves were plotted and EC50 was calculated using GraphPad Prism™ using the log(agonist) vs. response—Variable slope (four parameters); see Table 7 for EC50 values and 95% CI values.

We claim:

1. An antibody cage particle comprising:

(a) a plurality of α-TNFRSF antibodies; and (b) a plurality of cyclic oligomers, each cyclic oligomer comprising a polypeptide comprising an amino acid sequence at least 90% identical to any one of SEQ ID NOs: 1-9 with optional residues omitted.

2. The antibody cage particle of claim 1, wherein the α-TNFRSF antibodies each comprise an amino acid sequence at least 90% identical to SEQ ID NOs: 38 and 39.

3. The antibody cage particle of claim 1, wherein the α-TNFRSF antibodies each comprise an amino acid sequence according to SEQ ID NOs: 38 and 39.

4. The antibody cage particle of claim 1, wherein the polypeptide comprises an amino acid sequence according to any one of SEQ ID NO: 1-9 with optional residues omitted.

5. The antibody cage particle of claim 1, wherein the polypeptide comprises an amino acid sequence at least 90% identical to SEQ ID NO: 6 with optional residues omitted.

6. The antibody cage particle of claim 1, wherein the polypeptide comprises an amino acid sequence at least 90% identical to SEQ ID NO: 7 with optional residues omitted.

7. An antibody cage particle comprising:

(a) a plurality of α-Tie2 antibodies; and (b) a plurality of cyclic oligomers, each cyclic oligomer comprising a polypeptide comprising an amino acid sequence at least 90% identical to any one of SEQ ID NOs: 1-9 with optional residues omitted.

8. The antibody cage particle of claim 7, wherein the polypeptide comprises an amino acid sequence according to any one of SEQ ID NO: 1-9 with optional residues omitted.

9. The antibody cage particle of claim 7, wherein the polypeptide comprises an amino acid sequence at least 90% identical to SEQ ID NO: 6 with optional residues omitted.

10. The antibody cage particle of claim 7, wherein the polypeptide comprises an amino acid sequence at least 90% identical to SEQ ID NO: 7 with optional residues omitted.

11. A Fc fusion protein cage particle comprising:

(a) a plurality of dimers of fibrinogen-like domain derived from angiopoietin (Ang F domain) fused to an Fc domain (Ang F domain dimers); and (b) a plurality of cyclic oligomers, each cyclic oligomer comprising a polypeptide comprising the amino acid sequence at least 90% identical to any one of SEQ ID NOs: 1-9 with optional residues omitted.

12. The Fc fusion protein cage particle of claim 11, wherein the Ang F domains dimers each comprise a monomer comprising an amino acid sequence at least 90% identical to any one of SEQ ID NOs: 17-18 and 47.

13. The Fc fusion protein cage particle of claim 12, wherein the Ang F domain dimers each comprise a monomer comprising an amino acid sequence according to any one of SEQ ID NOs: 17-18 and 47.

14. The Fc fusion protein case nanoparticle of 11, wherein the polypeptide comprises an amino acid sequence according to any one of SEQ ID NOs: 1-9 with optional residues omitted.

* * * * *